United States Patent
Freeman et al.

(10) Patent No.: US 11,925,439 B2
(45) Date of Patent: Mar. 12, 2024

(54) DATA PLAYBACK INTERFACE FOR A MEDICAL DEVICE

(71) Applicant: ZOLL Medical Corporation, Chelmsford, MA (US)

(72) Inventors: Gary A Freeman, Waltham, MA (US); Annemarie E Silver, Bedford, MA (US); Timothy F Stever, Lowell, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 97 days.

(21) Appl. No.: 16/659,807

(22) Filed: Oct. 22, 2019

(65) Prior Publication Data
US 2020/0121199 A1  Apr. 23, 2020

Related U.S. Application Data

(60) Provisional application No. 62/749,212, filed on Oct. 23, 2018.

(51) Int. Cl.
*A61B 5/0205* (2006.01)
*A61B 5/00* (2006.01)
(Continued)

(52) U.S. Cl.
CPC ............ *A61B 5/02055* (2013.01); *A61B 5/01* (2013.01); *A61B 5/026* (2013.01);
(Continued)

(58) Field of Classification Search
CPC .... G16H 20/30; G16H 10/20; A61N 1/39044; A61N 1/3968; A61N 1/3993;
(Continued)

(56) References Cited

U.S. PATENT DOCUMENTS 5,414,644 A   5/1995 Seaman et al.
5,813,403 A   9/1998 Soller et al.
(Continued)

FOREIGN PATENT DOCUMENTS

CN    101952796    1/2011
JP    2002263070   10/2005
(Continued)

OTHER PUBLICATIONS

PCT Search Report and Written Opinion for PCT Application No. PCT/US2019/057353, dated Jan. 30, 2020, 13 pages.
(Continued)

*Primary Examiner* — Carl H Layno
*Assistant Examiner* — Aya Ziad Bakkar
(74) *Attorney, Agent, or Firm* — Finch & Maloney PLLC

(57) ABSTRACT

A medical device for review of clinical data in a playback mode is described. The medical device includes at least one output device comprising at least one display screen, at least one memory, and at least one processor coupled to the at least one memory and the at least one output device, the at least one processor configured to receive signals indicative of patient data from one or more patient interface devices communicatively coupled to the medical device, control the at least one display screen to provide a first visual representation of the patient data as an operational interface, and selectively display a playback interface at the at least one display screen wherein the playback interface enables user interactive review of the patient data based on a second visual representation of the patient data.

35 Claims, 20 Drawing Sheets

(51) Int. Cl.

| | | |
|---|---|---|
| *A61B 5/01* | (2006.01) | |
| *A61B 5/021* | (2006.01) | |
| *A61B 5/024* | (2006.01) | |
| *A61B 5/026* | (2006.01) | |
| *A61B 5/145* | (2006.01) | |
| *A61B 5/1455* | (2006.01) | |
| *A61B 5/339* | (2021.01) | |
| *A61B 5/369* | (2021.01) | |
| *A61B 7/00* | (2006.01) | |
| *A61N 1/39* | (2006.01) | |
| *G06F 3/0481* | (2022.01) | |
| *G06F 3/0482* | (2013.01) | |
| *G06F 3/04847* | (2022.01) | |
| *G06F 3/0486* | (2013.01) | |
| *G06F 3/04883* | (2022.01) | |
| *G06F 3/14* | (2006.01) | |
| *G16H 10/20* | (2018.01) | |
| *G16H 20/30* | (2018.01) | |
| *A61B 5/08* | (2006.01) | |
| *A61B 5/083* | (2006.01) | |

(52) U.S. Cl.
CPC ...... *A61B 5/14532* (2013.01); *A61B 5/14539* (2013.01); *A61B 5/14551* (2013.01); *A61B 5/339* (2021.01); *A61B 5/369* (2021.01); *A61B 5/4875* (2013.01); *A61B 7/003* (2013.01); *A61N 1/39044* (2017.08); *A61N 1/3968* (2013.01); *A61N 1/3993* (2013.01); *G06F 3/0481* (2013.01); *G06F 3/0482* (2013.01); *G06F 3/04847* (2013.01); *G06F 3/0486* (2013.01); *G06F 3/04883* (2013.01); *G06F 3/14* (2013.01); *G16H 10/20* (2018.01); *G16H 20/30* (2018.01); *A61B 5/021* (2013.01); *A61B 5/024* (2013.01); *A61B 5/0809* (2013.01); *A61B 5/0816* (2013.01); *A61B 5/0836* (2013.01); *G06F 2203/04803* (2013.01)

(58) Field of Classification Search
CPC ......... A61B 5/369; A61B 5/339; A61B 5/026; A61B 5/14532; A61B 5/14539; A61B 5/14551; A61B 5/4875; A61B 7/003; A61B 5/021; A61B 5/024; A61B 5/0836; A61B 5/0816; G06F 3/0481; G06F 3/0482; G06F 3/04847; G06F 3/0486; G06F 3/04883; G06F 3/14; G06F 2203/04803

See application file for complete search history.

(56) References Cited

U.S. PATENT DOCUMENTS

| | | | |
|---|---|---|---|
| 6,055,447 A | 4/2000 | Weil et al. | |
| 6,073,033 A | 6/2000 | Campo | |
| 6,364,834 B1 | 4/2002 | Reuss et al. | |
| 6,564,088 B1 | 5/2003 | Soller et al. | |
| 6,766,188 B2 | 7/2004 | Soller | |
| 6,820,057 B1 | 11/2004 | Loch et al. | |
| 7,188,151 B2 | 3/2007 | Kumar et al. | |
| 7,330,426 B2 | 2/2008 | Berzosa et al. | |
| 8,255,238 B2 | 8/2012 | Powell et al. | |
| 8,315,688 B2 | 11/2012 | Ueda | |
| 8,608,657 B2 | 12/2013 | Pinto et al. | |
| 8,738,129 B2 | 5/2014 | Packer et al. | |
| 8,856,729 B2 | 10/2014 | Moore et al. | |
| 8,870,742 B2 | 10/2014 | Dlugos, Jr. et al. | |
| 9,246,991 B2 | 1/2016 | Moore et al. | |
| 9,357,262 B2 | 5/2016 | Vanduyn et al. | |
| 9,392,217 B2 | 7/2016 | Defazio et al. | |
| 9,400,874 B2 | 7/2016 | Powell et al. | |
| 9,463,108 B2 | 10/2016 | Anglada et al. | |
| 9,524,569 B2 | 12/2016 | Moore et al. | |
| 9,658,756 B2 | 5/2017 | Freeman et al. | |
| 9,996,667 B2 | 6/2018 | Moore et al. | |
| 10,032,236 B2 | 7/2018 | Hawkins et al. | |
| 10,042,979 B2 | 8/2018 | Moore et al. | |
| 10,068,057 B2 | 9/2018 | Moore | |
| 10,111,591 B2 | 10/2018 | Dyell et al. | |
| 10,262,382 B2 | 4/2019 | Moore et al. | |
| 10,282,518 B2 | 5/2019 | Powell et al. | |
| 10,300,293 B2 | 5/2019 | Dascoli et al. | |
| 10,349,875 B2 | 7/2019 | Freeman et al. | |
| 2002/0070957 A1 | 6/2002 | Trajkovic et al. | |
| 2002/0156503 A1* | 10/2002 | Powers | A61N 1/3925 607/5 |
| 2004/0051721 A1 | 3/2004 | Ramseth | |
| 2004/0054261 A1 | 3/2004 | Kamataki et al. | |
| 2004/0204635 A1 | 10/2004 | Scharf et al. | |
| 2006/0173501 A1 | 8/2006 | Stickney et al. | |
| 2006/0229557 A1 | 10/2006 | Fathallah et al. | |
| 2008/0261192 A1 | 10/2008 | Huang et al. | |
| 2009/0073114 A1 | 3/2009 | Bay et al. | |
| 2010/0131293 A1 | 5/2010 | Linthicum et al. | |
| 2010/0235782 A1 | 9/2010 | Powell et al. | |
| 2011/0055720 A1 | 3/2011 | Potter et al. | |
| 2011/0172550 A1 | 7/2011 | Martin et al. | |
| 2011/0246235 A1 | 10/2011 | Powell et al. | |
| 2012/0123223 A1 | 5/2012 | Freeman et al. | |
| 2012/0191464 A1 | 7/2012 | Stuart et al. | |
| 2012/0278099 A1 | 11/2012 | Kelly et al. | |
| 2013/0271469 A1 | 10/2013 | Moore et al. | |
| 2013/0275145 A1 | 10/2013 | Moore et al. | |
| 2014/0249855 A1 | 9/2014 | Moore | |
| 2014/0278488 A1 | 9/2014 | Moore | |
| 2015/0088549 A1 | 3/2015 | Moore et al. | |
| 2015/0178457 A1 | 6/2015 | Grimley et al. | |
| 2015/0227694 A1 | 8/2015 | Grimley | |
| 2015/0374328 A1 | 12/2015 | Ginestet et al. | |
| 2016/0058287 A1 | 3/2016 | Dyell et al. | |
| 2016/0135706 A1 | 5/2016 | Sullivan et al. | |
| 2016/0303389 A1* | 10/2016 | Peterson | A61N 1/3993 |
| 2017/0083620 A1* | 3/2017 | Chew | G06F 16/345 |
| 2017/0086719 A1* | 3/2017 | Freeman | A61B 5/14539 |
| 2017/0161014 A1* | 6/2017 | Kikugawa | G10L 15/04 |
| 2017/0193182 A1 | 7/2017 | Mihai | |
| 2017/0249435 A1 | 8/2017 | Lancelot | |
| 2017/0252571 A1* | 9/2017 | Dascoli | A61N 1/3925 |
| 2017/0293726 A1* | 10/2017 | Freeman | G06F 3/0485 |
| 2017/0300653 A1* | 10/2017 | Hresko | G16H 40/60 |
| 2018/0200142 A1 | 7/2018 | Freeman et al. | |
| 2018/0235537 A1* | 8/2018 | Whiting | A61N 1/3621 |

FOREIGN PATENT DOCUMENTS

| | | |
|---|---|---|
| JP | 2007233850 | 9/2007 |
| JP | 2008301984 | 12/2008 |
| JP | 2009233042 | 10/2009 |
| JP | 2010217153 | 9/2010 |
| JP | 2011036371 | 2/2011 |
| JP | 200939357 | 12/2012 |
| WO | 2006001055 | 1/2006 |
| WO | 2011116340 | 9/2011 |
| WO | 2012017342 | 2/2012 |
| WO | 2012/065167 | 5/2012 |
| WO | 2012065131 | 5/2012 |
| WO | 2012148934 | 11/2012 |
| WO | 2011122402 | 7/2013 |

OTHER PUBLICATIONS

Hernandez, et al., "C.A.U.S.E.: Cardiac Arrest Ultra-Sound Exam—A Better Approach to Managing Patients in Primary Non-Arrhythmogenic Cardiac Arrest", Resuscitation, 76(2):198-206, Feb. 2008, Published online Sep. 6, 2007.

Zoorob, et al., "Acute Dyspnea in the Office", American Family Physician, 68(9):1803-1811, Nov. 1, 2003, 6 Pages.

(56) References Cited

OTHER PUBLICATIONS

PCT Search Report and Written Opinion for PCT Application No. PCT/US2020/023479, dated Jun. 19, 2020, 17 pages.

* cited by examiner

DATA PLAYBACK INTERFACE FOR A MEDICAL DEVICE

CROSS-REFERENCE TO RELATED APPLICATIONS

This application claims the benefit under 35 U.S.C. § 119(e) of U.S. Provisional Application No. 62/749,212 filed Oct. 23, 2018. All subject matter set forth in the above referenced application is hereby incorporated by reference in its entirety into the present application as if fully set forth herein.

BACKGROUND

Caregivers, rescuers, and supervisory medical personnel typically review data collected during a patient treatment, for example an emergency medical encounter, in order to determine and provide appropriate patient treatments and to evaluate the efficacy of those treatments. A user interface configured to provide data collected during patient treatment may enable this review. The reviewed data may include physiological data for the patient such as electrocardiograms, heart rate, blood pressure, and other indicators necessary for the provision of effective treatment.

SUMMARY

An example of an external defibrillator for review of clinical data in a playback mode, the external defibrillator includes at least one output device including at least one first display screen, a communications module, at least one first memory, and at least one first processor coupled to the at least one first memory and the at least one first display screen, the at least one first processor configured to receive signals indicative of patient data from one or more patient interface devices communicatively coupled to the external defibrillator, the one or more patient interface devices including electrotherapy electrodes and one or more physiological sensors, and the patient data comprising physiological data including electrocardiogram (ECG) data and one or more of pulse oximetry data and capnography data, control the at least one first display screen to provide a first visual representation of the patient data as an operational interface, and selectively display a playback interface at the at least one first display screen wherein the playback interface enables user interactive review of the patient data based on a second visual representation of the patient data.

Implementations of such an external defibrillator may include one or more of the following features. The external defibrillator may be a component of a modular therapeutic medical device/patient monitor. The modular therapeutic medical device/patient monitor may include a patient monitor including a second processor, a second memory, and at least one second display screen. The one or more of the at least one first processor and the second processor may be configured to control one or more of the at least one first display screen and the at least one second display screen to selectively provide the playback interface. The playback interface may be configured to provide a real-time portion of the patient data and a historical portion of the patient data. The patient data may include a plurality of time stamps. The real-time portion of the patient data may correspond to time stamps of the plurality of time stamps that are within a threshold time interval from a current time. The historical portion of the patient data may correspond to time stamps of the plurality of time stamps that are greater than the threshold time interval from the current time and less or equal to a time difference between the current time and a start time of data collection for a case by the external defibrillator. The selective display of the playback interface may include the at least one first processor being configured to implement a display mode for the at least one output device selected from a plurality of display modes including an operational interface only mode that excludes the playback interface, a playback interface only mode, and a combined operational/playback mode. The display mode may be a user selected display mode. The external defibrillator may be configured to capture a user input indicative of the user selected display mode. The at least one first processor may be configured to detect whether the external defibrillator is coupled to a patient via the one or more patient interface devices, and, in response to a detection that the external defibrillator is coupled to the patient via the one or more patient interface devices, disallow selection of one or more of the plurality of display modes. The display mode may be a processor-selected display mode and the processor may be configured to detect a state of the external defibrillator, and automatically determine the processor-selected display mode based on the detected state of the external defibrillator. The combined operational/playback mode may enable a simultaneous display on the at least one first display screen of the operational interface and the playback interface. The operational interface and the playback interface may include one or more of different colors and different labels to visually distinguish between the operational interface and the playback interface. The at least one first display screen may provide the operational interface on a first portion of the at least one first display screen and the playback interface on a second portion of the at least one first display screen. One of the operational interface and the playback interface may occupy a smaller area on the at least one first display screen than the other of the operational interface and the playback interface. The first visual representation of the patient data may be the same as the second visual representation of the patient data. The first visual representation of the patient data may be different that the second visual representation of the patient data. The one or more patient interface devices may include one or more of ventilation and/or respiration sensors, cardiac sensing electrodes, and at least one chest compression sensor. The patient data may include chest compression data including one or more of displacement data, velocity data, release velocity data, acceleration data, force data, compression rate data, dwell time data, hold time data, blood flow data, and blood pressure data. The physiological data may include blood pressure, heart rate, respiration rate, heart sounds, lung sounds, respiration sounds, saturation of muscle oxygen (SMO2), cerebral blood flow, electroencephalogram (EEG) signals, brain oxygen level, tissue pH, tissue fluid levels, ultrasound images and/or video, laryngoscope images and/or video, near-infrared reflectance spectroscopy data, pneumography data, cardiography data, lactate, glucose, point of care laboratory measures, and temperature. The playback interface may include a data display window configured to provide a visual representation of the patient data, an interactive timeline configured to capture first user input indicative of a time interval selection for the visual representation of the patient data, and a media navigation bar configured to capture second user input indicative of data display parameters and to control the visual representation of the patient data based on the second user input. The visual representation of the patient data includes one or more of waveforms, time trends, and discrete physiological measurements for one or more of cardiac parameters and ventilation and/or respiration parameters and/or one or more of a textual, numerical, and graphical representation of cardiopulmonary resuscitation (CPR) performance data. The interactive timeline may include one or more visual event indicators and may be configured to capture a user selection of at least one visual event indicator of the one or more visual event indicators, wherein the data display window may be configured to provide the visual representation of the patient data that corresponds to the selected at least one visual event indicator, a first time interval selector may be configured to indicate a start time of the visual representation of the patient data, and a second time interval selector may be configured to indicate an end time of the visual representation of the patient data. The first time interval selector and the second time interval selector may be configured to move along the interactive timeline in response to user input. The interactive timeline may be configured to provide a data preview pop-up window in response to a touchscreen gesture associated with an on-screen cursor. The data preview pop-up window may be configured to provide a visual representation of at least a portion of the patient data that corresponds to a time associated with a position of the on-screen cursor along the interactive timeline. The data preview pop-up window may provide one or more of an ECG waveform, CPR performance data, physiological waveforms, discrete physiological measurements, device settings, and device actions. The playback interface may include a playback speed selection control configured to adjust a playback speed for the patient data visually represented in the data display window. The playback interface may be configured to automatically adjust the playback speed to provide a historical portion of the patient data at a speed determined by the playback speed selection control and provide a real-time portion of the patient data at a speed that matches a data display speed for the operational interface. The playback interface may include an event search function. The playback interface may be configured to provide a user-selectable list of events on an interactive menu in response to a user activation of the event search function and may be configured to highlight visual indicators on the interactive timeline in response to a user selection of an event from the user-selectable list of events. The playback interface may include a medical condition selection control configured to enable a user selection of a medical condition from an interactive menu of the playback interface, and determine one or more settings for data display at the playback interface based on the user selection of the medical condition. The external defibrillator may be configured to provide the patient data to at least one auxiliary device via the communications module. The at least one auxiliary device may include a tablet computer including a second display. The tablet computer may be configured to selectively display a second playback interface at the second display. The second playback interface may enable a user interactive review of the patient data at the tablet computer. The playback interface may be configured to capture a user input of a selected data type to display at the at least one auxiliary device. The at least one first processor may be configured to provide an instruction comprising the selected data type to display to the at least one auxiliary device via the communications module. The playback interface may include a plurality of data type icons and an icon representative of the at least one auxiliary device and may be configured to enable a user of the playback interface to drag a data type icon to the icon representative of the at least one auxiliary device and drop the data type icon at the icon representative of the at least one auxiliary device such that a particular data type that corresponds to the data type icon is selected for display at the at least one auxiliary device, wherein the drag and the drop are touchscreen gestures. The at least one first processor may be configured to evaluate patient interface information and determine a relative criticality of care between the external defibrillator and the at least one auxiliary device. The patient interface information may include an indication that the external defibrillator is coupled to a patient via the one or more patient interface devices and an indication of one or more of a type of therapy and a type of sensor provided by the one or more patient interface devices.

An example of a medical device for review of clinical data in a playback mode according to the disclosure includes at least one output device including at least one display screen, a memory, and at least one processor coupled to at least one memory and the at least one output device, the at least one processor configured to receive signals indicative of patient data from one or more patient interface devices communicatively coupled to the medical device, control the at least one display screen to provide a first visual representation of the patient data as an operational interface, and selectively display a playback interface at the at least one display screen wherein the playback interface enables user interactive review of the patient data based on a second visual representation of the patient data.

Implementations of such a medical device may include one or more of the following features. The medical device may include a therapeutic medical device. The one or more patient interface devices may include one or more therapy delivery components. The therapeutic medical device may be configured to couple to the one or more therapy delivery components and provide therapy to a patient via the one or more therapy delivery components. The therapeutic medical device may include a defibrillator or a defibrillator/patient monitor. The one or more therapy delivery components may include electrotherapy electrodes. The patient data may include one or more of electrocardiogram (ECG) data and transthoracic impedance data. The one or more therapy delivery components may include a chest compression monitor. The patient data may include chest compression parameters. The one or more patient interface devices may include one or more sensors. The device may include a patient monitor. The one or more patient interface devices may include one or more sensor devices. The patient monitor may be configured to couple to the one or more sensor devices and monitor the patient data via the one or more sensor devices. The patient data may include physiological sensor data. The medical device may include a modular therapeutic medical device/patient monitor. The modular therapeutic medical device/patient monitor may include a therapeutic medical device including a first processor, a first memory, and a first display screen and a patient monitor including a second processor, a second memory, and a second display screen. One or more of the first processor and the second processor may be configured to control one or more of the first display screen and the second display screen to selectively provide the playback interface. The therapeutic medical device may include a defibrillator. The playback interface may be configured to provide a real-time portion of the patient data and a historical portion of the patient data. The patient data may include a plurality of time stamps. The real-time portion of the patient data may correspond to time stamps of the plurality of time stamps that may be within a threshold time interval from a current time. The historical portion of the patient data may correspond to time stamps of the plurality of time stamps that may be greater than the threshold time interval from the current time and less or equal to a time difference between the current time and a start time of data collection for a case by the medical device. The selective display of the playback interface may include the at least one processor being configured to implement a display mode for the at least one output device selected from a plurality of display modes including an operational interface only mode that excludes the playback interface, a playback interface only mode, and a combined operational/playback mode. The display mode may be a user selected display mode and the medical device may be configured to capture a user input indicative of the user selected display mode. The at least one processor may be configured to detect whether the medical device is coupled to a patient via the one or more patient interface devices, and in response to a detection that the medical device may be coupled to the patient via the one or more patient interface devices, disallow selection of one or more of the plurality of display modes. The display mode may be a processor-selected display mode and the processor may be configured to detect a state of the medical device and automatically determine the processor-selected display mode based on the detected state of the medical device. The combined operational/playback mode may enable a simultaneous display on the at least one display screen of the operational interface and the playback interface. The operational interface and the playback interface may include one or more of different colors and different labels to visually distinguish between the operational interface and the playback interface. The at least one display screen may provide the operational interface on a first portion of the at least one display screen and the playback interface on a second portion of the at least one display screen. One of operational interface and the playback interface may occupy a smaller area on the at least one display screen than the other of the operational interface and the playback interface. A default state of the medical device may provide the playback interface in the smaller area on the at least one display screen. The memory may include a user configurable processor-executable instruction that may be configured to cause the at least one processor to maintain the playback interface in the smaller area on the at least one display screen. The medical device may be configured to capture user input including a selection of the one of the operational interface and the playback interface to occupy the smaller area on the at least one display screen. The at least one processor may be configured to control the at least one display screen to display the one of the operational interface and the playback interface in the smaller area of the at least one display screen according to the user input. The at least one processor may be configured to detect a medical device event and to provide a display mode message in response to the detection of the medical device event. The display mode message may include an instruction for a user of the medical device to select the playback interface to occupy the smaller area on the at least one display screen. The medical device event may include at least one of a delivery of a defibrillation shock and a heart rhythm analysis. The at least one display screen may include a touchscreen and the user input may include a touchscreen gesture. The at least one processor may be configured to override the captured user input and display the playback interface in the smaller area of the at least one display screen in response to a detection of a state of the medical device. The state of the medical device may include the medical device being coupled to a patient via the one or more patient interface devices. The state of the medical device may include an alarm state. The at least one processor may be configured to generate an alarm indicative of the override of the captured user input. The alarm may include one or more of a visible message, an audible sound, and a haptic output. The first visual representation of the patient data may be the same as the second visual representation of the patient data. The first visual representation of the patient data may be different that the second visual representation of the patient data. The one or more patient interface devices may include one or more of ventilation and/or respiration sensors and cardiac sensing electrodes. The ventilation and/or respiration sensors may include one or more of spirometry sensors, flow sensors, oxygen sensors, carbon dioxide sensors, pulse oximetry sensors, capnography sensors, impedance sensors, and combinations thereof. The one or more patient interface devices may include at least one chest compression sensor. The at least one chest compression sensor may include at least one of one or more accelerometers, one or more force sensors, one or more magnetic sensors, one or more velocity sensors, and one or more displacement sensors. The patient data may include one or more of physiological data and chest compression data. The physiological data may include one or more of an electrocardiogram (ECG), blood pressure, heart rate, respiration rate, heart sounds, lung sounds, respiration sounds, end tidal carbon dioxide, saturation of muscle oxygen ($SMO_2$), oxygen saturation, cerebral blood flow, electroencephalogram (EEG) signals, brain oxygen level, tissue pH, tissue fluid levels, ultrasound images of the patient's heart, near-infrared reflectance spectroscopy data, pneumography data, and cardiography data. The chest compression data may include one or more of displacement data, velocity data, release velocity data, acceleration data, force data, compression rate data, dwell time data, hold time data, blood pressure data, and blood flow data. The playback interface may include a data display window configured to provide a visual representation of the patient data, an interactive timeline configured to capture first user input indicative of a time interval selection for the visual representation of the patient data, and a media navigation bar configured to capture second user input indicative of data display parameters and to control the visual representation of the patient data based on the second user input. The visual representation of the patient data may include one or more of waveforms, time trends, and discrete physiological measurements for one or more of cardiac parameters and ventilation and/or respiration parameters. The visual representation of the patient data may include one or more of a textual, numerical, and graphical representation of cardiopulmonary resuscitation (CPR) performance data. The CPR performance data may include one or more of a compression depth, a compression rate, a chest release indicator, a perfusion performance indicator, a CPR time indicator, blood flow data, and blood pressure data. The interactive timeline may include a first time interval selector configured to indicate a start time of the visual representation of the patient data, and a second time interval selector configured to indicate an end time of the visual representation of the patient data. The first time interval selector and the second time interval selector may be configured to move along the interactive timeline in response to user input. The interactive timeline may include one or more visual event indicators and may be configured to capture a user selection of at least one visual event indicator of the one or more visual event indicators. The data display window may be configured to provide the visual representation of the patient data that may correspond to the selected at least one visual event indicator. The interactive timeline may be configured to provide a data preview pop-up window in response to a touchscreen gesture associated with an on-screen cursor. The data preview pop-up window may be configured to provide a visual representation of at least a portion of the patient data that may correspond to a time associated with a position of the on-screen cursor along the interactive timeline. The data preview pop-up window may provide one or more of an ECG waveform, CPR performance data, physiological waveforms, discrete physiological measurements, device settings, and device actions. The media navigation bar may include user interactive data display controls configured to enable a user to control playback of data at the playback interface. The user interactive data display controls may include one or more of a rewind control, a play control, a stop control, a pause control, and a fast forward control, a skip back control, and skip forward control. The playback interface may include a playback speed selection control configured to adjust a playback speed for the patient data visually represented in the data display window. The playback interface may be configured to automatically adjust the playback speed to provide a historical portion of the patient data at a speed determined by the playback speed selection control. The playback interface may be configured to automatically adjust the playback speed to provide a real-time portion of the patient data at a speed that matches a data display speed for the operational interface. The playback interface may include an event search function. The playback interface may be configured to provide a user-selectable list of events on an interactive menu in response to a user activation of the event search function. The playback interface may be configured to highlight visual indicators on the interactive timeline in response to a user selection of an event from the user-selectable list of events. The playback interface may include a medical condition selection control configured to enable a user selection of a medical condition from an interactive menu of the playback interface, and determine one or more settings for data display at the playback interface based on the user selection of the medical condition. The playback interface may include a data preview area. The medical device may be a first medical device and may include a communications module. The first medical device may be configured to provide the patient data to at least one auxiliary device via the communications module, the at least one auxiliary device including a second medical device or a computing device. The playback interface may be configured to capture a user input of a selected data type to display at the at least one auxiliary device. The at least one processor may be configured to provide an instruction including the selected data type to display to the at least one auxiliary device via the communications module. The playback interface may include a display of a plurality of selectable data types and may be configured to capture the user input of the selected data type based on the display. The plurality of selectable data types may include one or more of ventilation and/or respiration data, cardiac data, and cardiopulmonary resuscitation data. The ventilation and/or respiration data may include one or more of capnography data and pulse oximetry data and wherein the cardiac data may include electrocardiogram data. The display of the plurality of selectable data types may include a plurality of data type icons wherein each data type icon of the plurality of data type icons may correspond to a particular data type. The playback interface may include a plurality of data type icons and an icon representative of the at least one auxiliary device and may be configured to enable a user of the playback interface to drag a data type icon to the icon representative of the at least one auxiliary device and drop the data type icon at the icon representative of the at least one auxiliary device such that a particular data type that may correspond to the data type icon may be selected for display at the at least one auxiliary device. The at least one display screen may include a touchscreen and the drag and the drop may be touchscreen gestures. The at least one processor may be configured to evaluate patient interface information and determine a relative criticality of care between the first medical device and the at least one auxiliary device. The patient interface information may include an indication that the first medical device may be coupled to a patient via the one or more patient interface devices and an indication of one or more of a type of therapy and a type of sensor provided by the one or more patient interface devices.

An example of a system for review of clinical data in a playback mode according to the disclosure includes a first medical device including at least one first output device including at least one first display screen, a first memory, a first communications module, and at least one first processor coupled to the first memory, the at least one first output device, and the first communications module, and at least one auxiliary device configured to communicatively couple to the first medical device, the at least one auxiliary device including at least one second output device including at least one second display screen, a second memory, a second communications module, wherein the first communications module and the second communications module may be configured to communicatively couple the at least one auxiliary device to the first medical device, and at least one second processor coupled to the second memory, the at least one second output device, and the second communications module, wherein the at least one first processor may be configured to receive signals indicative of first patient data from one or more first patient interface devices coupled to the first medical device, control the at least one first display screen to provide the first patient data as a first operational interface, selectively display a first playback interface wherein the first playback interface enables a user interactive review of the first patient data at the first medical device, and provide the first patient data to the first communications module, and wherein the at least one second processor may be configured to receive the first patient data from the first medical device via the first communications module and the second communications module, and control the at least one second display screen to selectively display a second playback interface wherein the second playback interface enables a user interactive review of the first patient data at the at least one auxiliary device.

Implementation of such a system may include one or more of the following features. The first medical device may include a therapeutic medical device, a patient monitor, or a modular therapeutic medical device/patient monitor. The therapeutic medical device may include a defibrillator or a defibrillator/patient monitor. The modular therapeutic medical device/patient monitor may include a defibrillator and patient monitor configured to communicatively couple to one another. The at least one auxiliary device may include a second medical device or a computing device. The second medical device may include a therapeutic medical device, a patient monitor, or a modular therapeutic medical device/patient monitor. The therapeutic medical device may include a defibrillator or a defibrillator/patient monitor. The modular therapeutic medical device/patient monitor may include a defibrillator and patient monitor configured to communicatively couple to one another. The computing device may include a tablet computer. The at least one first processor may be configured to control the at least one first display screen to provide a first visual representation of the first patient data at the first playback interface. The at least one second processor may be configured to control the at least one second display screen to provide a second visual representation of the first patient data at the second playback interface. The first visual representation and the second visual representation may be a same visual representation. The first visual representation and the second visual representation may be different visual representations. One or more of the at least one first processor and the at least one second processor may be configured to evaluate patient interface information and determine a relative criticality of care between the first medical device and the at least one auxiliary device. The patient interface information may include an indication that the first medical device may be coupled to a patient via the one or more patient interface devices and an indication of one or more of a type of therapy and a type of sensor provided by the one or more patient interface devices. The one or more of the at least one first processor and the at least one second processor may be configured to adjust the selective display of a respective playback interface based on one or more of the patient interface information and the relative criticality of care. The one or more of the at least one first processor and the at least one second processor may be configured to determine one or more of events and time intervals to provide at one or more of the first playback interface and the second playback interface based on the patient interface information. The first medical device and the at least one auxiliary device may be configured to automatically exchange the patient interface information in response to an establishment of a communicative coupling between the first medical device and the at least one auxiliary device. The second playback interface may be configured to capture user input including an instruction for the first medical device. The at least one second processor may be configured to provide the instruction to the first medical device via the second communications module. The at least one first processor may be configured to receive the instruction via the first communications module, and control the first playback interface based on the received instruction. The instruction may include at least one selected data type to display at the first playback interface. The at least one selected data type may include one of ventilation and/or respiration data, cardiac data, and cardiopulmonary resuscitation data. The ventilation and/or respiration data may include one or more of capnography data and pulse oximetry data and wherein the cardiac data may include electrocardiogram data. The instruction may include a modification of a visual representation of the first patient data at the first playback interface. The instruction may include user feedback. The selective display of the first playback interface may include the at least one first processor being configured to implement a display mode for the at least one first output device selected from a plurality of available display modes including an operational interface only mode, a playback interface only mode, and a combined operational/playback mode. The combined operational/playback mode may enable a simultaneous display on the at least one first display screen of the first operational interface and the first playback interface. One of the first operational interface and the first playback interface may occupy a smaller area on the at least one first display screen than the other of the first operational interface and the first playback interface. The second playback interface may be configured to capture a user input including an instruction indicative of which of the first operational interface and the first playback interface may occupy the smaller area on the at least one first display screen. The at least one second processor may be configured to provide the instruction to the first medical device via the second communications module. The at least one first processor may be configured to control the at least one first display screen based on the instruction. The one or more first patient interface devices may include at least one of one or more therapy delivery components and one or more sensors. The one or more sensors may include one or more a chest compression sensor, ventilation and/or respiration sensors, and cardiac sensing electrodes. The ventilation and/or respiration sensors may include one or more of spirometry sensors, flow sensors, oxygen sensors, carbon dioxide sensors, pulse oximetry sensors, capnography sensors, impedance sensors, and combinations thereof. The one or more therapy delivery components may include electrotherapy electrodes. The at least one auxiliary device may be configured to couple to one or more second patient interface devices including one or more sensors. The at least one second processor may be configured to receive signals indicative of second patient data from the one or more second patient interface devices, and control the at least one second display screen to provide the second patient data as a second operational interface. The one or more second patient interface devices may include one or more therapy delivery components. The first operational interface may be configured to provide a real-time portion of the first patient data. The first playback interface and the second playback interface may be configured to provide the real-time portion of the first patient data and a historical portion of the first patient data. The first patient data may include a plurality of time stamps. The real-time portion of the first patient data may correspond to time stamps of the plurality of time stamps that may be within a threshold time interval from a current time. The historical portion of the first patient data may correspond to time stamps of the plurality of time stamps that may be greater than the threshold time interval from the current time and less or equal to a time difference between the current time and a start time of data collection for a case by the first medical device. The first patient data may include one or more of physiological data and chest compression data. The physiological data may include one or more of an electrocardiogram (ECG), blood pressure, heart rate, respiration rate, heart sounds, lung sounds, respiration sounds, end tidal carbon dioxide, saturation of muscle oxygen ($SMO_2$), oxygen saturation, cerebral blood flow, electroencephalogram (EEG) signals, brain oxygen level, tissue pH, tissue fluid levels, ultrasound images of the patient's heart, near-infrared reflectance spectroscopy data, pneumography data, and cardiography data. The chest compression data may include one or more of displacement data, velocity data, release velocity data, acceleration data, force data, compression rate data, dwell time data, hold time data, blood pressure data, and blood flow data. The first medical device may include a near field communications tag configured to establish communications between the first medical device and the at least one auxiliary device in response to a proximate location of the at least one auxiliary device relative to the first medical device. The first playback interface and the second playback interface may include a data display window configured to provide a visual representation of the first patient data, an interactive timeline configured to capture first user input indicative of a time interval selection for the visual representation of the first patient data, and a media navigation bar configured to capture second user input indicative of data display parameters and to control the visual representation of the first patient data based on the second user input. The visual representation of the first patient data may include one or more of waveforms, time trends, and discrete physiological measurements for one or more of cardiac parameters and ventilation and/or respiration parameters. The visual representation of the first patient data may include one or more of a textual, numerical, and graphical representation of cardiopulmonary resuscitation (CPR) performance data. The CPR performance data may include one or more of a compression depth, a compression rate, a chest release indicator, a perfusion performance indicator, a CPR time indicator, blood pressure data, and blood flow data. The interactive timeline may include a first time interval selector configured to indicate a start time of the visual representation of the first patient data, and a second time interval selector configured to indicate an end time of the visual representation of the first patient data. The first time interval selector and the second time interval selector may be configured to move along the interactive timeline in response to user input. The interactive timeline may include one or more visual event indicators and may be configured to capture a user selection of at least one visual event indicator of the one or more visual event indicators. The data display window may be configured to provide the visual representation of the first patient data that may correspond to the selected at least one visual event indicator. The interactive timeline may be configured to provide a data preview pop-up window in response to a touchscreen gesture associated with an on-screen cursor. The data preview pop-up window may be configured to provide a visual representation of at least a portion of the first patient data that may correspond to a time associated with a position of the on-screen cursor along the interactive timeline. The data preview pop-up window may provide one or more of an ECG waveform, CPR performance data, physiological waveforms, discrete physiological measurements, device settings, and device actions. The media navigation bar may include user interactive data display controls configured to enable a user to control playback of the first patient data. The user interactive data display controls may include one or more of a rewind control, a play control, a stop control, a pause control, and a fast forward control, a skip back control, and skip forward control. The first playback interface and the second playback interface may include a playback speed selection control configured to adjust a playback speed for the first patient data visually represented in the data display window. The first playback interface and the second playback interface may be configured automatically adjust the playback speed to provide a historical portion of the first patient data at a speed determined by the playback speed selection control and provide a real-time portion of the first patient data at a speed that matches a data display speed for the first operational interface. The first playback interface and the second playback interface may include an event search function configured to provide a user-selectable list of events on an interactive menu in response to a user activation of the event search function. The first playback interface and the second playback interface may be configured to highlight visual indicators on the interactive timeline in response to a user selection of an event from the user-selectable list of events. The first playback interface and the second playback interface may include a medical condition selection control configured to enable a user selection of a medical condition from an interactive menu, and determine one or more settings for data display based on the user selection of the medical condition. The first playback interface and the second playback interface may include a data preview area.

An example of a system for review of clinical data in a playback mode according to the disclosure includes at least one display screen associated with a playback interface host device, one or more patient interface devices, a memory, and a processor coupled to the one or more patient interface devices, the memory, and the at least one display screen and configured to receive signals from the one or more patient interface devices that may be indicative of patient data, generate a visual representation of the patient data, and control the at least one display screen to selectively display a playback interface, wherein the playback interface may include the visual representation of the patient data.

Implementations of such a system may include one or more of the following features. The selective display of the playback interface may include the processor being configured to implement a display mode for the at least one display screen selected from a plurality of display modes including an operational interface only mode that excludes the playback interface, a playback interface only mode, and a combined operational/playback mode. The processor may be configured to disallow selection of one or more of the plurality of display modes based on a status of the one or more patient interface devices. The processor may be configured to disallow an automated selection of the one or more of the plurality of display modes. The processor may be configured to disallow a user selection of the one or more of the plurality of display modes. The one or more patient interface devices may include one or more therapy delivery components. The status of the one or more patient interface devices may include an indication of whether the playback interface host device may be currently delivering therapy to a patient via the one or more therapy delivery components. The one or more patient interface devices may include one or more sensors. The status of the one or more patient interface devices may include an indication of whether the one or more sensors may be currently coupled to a patient to provide sensor signals to the playback interface host device. The playback interface host device may be configured to capture the user input indicative of a user selected display mode. The processor may be configured to implement the display mode based on the user input. The processor may be configured to generate the visual representation of the patient data from non-image format data. The processor may be configured to generate the visual representation of the patient data in real-time. The playback interface may include a data display window configured to provide a visual representation of the at least a portion of the patient data, an interactive timeline configured to capture first user input indicative of a time interval selection for the visual representation of the at least a portion of the patient data, and a media navigation bar configured to capture second user input indicative of data display parameters, and control the visual representation of the at least a portion of the patient data based on the second user input. The visual representation of the at least a portion of the patient data may include one or more of waveforms, time trends, and discrete physiological measurements. The patient data may include one or more of cardiac parameters and ventilation and/or respiration parameters. The waveforms may include electrocardiogram (ECG) waveforms. The waveforms may include one or more of a pulse oximetry waveform and a capnography waveform. The discrete physiological measurements may include one or more of heart rate, blood pressure, breathing rate, temperature, oxygen saturation, and end tidal carbon dioxide. The visual representation of the at least a portion of the patient data may include one or more of a textual, numerical, and graphical representation of cardiopulmonary resuscitation (CPR) performance data. The CPR performance data may include one or more of a compression depth, a compression rate, a chest release indicator, a perfusion performance indicator, a CPR time indicator, blood flow data, and blood pressure data. The time interval selection may include a start time for the visual representation of the at least a portion of the patient data and an end time for the visual representation of the at least a portion of the patient data. The interactive timeline may include a first time interval selector configured to indicate the start time of the visual representation of the at least a portion of the patient data and a second time interval selector configured to indicate the end time of the visual representation of the at least a portion of the patient data. The first time interval selector and the second time interval selector may be configured to move along the interactive timeline in response to user input. The interactive timeline may be configured to capture a two-finger touchscreen gesture. A position of a first finger of the gesture may correspond to the start time of the time interval selection and a position of a second finger of the gesture may correspond to the end time of the time interval selection. The start time and the end time may each correspond to a respective time prior to a current time. The start time may correspond to a time prior to a current time and the end time may correspond to the current time. The visual representation may include a looped playback of the at least a portion of the patient data over a sequence of times between and including the start time and the end time. The playback interface may include a loop control configured to capture user input indicative of a number of repetitions for the looped playback. The interactive timeline may include one or more visual event indicators. The one or more visual event indicators may include one or more icons. Each icon may be at a position along the interactive timeline that may correspond to a time of an event represented by the icon. The one or more visual event indicators may correspond to one or more medical events. The one or more medical events may include one or more of received treatment and physiological events, the received treatment including at least one of cardiopulmonary resuscitation, drug delivery, electrotherapy, and ventilation and/or respiration and the physiological events including at least one of a physiological parameter measurement and a physiological parameter observation. The one or more visual event indicators may correspond to one or more medical device events. The one or more medical device events may include a heart rhythm analysis, delivery of electrotherapy, and a low battery condition. The interactive timeline may be configured to capture a user selection of at least one visual event indicator of the one or more visual event indicators. At least one of a start time and an end time of the time interval selection may correspond to a time associated with the selected at least one visual event indicator. The interactive timeline may be configured to capture a user selection of a first visual event indicator and a second visual event indicator wherein a time associated with the first visual event indicator may correspond to a start time of the time interval selection and a time associated with the second visual event indicator may correspond to an end time of the time interval selection. A start time of the time interval selection may correspond to a time that may be a predetermined time interval prior to the time associated with the selected at least one visual event indicator. An end time of the time interval selection may correspond to a time that may be a predetermined time interval subsequent to the time associated with the selected at least one visual event indicator. The data display window may be configured to provide the visual representation of the at least a portion of the patient data that may correspond to the selected at least one visual event indicator. The selected at least one visual event indicator may correspond to a shock event and the visual representation of the patient data may correspond to ECG data. The selected at least one visual event indicator may correspond to a drug administration and the visual representation of the patient data may correspond to physiological data associated with an expected patient response to the drug administration. The interactive timeline may include an on-screen cursor configured to move along the interactive timeline in response to user input wherein a position of the on-screen cursor may correspond to a user-selected position along the interactive timeline. The user input may include input captured by a touchscreen associated with the playback interface. The interactive timeline may be configured to provide a data preview pop-up window in response to a touchscreen gesture associated with the on-screen cursor. The touchscreen gesture may include at least one of a press and at least one tap. The data preview pop-up window may be configured to provide a visual representation of the patient data that may correspond to a time associated with a position of the on-screen cursor along the interactive timeline. The data may include one or more of an ECG waveform, CPR performance data, physiological waveforms, discrete physiological measurements, device settings, and device actions. The interactive timeline may include a playback pointer configured to dynamically indicate a time associated with the visual representation of the data at the data display window. The playback pointer may be configured automatically move along the interactive timeline in synchronously with the visual representation of the data. The data display window may include a playback position indicator configured to display a numeric representation of the time associated with the playback pointer. The media navigation bar may include user interactive data display controls that may be configured to enable a user to control playback of data at the playback interface. The user interactive data display controls may include one or more of a rewind control, a play control, a stop control, a pause control, and a fast forward control, a skip back control, and skip forward control. The skip back control and the skip forward control may be configured to cause the playback interface to provide data according to a user selected sequence. The skip back control and the skip forward control may be configured to enable the user to a select a time for data playback corresponding to a visual event indicator. The playback interface may include a playback speed selection control configured to adjust a playback speed for data in the data display window. The playback interface may be configured to automatically adjust the playback speed for data in the data display window so that the playback interface may provide historical data at a speed determined by the playback speed selection control and may provide real-time data at a default speed. The playback interface may include an event search function. The playback interface may be configured to provide a user-selectable list of events on an interactive menu in response to a user activation of the event search function. The user-selectable list of events may include events in chronological order. The user-selectable list of events may include events sorted by type of event. The playback interface may be configured to highlight visual indicators on the interactive timeline in response to a user selection of an event from the user-selectable list of events. The playback interface may include a medical condition selection control. The medical condition selection control may be configured to enable user selection of a medical condition from an interactive menu of the playback interface. The playback interface may be configured to determine one or more settings for data display at the playback interface based on the user selection of the medical condition. The one or more settings may include one or more of a playback interval, a playback interval relative to a visual event indicator on the interactive timeline, a playback speed, or a number of repetitions of data display for looped playback. The playback interface may include a data preview area. The display may include a touchscreen and the playback interface may be configured to provide data from the data display window in the data preview area in response to a drag and drop touchscreen operation. The display may include a pressure sensitive touchscreen and the playback interface may be configured to provide data from the data display window in the data preview area in response to pressure applied to the data display window. The data preview area may include a plurality of data preview windows. Each data preview window of the plurality of data preview windows may include a time display corresponding to a time on the interactive timeline associated with the data in the respective data preview window. The data preview area may be configured to provide the plurality of data preview windows in a chronological order within the data preview area based on a time interval associated with the data in each data preview window of the plurality of data preview windows. The playback interface may be configured to capture an annotation for data in the data preview area. The playback interface may be configured to capture the annotation via a text input to the playback interface. The playback interface may be configured to capture the annotation via an audio input to the playback interface. The playback interface host device may include a computing device. The computing device may include a computer tablet. The playback interface host device may include a medical device. The medical device may include one of a therapeutic medical device and a patient monitor. The therapeutic medical device may include a defibrillator, a defibrillator/patient monitor, or a modular defibrillator/patient monitor. The one or more patient interface devices may include therapy electrodes. The patient data may include one or more of electrocardiogram (ECG) data and transthoracic impedance data. The one or more patient interface devices may include a chest compression monitor and wherein the patient data may include chest compression parameters. The one or more patient interface devices may include one or more of ventilation and/or respiration sensors and cardiac sensing electrodes. The ventilation and/or respiration sensors may include one or more of spirometry sensors, flow sensors, oxygen sensors, carbon dioxide sensors, pulse oximetry sensors, capnography sensors, impedance sensors, and combinations thereof. The patient data may include one or more of physiological data and chest compression data. The physiological data may include one or more of an electrocardiogram (ECG), blood pressure, heart rate, respiration rate, heart sounds, lung sounds, respiration sounds, end tidal carbon dioxide, saturation of muscle oxygen (SMO2), oxygen saturation, cerebral blood flow, electroencephalogram (EEG) signals, brain oxygen level, tissue pH, tissue fluid levels, ultrasound images of the patient's heart, near-infrared reflectance spectroscopy data, pneumography data, and cardiography data. The chest compression data may include one or more of displacement data, velocity data, release velocity data, acceleration data, force data, compression rate data, dwell time data, hold time data, blood pressure data, and blood flow data. The at least one display screen may include a touchscreen. The touchscreen may include a pressure-sensitive touchscreen.

Other capabilities may be provided and not every implementation according to the disclosure must provide any, let alone all, of the capabilities discussed. Further, it may be possible for an effect noted above to be achieved by means other than that noted and a noted item/technique may not necessarily yield the noted effect.

BRIEF DESCRIPTION OF THE DRAWINGS

Various aspects of the disclosure are discussed below with reference to the accompanying figures, which are not intended to be drawn to scale. The figures are included to provide an illustration and a further understanding of various examples, and are incorporated in and constitute a part of this specification, but are not intended to limit the scope of the disclosure. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure. A quantity of each component in a particular figure is an example only and other quantities of each, or any, component could be used.

DETAILED DESCRIPTION

Figure 1A:
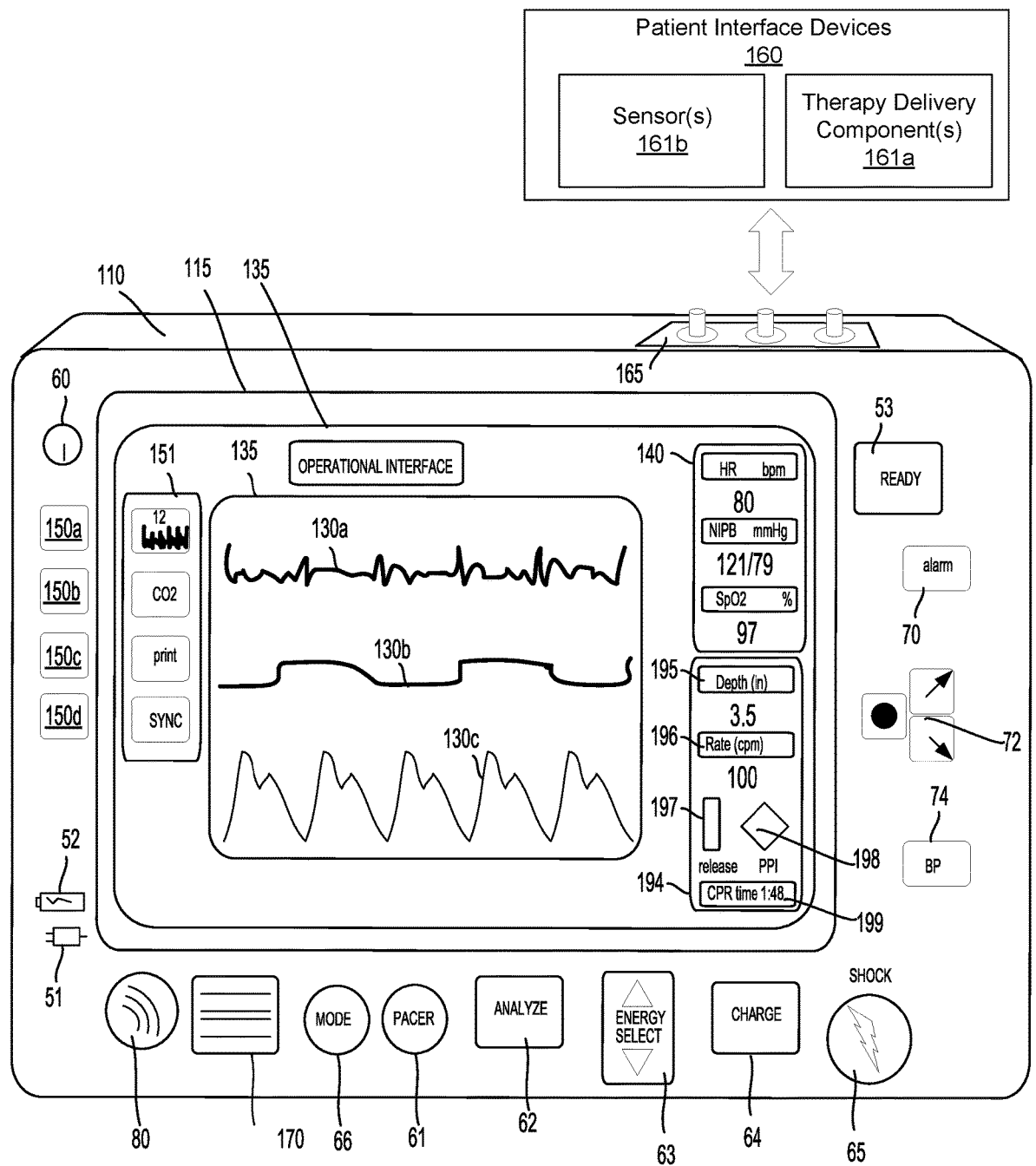
FIG. 1A shows an example of a medical device with an operational interface.

During a medical event, a medical device may provide medical therapy to a patient and/or may monitor the patient. The medical device may be one physical device (e.g., a single housing) or may be multiple physical devices (e.g., modular physical devices with two or more separate housings) configured to communicatively and/or operatively couple to one another. For example, the medical device may be a patient monitor, a therapeutic medical device (e.g., a defibrillator, an automated compression device, a ventilator, etc.), a therapeutic medical device/patient monitor, or a modular therapeutic medical device/patient monitor. The medical device may include and/or be configured to couple to one or more patient interface devices. The patient interface devices may include one or more therapy delivery components, one or more sensors, and combined therapy delivery/sensing components such as defibrillation electrodes configured to sense and monitor a patient's electrocardiogram (ECG) and to deliver electrotherapy. The medical device may collect patient data via the one or more patient interface devices. The patient data may include treatment data, sensor data, and/or combinations thereof. The treatment data may correspond to data collected during or in conjunction with therapy delivery. For example, ECG data collected while defibrillation electrodes are coupled to the patient may be treatment data as this data is collected in conjunction with a possible delivery of electrotherapy. An evaluation of the ECG may be necessary in order to determine if electrotherapy is necessary and to enable delivery of the electrotherapy by the defibrillator. The sensor data may correspond to data collected by a medical device that is not configured to deliver therapy (e.g., a patient monitor) and/or by a medical device that is configured to deliver therapy (e.g., a therapeutic medical device). For example, the patient monitor may collect ECG data via sensing electrodes and may not be configured to deliver electrotherapy to the patient. As another example, the defibrillator may be coupled to the patient via the defibrillation and/or sensing electrodes and may collect ECG data via these electrodes. If the ECG evaluation determines that electrotherapy is recommended, the defibrillator may be utilized to deliver the electrotherapy via the defibrillation electrodes. In an implementation, the defibrillator may be used as a patient monitor with sensors including the electrodes and/or other physiological sensors. The patient data may include physiological sensor data. Additionally or alternatively, the patient data may include clinical performance data such as chest compression parameters, respiration parameters, blood flow and/or blood pressure parameters, etc. In an implementation, the chest compression parameters may include the blood flow and/or the blood pressure parameters. Additionally or alternatively, the patient data may include patient demographic data (e.g., name, age, gender, address, insurance, medical provider, etc.), patient height, patient weight, chest anterior/posterior measurement, diagnostic data, stored event markers of clinical interventions and/or other types of event markers, historical patient health information, medication, drug use, and/or prescription information, clinical performance information (e.g., chest compression measurements, chest impedance measurements), etc. In an implementation, the patient data may include emergency services data such as, for example, but not limited to a time of cardiac arrest and/or other emergency event, a time of a 911 call, a time of dispatch, and/or other emergency dispatch and/or electronic patient care record data. In an implementation, event markers may come from a plurality of medical devices communicatively coupled to the playback interface.

The medical device may provide the medical therapy via the one or more therapy delivery component(s). The medical device may include the one or more therapy delivery component(s) and/or may be configured to couple to the one or more therapy delivery component(s) in order to provide medical therapy to the patient. The therapy delivery component(s) may be configured to couple to the patient. For example, the therapy delivery components may be defibrillation electrodes. The caregiver may attach the defibrillation electrodes to the patient and the defibrillator or defibrillator/patient monitor may provide electrotherapy to the patient via the defibrillation electrodes. As another example, the therapy delivery components may be one or more belts or a piston that may provide chest compression therapy to the patient as components of the automated compression device, or may be a compression monitor that a caregiver may place on the chest of a patient to sense chest compression parameters during the application of manual chest compressions. As a further example, the therapy delivery components may be breathing tubes and/or a mask. Ventilation (e.g., mechanical ventilation and/or manual ventilation) may deliver air and/or provide other ventilation and/or respiration therapy to the patient via the breathing tubes and/or the mask. These examples are not limiting of the disclosure as other types of medical devices, therapy delivery components, sensors, and therapy are within the scope of the disclosure.

The medical device may monitor the patient via the one or more sensors. The one or more sensors may generate signals indicative of physiological parameters of the patient. For example, the physiological parameters may include one or more of at least one vital sign, an ECG, blood pressure, heart rate, respiration rate, heart sounds, lung sounds, respiration sounds, end tidal carbon dioxide, saturation of muscle oxygen ($SMO_2$), oxygen saturation (e.g., $SpO_2$ and/or $PaO_2$), cerebral blood flow, electroencephalogram (EEG) signals, brain oxygen level, tissue pH, tissue fluid levels, physical parameters as determined via ultrasound images, parameters determined via near-infrared reflectance spectroscopy, pneumography, and/or cardiography, etc. Additionally or alternatively the one or more sensors may generate signals indicative of resuscitation/care data for the patient. For example, the resuscitation/care data may include chest compression parameters, ventilation and/or respiration parameters, drug delivery parameters, fluid delivery parameters, etc. The ventilation parameters may be manual ventilation parameters and/or mechanical ventilation parameters.

In an implementation, the therapy delivery components may include and/or function as sensors and generate signals indicative of physiological and/or resuscitation parameters. For example, the defibrillation electrodes may be configured as cardiac sensing electrodes as well as electrotherapy delivery devices. As another example, a therapeutic cooling device may be an intravenous cooling device. Such a cooling device may include an intravenous (IV) device as a therapy delivery component configured to deliver cooling therapy and sense the patient's temperature. For example, the IV device may be a catheter that includes saline balloons configured to adjust the patient's temperature via circulation of temperature controlled saline solution. In addition, the catheter may include a temperature probe configured to sense the patient's temperature. As a further example, an IV device may provide therapy via drug delivery and/or fluid management. The IV device may also monitor and/or enable monitoring of a patient via blood sampling and/or venous pressure monitoring (e.g., central venous pressure (CVP) monitoring).

The medical device may receive the signals generated by the one or more sensors and/or the one or more therapy delivery components. The medical device may include one or more processors, memory, and associated circuitry configured to receive, process, and analyze these signals to generate and/or determine patient data. During therapy delivery, a user of a medical device may view and/or review the patient data via a display or other output device of the medical device. In various implementations, the user may be a caregiver such as a first responder, a paramedic, a physician, a rescue worker, etc. For example, the output device may be a display, a speaker, a haptic device, etc. The output device may be an input/output device configured to capture user input in addition to providing information for the user.

The output device may provide an operational interface that provides the patient data as operational information. The operational information may include, for example, medical care delivery parameters (e.g., performance parameters), medical device operational parameters and settings, physiological information for the patient, etc. For example, on the defibrillator, the patient monitor coupled to the defibrillator, or a defibrillator/monitor, the operational information may include chest compression rate and depth as delivery parameters, shock energy as an operational parameter or setting, and an electrocardiogram (ECG) as physiological information. The operational interface may display and/or otherwise provide the operational information in real-time as it is captured, generated, and/or collected by the medical device during an ongoing medical event. Thus the user may view the patient data in real-time in order to effectively administer care to the patient.

It may be of benefit for the user of the medical device to review at least a portion of the operational information in a playback mode. The review in the playback mode may replay or redisplay treatment information at a playback interface. The playback interface may enable this review during the ongoing medical event and while the medical device is still administering therapy and/or collecting patient data from the patient. Thus, data playback may not require any downtime in operation of the medical device. This review may include review of patient data from time periods that include a current time. Alternatively, this review may be a historical review that includes time periods prior to the current time. Thus, the playback interface may enable a review of the patient data in real-time and/or as historical data. Further, input to the playback interface may augment patient data collected by the medical device and/or displayed at the playback interface. For example, in various implementations, the playback interface may enable review of patient data such as heart rate, blood pressure, etc. and/or physiological waveforms such as, for example, an electrocardiogram and/or CPR data such as, for example, compression depth, compression rate, etc. These types of data are examples only and not limiting of the disclosure and are discussed in further detail below along with various features of the playback interface.

It may be of benefit to the user to access this playback interface at the medical device (e.g., the device delivering therapy to the patient and/or monitoring the patient) and/or at an auxiliary device. As such, one or more of the medical device and the auxiliary device may be a playback interface host device. The auxiliary device may be communicatively coupled to the medical device and may be located proximate to or remote from the medical device. The auxiliary device may be a medical device or a computing device. The auxiliary device may receive the patient data from the medical device for display at the playback interface hosted by the auxiliary device. The auxiliary device may deliver and/or be configured to deliver therapy to the patient. Additionally or alternatively, the auxiliary device may collect patient data from the patient via one or more sensors. For example, the auxiliary device may be a computer tablet, a server, a laptop, a mobile communications device, a patient monitor, a therapeutic medical device (e.g., a defibrillator, an automated compression device, a ventilator, etc.), a therapeutic medical device/patient monitor, or a modular therapeutic medical device/patient monitor. These types of medical and auxiliary devices are examples only and other types and combinations of medical devices and/or auxiliary devices are within the scope of the disclosure.

The ability of the playback interface host device (e.g., the medical device and/or the auxiliary device) to provide the playback interface during the ongoing medical event may provide the advantage of improving the efficacy of care provided to the patient as a result of the data review with the playback interface. For example, the patient may report chest pain and the caregiver may couple the defibrillation electrodes of a defibrillator to the patient in anticipation of a need to provide electrotherapy. The caregiver may also administer a drug such as aspirin or nitroglycerine. The defibrillator may collect an ECG waveform over a time period spanning the drug administration. Without interruption of on-going care and/or real-time monitoring, the caregiver may playback and review the ECG over the time period spanning the drug administration to see the effect, if any, of the drug administration on the ECG. This information may inform an evaluation of whether the chest pain indicates a cardiac condition and/or the efficacy of the particular drug and/or the particular drug dosage. As another example, the caregiver may be treating the patient for cardiac arrest and may playback the ECG immediately pre- and post-defibrillation shock from an earlier defibrillation shock to determine what the presenting and post shock rhythms were and adjust the defibrillation energy of the upcoming defibrillation based on the effect incurred on the ECG from a previous defibrillation shock. As a further example, the patient may report and/or present with breathing difficulty. The defibrillator or defibrillator/monitor may collect a capnography and/or spirometry waveform. The collected waveform may span a time period during which an asthma-type inhaler was provided to the patient. As in the previous example, without interruption of ongoing care and/or real-time monitoring, the caregiver may playback and review the waveform over the time period spanning the inhaler delivery. If the waveform indicates a clear airway in response to the inhaler, the caregiver may diagnose and/or treat the patient for asthma. However, if the waveform does not indicate a clear airway in response to the inhaler, the caregiver may diagnose and/or treat the patient for COPD. In both of these examples, the playback interface may enable the caregiver to look back in time to see what a particular waveform looked like before an intervention in order to better evaluate the patient condition after the intervention. As such, the data review enabled by the playback interface may improve an evaluation of the appropriateness and/or effectiveness of treatments provided. In particular, by evaluating these treatments during the medical event, the treatments may be modified and adjusted in real-time during the ongoing medical event.

The benefits of the playback interface may be further enhanced if the medical device configured to deliver therapy via the therapy delivery components provides the playback interface along with the operational interface. Such a medical device may provide both the operational interface and the playback interface during ongoing therapy which may inform a treatment decision and/or enable an evaluation of an administered treatment in real-time without disruption of the ongoing therapy. For example, such an arrangement may eliminate or reduce the need for the caregiver to provide extra equipment to display the playback interface. This may be of particular use in an emergency care scenario where equipment may be transported to the scene of the patient and timely delivery of care may be critical. Reducing the number of items of equipment may ease transportation of the equipment and reduce time and cost associated with care. As another example, such an arrangement may allow one caregiver to review the playback information without disrupting the monitoring of the operational information. For instance, the medical device may provide patient data, including, for example, an ECG, as an operational interface. The caregiver may observe the ECG provided as the operational interface to monitor a current state of the patient. Additionally, the caregiver may review the ECG over time at the playback interface to evaluate previous interventions such as drugs. This review may not disrupt the current state monitoring. Even during the playback review, the defibrillator and the caregiver may continue to evaluate the ECG for indications of a shockable arrhythmia and provide electrotherapy without delays due to patient data review. As a further benefit, the simultaneous view of the operational and playback data on one device may more clearly indicate the temporal relationship between the operational and playback data than data displayed on separate devices. This feature where operational and playback data are made readily and simultaneously available may provide additional efficiency and may further improve patient diagnostics and care.

In some medical care scenarios, the medical device that provides both the playback interface and the operational interface may be a second or subsequent device in a sequence of medical devices. The previous medical device may provide patient data to the subsequent medical device. In this case, during and after a patient transition to the second medical device, the caregiver may playback and review the patient data collected by the previous medical device without disruption of ongoing care by the subsequent medical device. Such cooperative data review and/or sharing may improve the efficiency and quality of tiered care that involves patient transitions between medical devices.

As an example of tiered care, the first responders to a cardiac emergency may be a basic life support (BLS) crew. This first tier BLS crew may have an automated external defibrillator (AED) and may be trained to follow rigid EMS care protocols as instructed via the operational interface of the AED. However, the BLS crew may not include personnel trained to evaluate medical data and adjust care beyond these protocols. For example, the BLS crew may strictly follow automated use instructions provided by the AED. As a second or subsequent tier, a medical supervisor and/or an advanced life support (ALS) crew may arrive at the scene to provide further assistance to the BLS crew. The medical supervisor may have the requisite training to evaluate the patient data and adjust care beyond the protocols. If the AED includes the capability of providing the playback interface, the BLS crew may continue to follow the automated AED instructions via the operational interface while the medical supervisor may review and evaluate the patient data at the playback interface. If the AED provides both of these interfaces, the medical supervisor may not have to carry any extra and/or specialized equipment. The medical supervisor may simply arrive at the scene, pull up the playback interface on the AED that is already in use on the patient, review and evaluate the patient data at the playback interface, and advise the BLS crew of care adjustments. The ALS crew may arrive at the patient scene with a more advanced defibrillator and/or patient monitor which may allow for more sophisticated and flexible medical evaluation and care than the AED. For instance, the more advanced defibrillator and/or patient monitor may provide additional monitoring functions such as pulse oximetry and capnography or additional therapies such as cardiac pacing or synchronized cardioversion. As another example, an emergency department physician may review playback information on a remote device that provides the playback interface. The physician may provide information to the caregivers en route to the hospital and/or may prepare specific treatments and/or tests to administer to the patient upon arrival based on this playback review. In an implementation, one or more of the first or subsequent medical devices may enable both AED and manual operation modes. Upon arrival at the scene and/or en route to the scene, the AED and the advanced defibrillator and/or patient monitor may communicatively couple to one another and share collected patient data. The ALS crew may review real-time and/or historical patient data collected by the AED at a playback interface provided by the advanced defibrillator and/or patient monitor. The advanced defibrillator and/or patient monitor and/or the ALS team may provide care instructions or other information to the AED and/or the BLS team based on this review. Furthermore, upon arrival at the scene, the ALS crew may transition the patient from the AED to the advanced defibrillator and/or patient monitor. The playback interface at the advanced defibrillator and/or patient monitor may enable review of data collected by the advanced defibrillator and/or patient monitor during ongoing therapy delivery.

Figure 11:
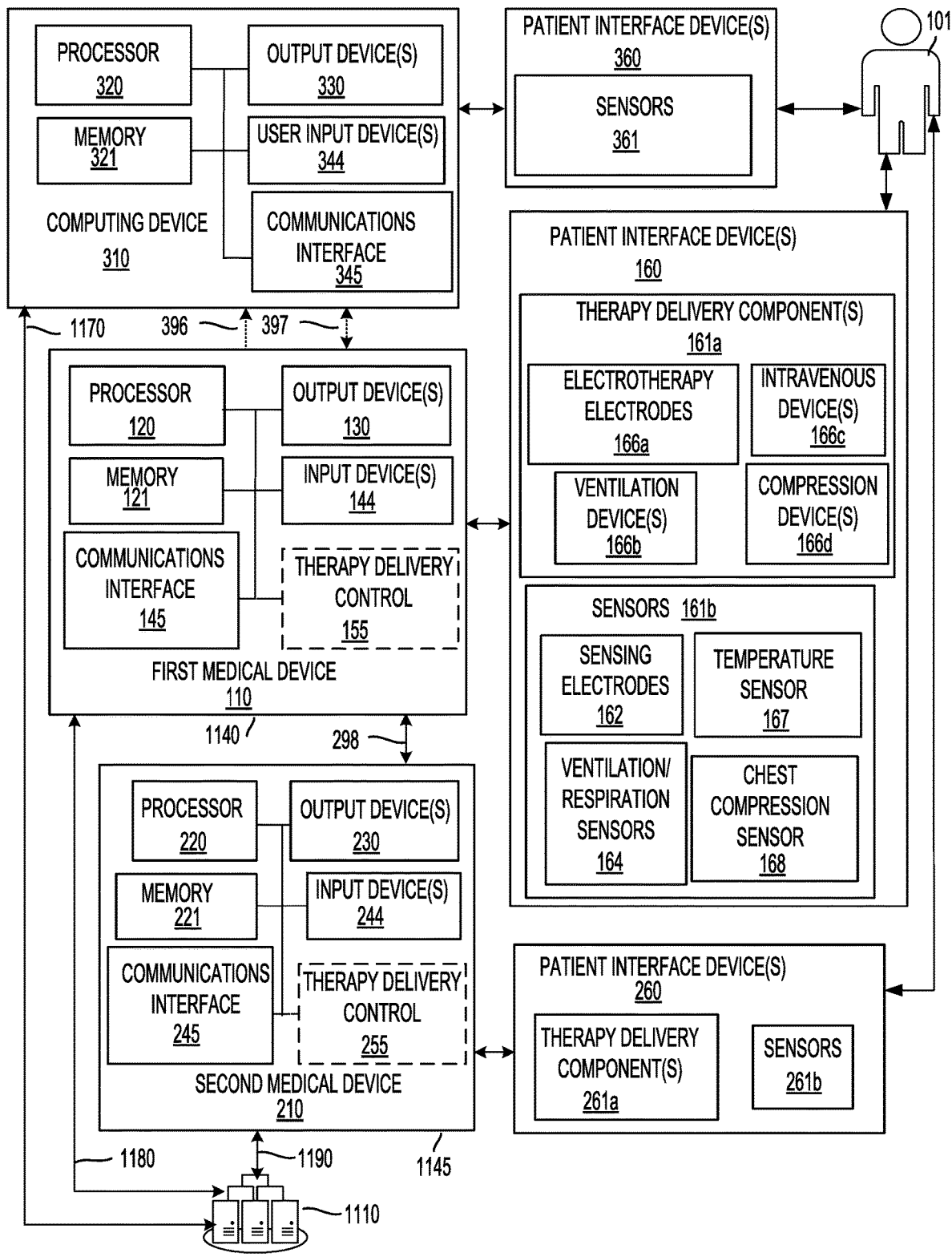
FIG. 11 shows examples of components of various devices discussed with regard to FIGS. 1A-10C.
Figure 12:
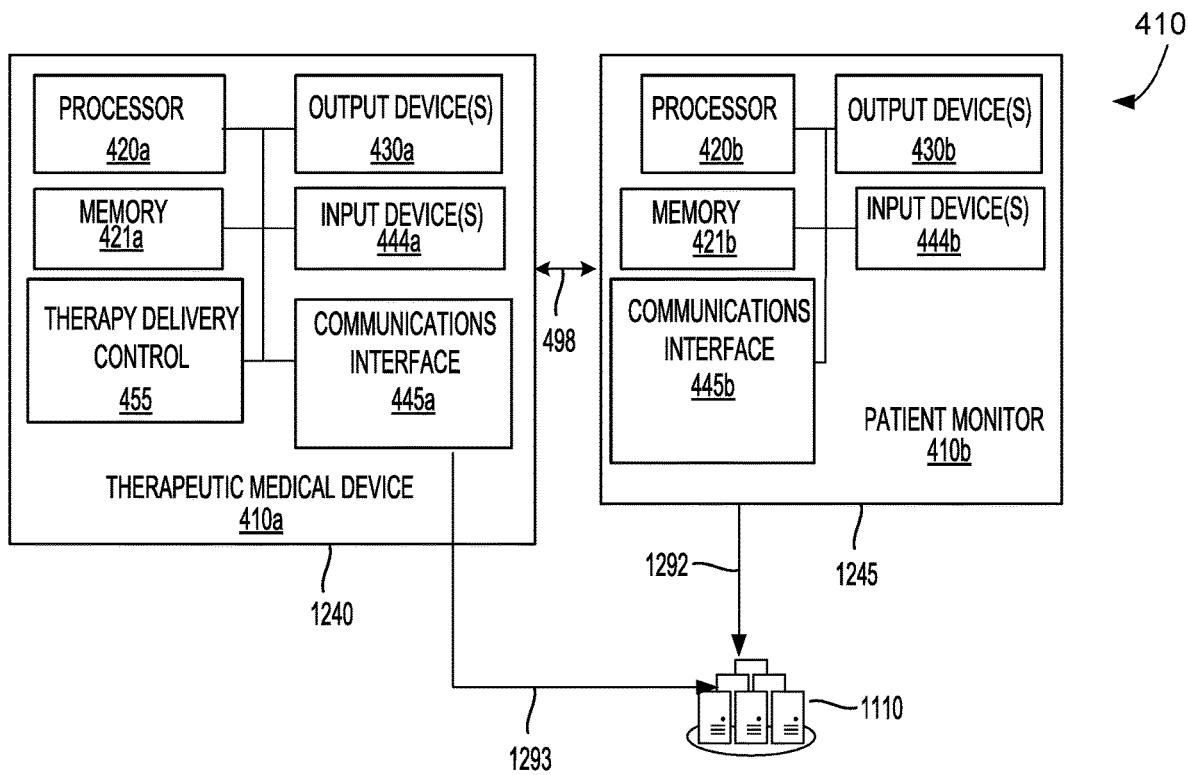
FIG. 12 shows examples of components of a modular therapeutic medical device/patient monitor.

Referring to FIG. 1A, an example of a medical device with an operational interface is shown. The medical device 110 is shown in FIG. 1A as a patient monitor/defibrillator. This configuration of the medical device 110 is an example only and not limiting of the disclosure. In various implementations, the medical device 110 may be a defibrillator, patient monitor, defibrillator/monitor, an automated compression device, a therapeutic cooling device, an extracorporeal membrane oxygenation (ECMO) device, a ventilation device, combinations thereof, or another type of medical device configured to couple to one or more therapy delivery components to provide therapy to the patient. In an implementation, the medical device 110 may be an integrated therapy delivery/monitoring device that includes a single housing 1140, as shown in FIG. 11. The single housing 1140 may surround, at least in part, the therapy delivery components and the monitoring components. In an implementation, the medical device 110 may be a modular therapy delivery/monitoring device (e.g., the device 410 as described in further detail below with regard to FIG. 4B) that includes at least a first housing 1240 and a second housing 1245 (e.g., as shown in FIG. 12).

Referring further to FIG. 1A, the medical device 110 may include one or more output or input/output devices, for example, a display screen 115. A processor of the medical device 110 (e.g., the processor 120 as shown in FIG. 11) may control the display screen 115 to selectively display the operational interface 135. The operational interface 135 as shown in FIG. 1A is an example only and elements may be rearranged, combined, altered, or deleted. As discussed in further detail below, selective display refers to the ability of the processor to select amongst various available display modes which may include an operational interface only display mode.

The operational interface 135 may provide patient data received by the medical device 110 from the patient interface device(s) 160 (e.g., the therapy delivery component(s) 161*a* and/or from the sensor(s) 161*b*). For example, the medical device 110 may be configured to couple to the patient interface device(s) 160 via the one or more connection ports 165. The operational interface 135 may provide the patient data in real-time as the signals are received and processed by the processor 120 of the medical device 110. The patient interface device(s) 160 and the patient data are described briefly here and also described in further detail with regard to FIG. 11.

The therapy delivery component(s) 161*a* are configured to deliver therapy to the patient and may be configured to couple to the patient. For example, the therapy delivery component(s) 161*a* may include one or more of electrotherapy electrodes including defibrillation electrodes and/or pacing electrodes, chest compression devices, ventilation devices, drug delivery devices, etc. In addition to delivering therapy to the patient, the therapy delivery component(s) 161*a* may include, be coupled to, and/or function as sensors and provide signals indicative of sensor data (e.g., first sensor data) to the medical device 110. For example, the therapy delivery component(s) 161*a* may be defibrillation and/or pacing electrodes and may provide signals indicative of transthoracic impedance, electrocardiogram (ECG), heart rate and/or other physiological parameters.

The sensor(s) 161*b* are configured to provide signals indicative of sensor data (e.g., second sensor data) to the medical device 110. The sensor(s) 161*b* may be configured to couple to the patient. For example, the sensor(s) 161*b* may include cardiac sensing electrodes, a chest compression sensor, and/or ventilation and/or respiration sensors.

The medical device 110 may be configured to receive the sensor signals (e.g., from the therapy delivery component(s) 161*a* and/or the sensor(s) 161*b*) indicative of patient data for the patient and configured to process the sensor signals to determine and collect the patient data. The patient data may include patient data which may characterize a status and/or condition of the patient (e.g., physiological data such as ECG, heart rate, pulse oximetry, non-invasive hemoglobin parameters, capnography, oxygen and carbon dioxide concentrations in the airway, invasive and non-invasive blood pressures, tissue pH, tissue oxygenation, near infra-red spectroscopy, lactate, glucose and/or other laboratory measures which may be point-of-care laboratory measures, images and/or video from examination devices (e.g., ultrasound, laryngoscope, etc.), temperature, etc.). Additionally or alternatively, the patient data may characterize the delivery of therapy (e.g., chest compression data such as compression depth, compression rate, etc.) and/or the patient data may characterize a status and/or condition of the medical equipment used to treat the patient (e.g., device data such as shock time, shock duration, attachment of electrodes, power-on, etc.). In an implementation, the patient data may include information from a wearable medical device such as a defibrillation vest.

In addition to the display screen 115, the medical device 110 may include one or more other output devices such as, for example, a speaker 170. The processor 120 may be configured to control the speaker 170 to provide audible instructions, a metronome (e.g., a chest compression metronome), feedback, and/or physiological information for a user of the medical device 110. The medical device 110 may further include device status indicators and/or device operation controls. For example, device status indicators may include a power-on indicator 51, a battery charge indicator 52, and/or a device ready indicator 53. The device operation controls may include a power-on control 60, a pacer mode control 61, a heart rhythm analyze control 62, a defibrillation energy selection control 63, a charge control 64, a shock delivery control 65, an alarm control 70, one or more display navigation controls 72, and a sensor control 74. Activation of the sensor control 74 may cause an associated patient data sensor to capture patient data and provide the data to the medical device 110. The display screen 115 may provide the captured patient data. For example, activation of the sensor control 74 may cause a blood pressure sensor to measure the patient's blood pressure and may cause the operational interface 135 to display the measured blood pressure in response to activation of the sensor control 74. The medical device 110 may include one or more soft-keys 150*a*, 150*b*, 150*c*, 150*d*, one or more soft-key labels 151, and/or a near-field communications (NFC) tag 80. The NFC tag 80 may enable the medical device 110 to communicatively couple with another device.

Figure 1B:
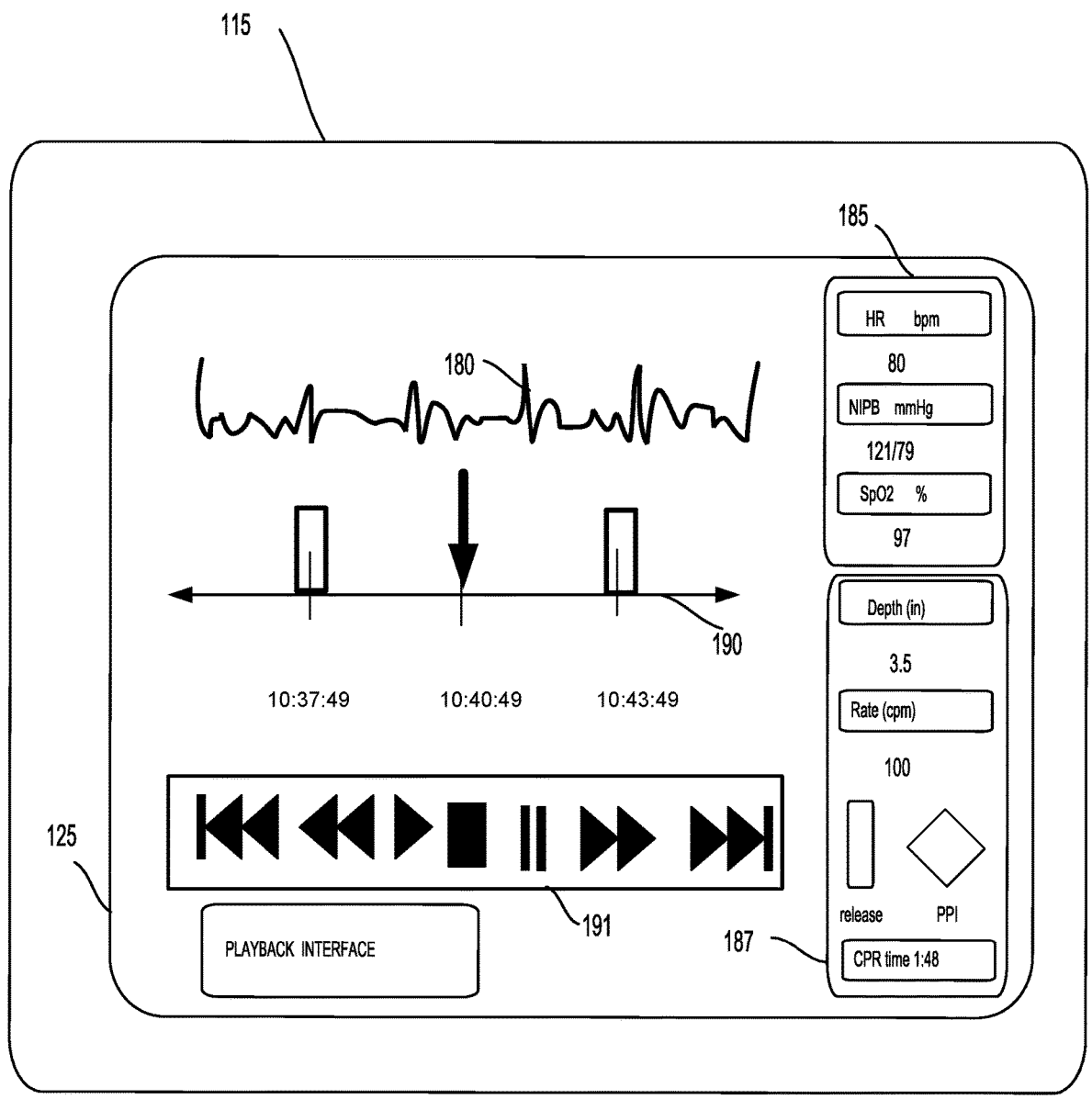
FIG. 1B shows an example of a playback interface with the medical device as the playback interface host device.

Referring to FIG. 1B, an example of a playback interface with the medical device as the playback interface host device is shown. The processor 120 of the medical device 110 may control the display screen 115 to selectively display the playback interface 125. As discussed in further detail below, selective display refers to the ability of the processor to select amongst various available display modes which may include a playback interface only display mode. The playback interface 125 as shown in FIG. 1B is an example only and elements may be rearranged, combined, altered, or deleted. Similarly to the operational interface 135, the playback interface 125 may provide the patient data received by the medical device 110 from the sensor(s) 161*b* and/or from the therapy device(s) 161*a*. However, in addition to the real-time patient data, the playback interface 125 may also provide historical patient data. In an implementation, the playback interface 125 may provide device state information that corresponds to a time associated with patient data.

The playback interface 125 may include various features to enable data review. For example, the playback interface 125 may include visual representations of a physiological waveform/time trend 180 and/or of physiological measurements 185 and/or of CPR performance parameters 187. Additionally, the playback interface may include a user interactive timeline 190 and media navigation bar 191. These and other features of the playback interface 125 are described in more detail below with regard to FIGS. 5-10B.

The user of the playback interface 125 may interact with the playback interface 125 to select time periods of interest and review the patient data corresponding to the selected time periods. These time periods may include the historical data, the real-time data, or combinations thereof as discussed in further detail below with regard to temporal labels in FIGS. 5, 6A, 6B, 7A, and 7B.

The playback interface 125 may enable the user of the playback interface 125 to pause and/or rewind and replay the patient data. The playback interface 125 may enable review of the patient data in time periods including and/or prior to a current time period. The playback interface 125 may display the patient data in real-time as the operational interface 135 is simultaneously displaying the same patient data. In an implementation, the playback interface 125 may receive the patient data as image format data that constitutes a snapshot of the visual representation of that data on the operational interface 135. The playback interface 125 may display the snapshot and as such the visual representation of the data on the playback interface 125 may replicate and redisplay the visual representation of the data that matches a previously rendered image at the operational interface 135. Alternatively, the playback interface 125 may not replicate and redisplay the visual representation of the data that matches the previously rendered image of the data at the operational interface 135. Rather, the processor controlling the playback interface 125 may receive non-image format data and generate the visual representation of the data for the playback interface 125 based on the non-image format data. Therefore, the visual representation of the patient data on the playback interface 125 may be different from the visual representation of the same patient data at the operational interface 135, for example, the visual representation on the playback interface 125 may be rendered or otherwise displayed in a format and/or layout that differs from how the data was displayed on the operational interface.

FIGS. 1A-1D show examples of the patient data provided at the operational interface 135 and/or the playback interface 125. The patient data shown are examples only and not limiting of the disclosure. Further, some or all of the information shown in these examples on the playback interface 125 may be displayed on the operational interface 135 and vice versa. The patient data may include data provided by the therapy delivery component(s) 161a (e.g., second sensor data) and/or data provided by the one or more sensor(s) 161b (e.g., first sensor data). The patient data may include physiological measurements 140, 185 that correspond to a particular point in time (e.g., discrete physiological measurements). The physiological measurements 140, 185 may include, for example, blood pressure (e.g., non-invasive blood pressure (NIBP) and/or invasive blood pressure (IBP)), heart rate, respiration rate, temperature, oxygen saturation (e.g., SpO$_2$), end tidal carbon dioxide (e.g., EtCO$_2$), Near Infrared Spectroscopy (NIRS) measurements, and/or other physiological parameters. Additionally, or alternatively, the patient data may include physiological waveforms, body temperature time trends, heart rate time trends, respiration rate time trends, and/or other time trends. The waveforms may correspond to physiological sensor data received substantially continuously as a function of time, such as an electrocardiogram (ECG) as represented schematically by the waveforms 130a and 180. The time trends may correspond to sensor data measured at discrete time intervals and displayed as a function of time. For example, such sensor data may include, but is not limited to, end tidal carbon dioxide (EtCO2), as represented for example by the capnography time trend 130b and/or oxygen saturation (e.g., SpO2), as represented for example by the pulse oximetry time trend 130c. As another example, the sensor data may include patient temperature and the time trend data may include temperature trend data showing a patient temperature as a function of time. In an implementation, the patient data may include CPR performance data 194. The CPR performance data may include, for example, a compression depth 195, a compression rate 196, a chest release indicator 197, a perfusion performance indicator 198, and a CPR time indicator 199. In an implementation, the CPR performance data may include blood pressure data and/or blood flow data. These examples of patient data are not limiting of the disclosure as other types of data corresponding to various therapeutic medical devices are within the scope of the disclosure The processor 120 may be configured to implement a particular display mode to selectively display the operational interface 135 and the playback interface 125. The processor may select the implemented display mode from available display modes for the display screen 115. For example, as referred to above, the available display modes may include an operational interface only mode and a playback interface only mode. FIG. 1A shows an example of the operational interface only mode. In this mode, the display screen 115 may include the operational interface 135 and exclude the playback interface 125 (e.g., the processor 120 may control the display screen 115 to display the operational interface 135 and not to display the playback interface 125). FIG. 1B shows an example of the playback interface only mode. In this mode, the display screen 115 may include the playback interface 125 and exclude the operational interface 135 (e.g., the processor 120 may control the display screen 115 to display the playback interface 125 and not to display the operational interface 135).

Figure 1C:
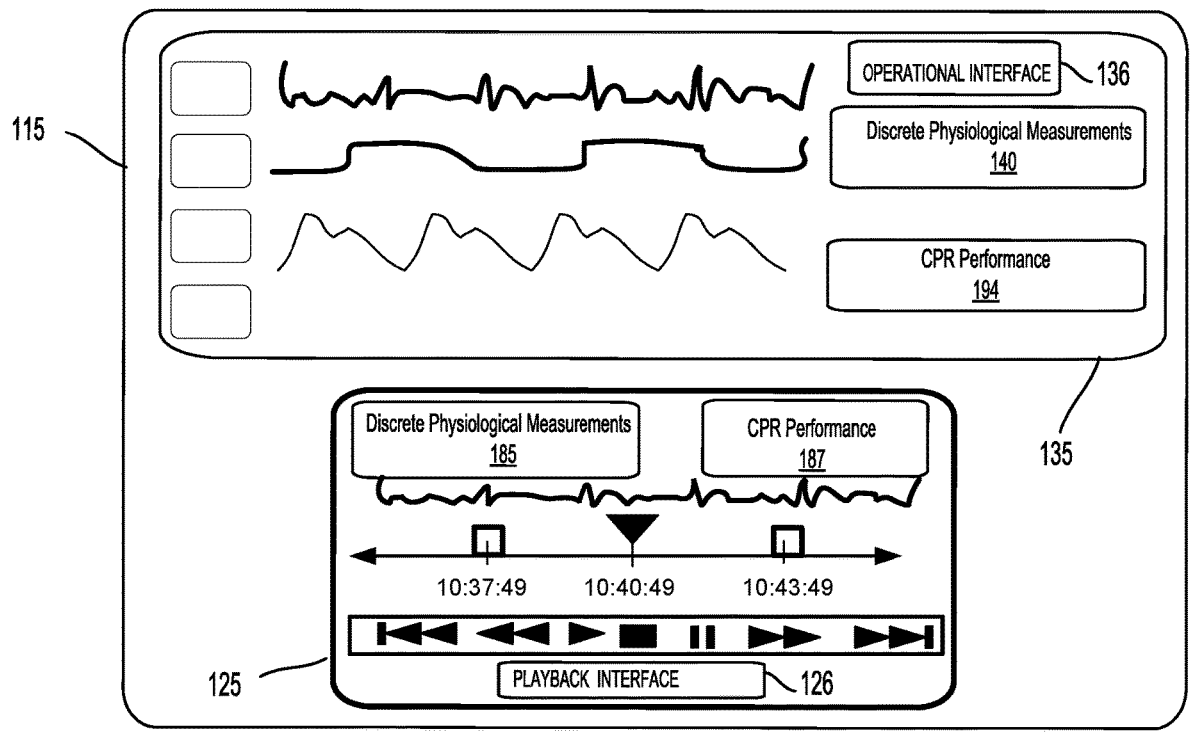
FIG. 1C shows an example of a combined operational/playback mode for the medical device.
Figure 1D:
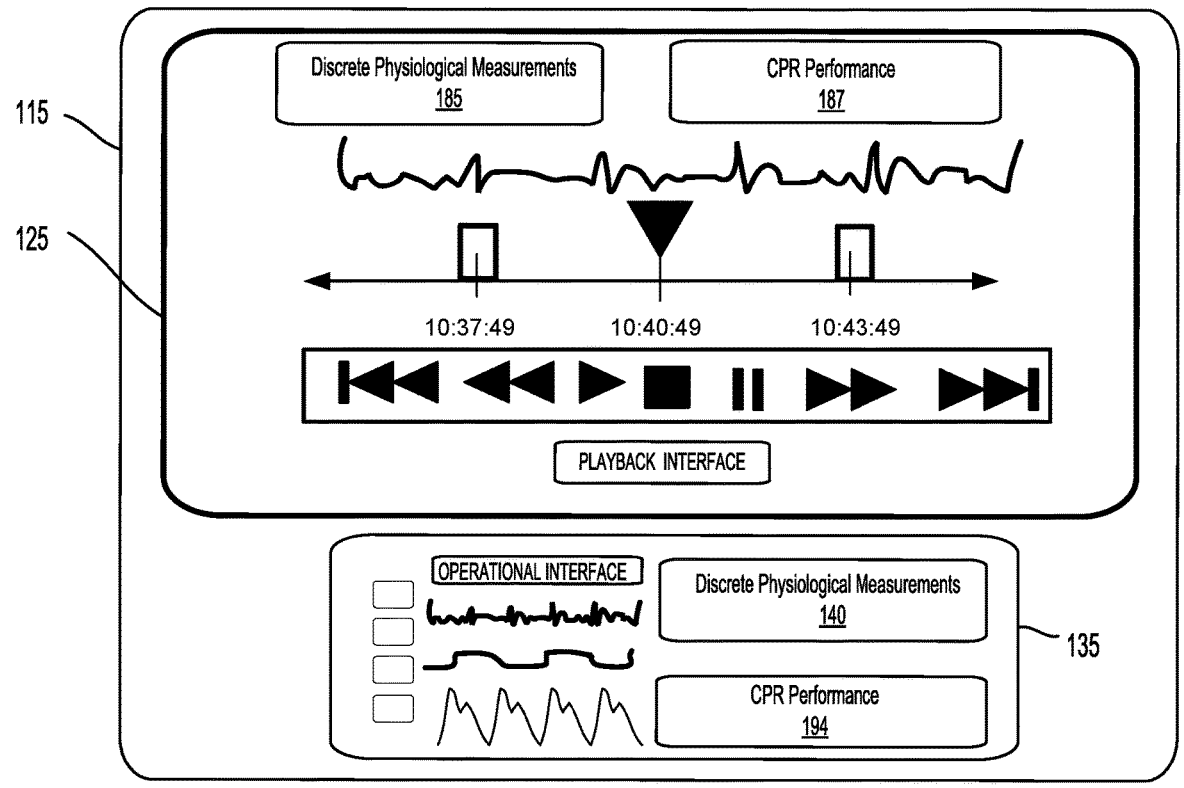
FIG. 1D shows an example of a combined operational/playback mode for the medical device.

In an implementation, the available display modes for the display screen 115 may include a combined operational/playback mode. Referring to FIGS. 1C and 1D, examples of the combined operational/playback mode are shown. In the combined operational/playback mode, the processor 120 may control the display screen 115 to simultaneously display the operational interface 135 and the playback interface 125.

In the simultaneous display, the display screen may provide the operational interface 135 in a first portion of the display screen 115 and may provide the playback interface 125 in a second and different portion of the display screen 115. The first portion and the second portion may be the same size or may be different sizes. For example, as shown in FIG. 1C, the playback interface 125 may occupy a smaller area on the display screen 115 than the operational interface 135. This configuration may be a default state for the medical device 110. Conversely, as shown in FIG. 1D, the operational interface 135 may occupy the smaller area on the display screen 115 than the playback interface 125.

The operational interface 135 and the playback interface 125 may include one or more identifying features 126 and 136 in at least a portion of the respective interface in order to unambiguously visually distinguish between these two interfaces. This may prevent the user of the medical device 110 from confusing the two interfaces. For example, the identifying features 126 and 136 may include different colors, different color schemes, different shapes, and/or distinguishing labels and/or graphics that identify the interface as the operational interface 135 or the playback interface 125.

The medical device 110 may simultaneously display the operational and playback interfaces in various combined mode display configurations. The combined mode display configuration may determine the relative sizes of the interfaces (i.e., which interface occupies the smaller area on the display screen 115 and which interface occupies the larger area on the display screen 115). For example, the simultaneous display may include a side-by-side configuration on one display screen without overlap between the two interfaces. As another example, one of the first portion and the second portion of the display screen 115 may be an inset window that overlaps the other of the first portion and second portion. The interface in the inset window may occupy a smaller area on the display screen than the interface that is not in the inset window. For instance, referring to FIG. 1E the playback interface 125 is shown as an inset window on the operational interface 135 and the operational interface 135 is shown as an inset window on the playback interface 125. In various implementations, the inset window may occupy an area approximately 10%, 20%, 30% or up to 50% of the total display area. As a further example, the medical device 110 may include multiple displays and the operational interface 135 and the playback interface 125 may occupy different displays. These configurations of the combined operational/playback mode are examples only and not limiting of the disclosure.

In an implementation, the user of the medical device 110 may provide user input that determines the selected display mode and/or the combined mode display configuration. For example, the user may select the display mode via a soft-key (e.g., one or more of the soft-keys 150a-150d shown, for example, in FIG. 1A) and/or other input device for the medical device 110. In an implementation, the medical device 110 may include a mechanical and/or electronic mode selection switch 66, as shown for example in FIG. 1A, in the form of a button, a knob, a toggle switch, a touchscreen button, a softkey (i.e. a mechanical switch whose function changes based on adjacent text on the display screen), etc. that may capture a user selection of the display mode. Selecting the display mode may include changing from one display mode to another and/or toggling between display modes in response to the user input. In an implementation, the display screen 115 may provide a display a display mode menu. In a further implementation, the medical device 110 may capture the user selection via a microphone (e.g. a verbal mode selection) and/or a haptic input device (e.g., a tactile input mode selection).

In an implementation, the display screen 115 may be a touchscreen configured to capture the user input that determines the selected display mode and/or the combined mode display configuration. Referring to FIGS. 1E-1I, examples of user selections via a touchscreen for the display mode are shown. FIGS. 1E-1I are examples only and are not limiting of the disclosure as other touchscreen gestures and combinations of gestures are within the scope of the disclosure. In an implementation, the touchscreen may be a pressure sensitive touchscreen and the gestures may include a push gesture to exert pressure on the display screen 115.

The percentage of the total area of the display screen 115 occupied by the playback interface 125 may increase or decrease based on the pressure exerted on the pressure sensitive touchscreen by the user. For example, the playback interface 125 may occupy a first area on the display screen 115 that corresponds to a smaller percentage of the total area of the display screen 115 than a second area on the display screen 115 occupied by the operational interface 135. When the pressure sensitive touchscreen detects a pressure that exceeds a threshold in the first area of the display screen (e.g., as occupied by the playback interface 125), the first area may expand to occupy a relatively larger percentage of the total area of the display screen 115. If the detected pressure drops below the threshold, the first area may shrink in size in response to the detected drop in pressure. In some implementations, the pressure threshold may be, for example, 0.1, 0.2, 0.5, 1, 2, or 5 pounds of force. In some implementations, there may be two pressure thresholds. A first pressure threshold may determine an expansion of the area of the playback interface 125, and a second pressure threshold may determine a reduction of the area of the playback interface 125. Similarly, in some implementations, the operational interface 135 may occupy an area on the display screen 115 that is a smaller percentage of the total area of the display screen 115 than the playback interface 125. Measured pressure at the pressure sensitive touchscreen and/or one or more predetermined thresholds may control the expansion and reduction of the area of the operational interface 135 in a manner similar to the above-described control of the area of the playback interface 125.

Figure 1E:
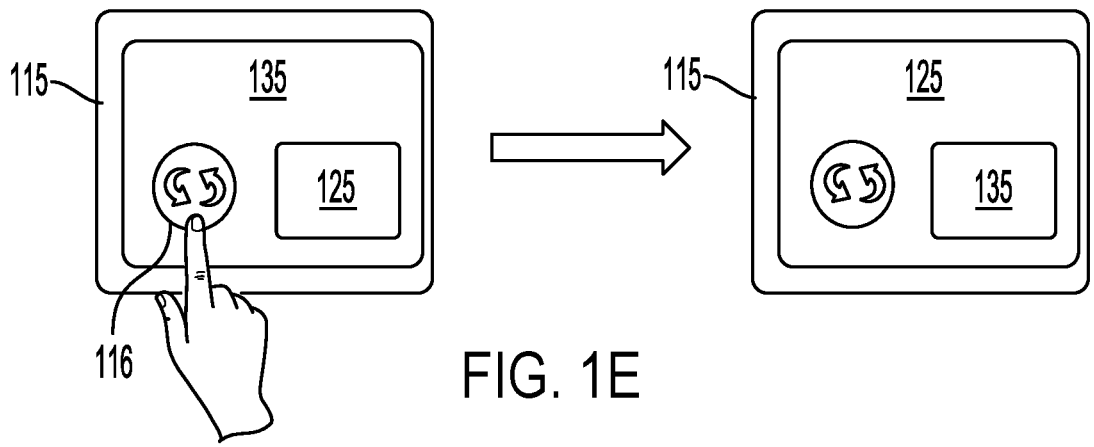
FIG. 1E shows an example of a user selection via a touchscreen for a display mode.

As shown schematically in FIG. 1E, the user may select the display mode via selection of a touchscreen icon. For example, the user may tap the touchscreen icon 116 to provide a touchscreen signal that causes the inset window to switch from the playback interface 125 to the operational interface 135.

Figure 1F:
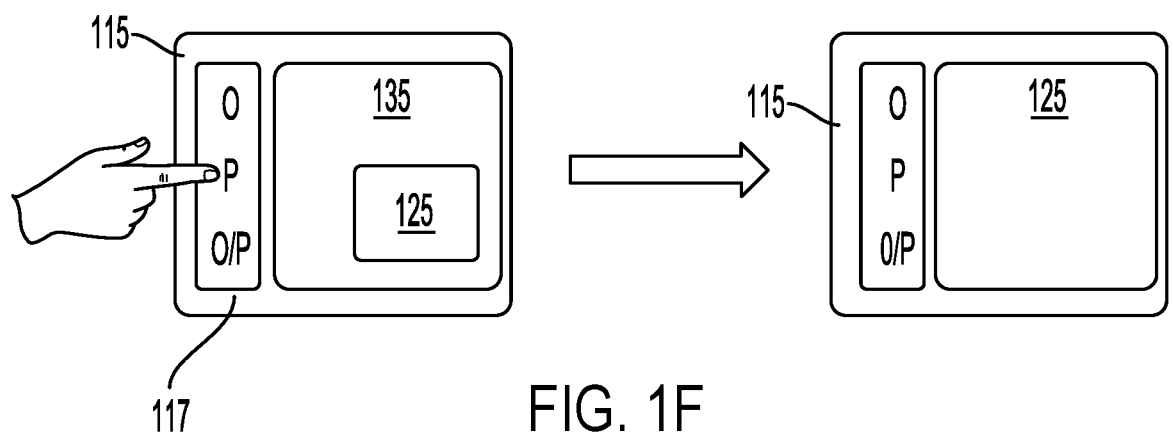
FIG. 1F shows an example of a user selection via a touchscreen for a display mode.

As shown schematically in FIG. 1F, the user may select the display mode via selection from a touchscreen menu, or may scroll to the desired selection via a control interface such as a knob, dial or button. As an example, the user may tap or select the "P" on the menu 117 to switch from the combined operational/playback mode to the playback interface only mode.

Figure 1G:
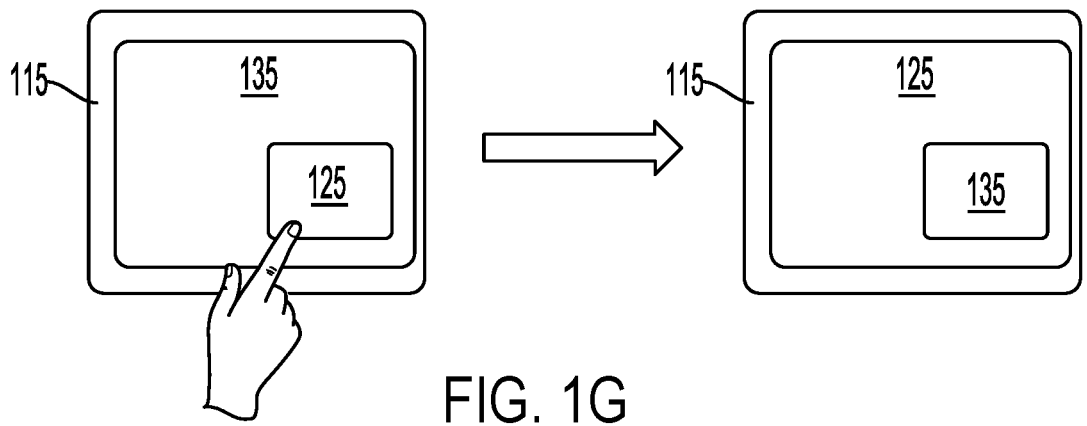
FIG. 1G shows an example of a user selection via a touchscreen for a display mode.

As shown schematically in FIG. 1G, the user may select the display mode via a touchscreen gesture on the desired interface. For example, the user may tap or push on the playback interface to display this interface on the larger area of the display screen and move the operational interface to the inset window so that the playback interface intuitively moves to a desired location as indicated by the user touch commands.

Figure 1H:
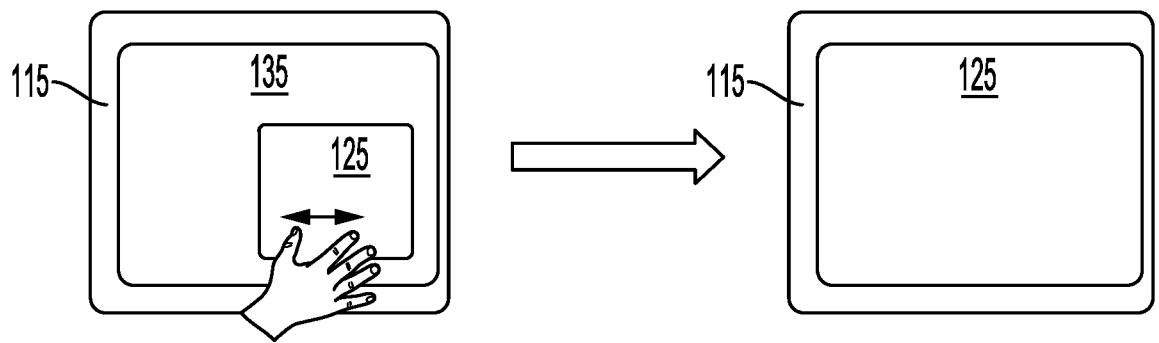
FIG. 1H shows an example of a user selection via a touchscreen for a display mode.

As shown schematically in FIG. 1H, the user may provide a touchscreen gesture to enlarge a desired interface. For example, the user may provide a two-finger gesture to the playback interface to switch the display mode from the combined operational/playback mode to the playback interface only mode. As another example, the user may provide the two-finger gesture to change the interface that is displayed in the inset window and/or to switch from the combined operational/playback mode to the operational interface only mode.

Figure 1I:
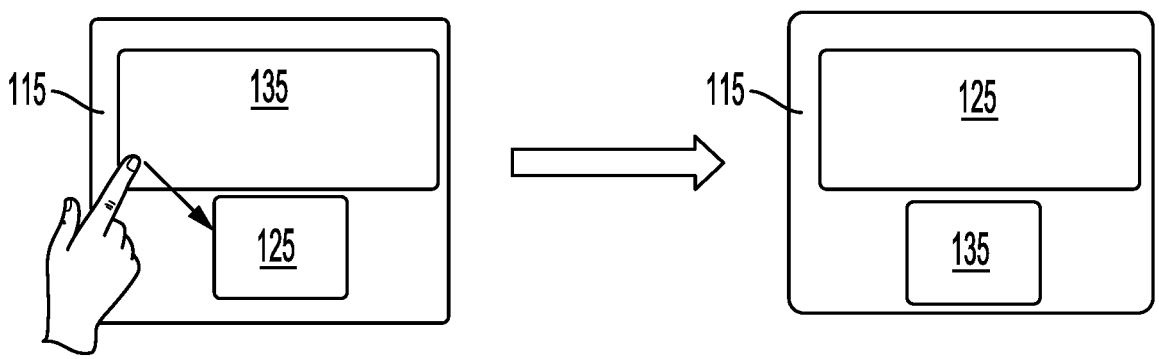
FIG. 1I shows an example of a user selection via a touchscreen for a display mode.

As shown schematically in FIG. 1I, the user may drag and drop a desired interface to a desired area on the display screen. For example, the user may drag the operational interface 135 to the inset window and in this manner switch the relative sizes of the operational and playback interfaces.

In some implementations, the area of the playback interface 125 may be approximately 10%, 20%, 30% or up to 50% of the area of the operational interface 135. A double-tap and/or another gestural interaction with the touchscreen and/or exerted pressure of a pressure sensitive screen, in the area of the playback interface 125, may cause the playback interface 125 area to enlarge to up to 90% of the operational interface 135 area. Subsequent to this enlargement, touching anywhere on the operational interface 135 area of the touchscreen causes the playback interface 125 area to decrease back to its previous size.

As an alternative to or in addition to the user input, in an implementation, the processor 120 (e.g., as shown in FIG. 11) may detect a state of the medical device 110. Based on the detected state of the medical device, the processor may automatically determine and implement a processor-selected display mode. In an implementation, the processor 120 may override a user selection to implement the processor-selected display mode and/or configuration. The processor 120 may automatically switch the display configuration from the user-selected display mode and/or configuration to a processor-selected display mode and/or configuration. As an example, depending on the state of the medical device, it may be crucial for the caregiver to view the operational interface. In such a case, for example, if the display screen 115 is in the playback interface only mode, the processor 120 may automatically change the implemented display mode to make the operational interface 135 available to the user of the medical device 110 (e.g., switch to the operational interface only mode or the combined operational/playback mode).

In an implementation, the processor 120 may be configured to detect that the medical device is in a therapy delivery state. In the therapy delivery state, the medical device 110 may currently or imminently be providing therapy to the patient. For example, the processor 120 may detect that the therapy delivery component(s) 161*a* are attached or likely to be attached to the patient. For instance, the processor 120 may detect this state for defibrillation electrodes via a transthoracic impedance measurement, a signal from an electrode package sensor that indicates an open package, a signal that two electrodes have been separated in order to attach them to the patient, etc. As another example, the therapy delivery state of the defibrillator may correspond to a detection that therapy delivery may be imminent based on a heart rhythm analysis and/or that defibrillation shock has been initiated and/or requested by the user. In an implementation, the processor 120 may be configured to detect the therapy delivery state based on an alarm state of the patient and/or the medical device. For example, a heart rate alarm triggered by a detected heart arrhythmia may indicate that cardiac therapy delivery may be imminent. Similarly, a blood oxygen level alarm may indicate that ventilation therapy delivery may be imminent.

In an implementation, the processor 120 may be configured to detect that the medical device is in a patient monitoring state. The patient monitoring state may correspond to the medical device being coupled to the patient via sensors only without therapy delivery components. For example, the medical device may be coupled to the patient via twelve-lead cardiac sensing electrodes but not with defibrillation electrodes.

In an implementation, the processor 120 may be configured to detect that the medical device is in a caregiver guidance state. For example, the medical device may be in the process of providing compression and/or ventilation feedback during cardiopulmonary resuscitation CPR, etc.

In an implementation, the processor 120 may limit the display modes available for user selection based on the state of the medical device. The processor 120 may disallow selection of one or more of the modes such that the processor may not implement the one or more of the modes at the display screen 115. For example, the processor 120 may limit the available display modes in response to a detection that the medical device 110 is coupled to the patient via the therapy delivery component(s) 161*a*. In this case, the processor 120 may disallow and/or disable selection of the playback interface only mode and may limit the modes available for user selection to the operational interface only mode and the combined operational/playback mode. In this way, the processor 120 may prevent the user of the medical device 110 from putting the medical device 110 into the playback interface only mode during delivery of critical care. As another example, the display screen 115 may be in the combined operational/playback mode with the operational interface 135 in the smaller area of the display screen 115. In response to the detection of the therapy delivery components being coupled to the patient, the processor 120 may automatically switch the configuration to put the playback interface 125 into the smaller area of the display screen 115. As a further example, the display screen 115 may be in the combined operational/playback mode with the playback interface 125 already in the smaller area of the display screen. In response to the detection of the therapy delivery components being coupled to the patient, the processor 120 may disable a user option to modify the display configuration to put the operational interface 135 into the smaller area of the display screen. In yet other examples, the processor 120 may allow or disallow selection of one or more of the display modes based on a type and/or skill level of a user (e.g., BLS, ALS, documenter, physician, etc.) and/or the processor 120 may allow or disallow selection of one or more of the display modes based on a clinical condition of the patient.

In an implementation, rather than automatically changing the display mode and/or configuration, the processor 120 may provide a display mode instruction for the user. For example, based on the detected medical device state, the processor 120 may control the display screen 115 and/or another output device, such as a microphone, to provide a user instruction to switch and/or maintain the display mode and/or configuration. The instruction for the user may be a message to switch to a particular mode or may be a message that the user should not select a particular mode.

In an implementation, the processor 120 may automatically determine, limit, or provide an instruction for the display mode and/or configuration based on a detected medical event. For example, the medical event may include a defibrillation shock, an arrhythmia, return of spontaneous circulation (ROSC) and/or another measured and/or observed physiological condition detected by the medical device 110. The medical device 110 may detect the medical event based on an automated assessment of the sensor signals and/or based on caregiver input. For example, in the case of a detection of certain heart rhythms, such as ventricular fibrillation or tachycardia, the medical device 110 may instruct the user not to switch to the playback interface only mode.

In another example, the processor 120 may detect or recognize ROSC based on a combination of a measured ECG heart rate between 30 and 120 BPM, a measured pulse oximetry pulse rate the same as the ECG heart rate, and a measured end tidal carbon dioxide value greater than 20. At the detection of ROSC, the processor 120 control the display screen 115 to automatically display the playback interface. For example, if the medical device 110 is in the operational interface only mode at the detection of ROSC, the processor 120 may automatically switch the medical device 110 to the combined operational/playback mode. Further, the processor 120 may control the playback interface 125 to start data playback at the point in time at which the processor 120 detected ROSC.

In an implementation, the processor 120 may request a confirmation of a display mode change from the user. The confirmation may be part of a processor-controlled or a user-requested display mode change. In a further implementation, the processor 120 may generate an alarm indicating an occurrence of or an impending occurrence of the display mode and/or configuration change. In another implementation, the processor 120 may generate the alarm and request the confirmation.

In an implementation, the software, firmware, and/or hardware associated with the medical device 110 may include a user and/or manufacturer configurable lockout setting that may prevent or limit display mode and/or configuration changes. The lockout setting may depend on the type of medical device and/or the status of the medical device. For example, an AED designed for use by caregivers who may have little or no medical training may include a lock-out setting that prevents the AED from being used in the playback interface only mode and/or from being used in a combined operational/playback mode with the playback interface in the larger area of the display screen. As another example, a defibrillator may include a lock-out setting that prevents the device from being used in the playback interface only mode and/or from being used in a combined operational/playback mode with the playback interface in the larger area of the display screen once the defibrillation electrodes are removed from a package and/or attached to the patient.

The playback interface 125 may leverage various display appearances to differentiate between this interface and the operational interface 135. The appearance of the playback interface 125 as an interface secondary to the operational interface 135 may remind the user to pay attention to the operational interface 135 to ensure that data review on the playback interface 125 enhances the delivery of care to the patient without detriment. In an implementation, the display screen (e.g., 115, 215, 315, 415a, and/or 415b) hosting the playback interface 125 may display the playback interface 125 with a grayed-out boundary as compared to the operational interface 135 in order to distinguish between them. Additionally or alternatively, the display screen hosting the playback interface 125 may provide the playback interface 125 with a background color and/or pattern that is different from the operational interface 135 in order to distinguish between these interfaces. In various implementations, the playback interface 125 may exhibit graphical elements such as shadowing, parallax, and/or other three-dimensional rendering such as shading, highlights, reflections, etc. These graphical elements may cause the playback interface 125 to appear either nearer or farther from the viewer than the operational interface 135. The appearance of the playback interface 125 as farther from the viewer than the operational interface 135 may serve to indicate to the user that the operational interface 135 is a primary functional interface.

Figure 2:
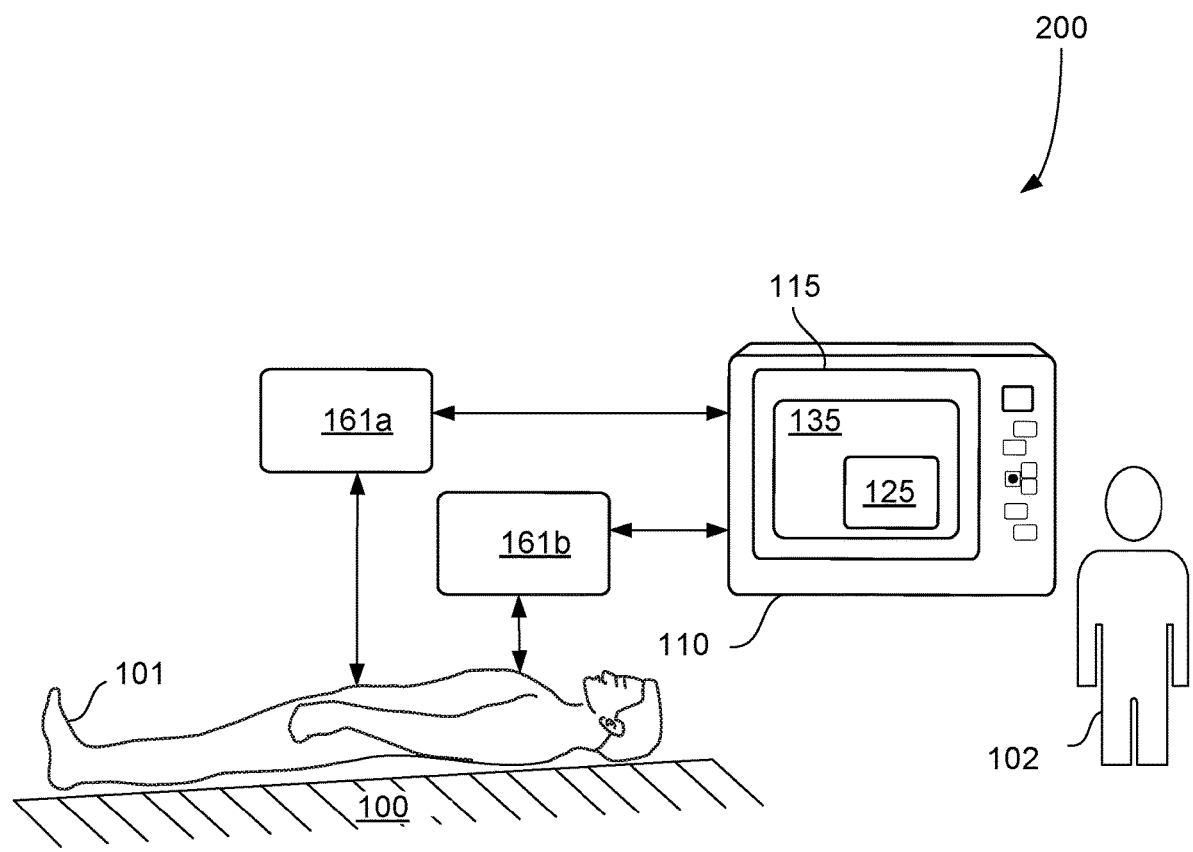
FIG. 2 shows an example of a device system that provides the operational and playback interfaces.

Referring to FIG. 2, an example of a device system that provides the operational and playback interfaces is shown. In the system 200, a medical device 110 is shown with the display screen 115 that displays the operational interface 135 and the playback interface 125 for the user 102. As discussed above, in addition to being configured to provide the combined operational/playback mode shown for example in FIG. 2, the medical device 110 may be configured to provide the operational interface only mode and the playback interface only mode. In the example of the combined operational/playback mode shown in FIG. 2, the playback interface 125 is an inset window to the operational interface 135. The medical device 110 may be configured to couple to the one or more therapy delivery component(s) 161a which may be configured to couple to the patient 101. In combination, the medical device 110 and the one or more therapy delivery components may provide therapeutic treatment to the patient 101. In an implementation, the medical device 110 may include or incorporate the therapy delivery component(s) 161a. Additionally or alternatively, the medical device 110 may include, incorporate, and/or be configured to couple to the one or more sensor(s) 161b which may be configured to couple to the patient 101. The operational interface 135 and the playback interface 125 may be configured to provide patient data captured by the first medical device 110 via the therapy delivery component(s) 161a and/or the sensor(s) 161b. The patient 101 may be supported by a support surface 100. The support surface 100 may be the ground, a floor, a bed, a gurney, a cot, a wheelchair, a chair, etc. The type of support surface 100 may depend on the type of therapy being provided.

Figure 3A:
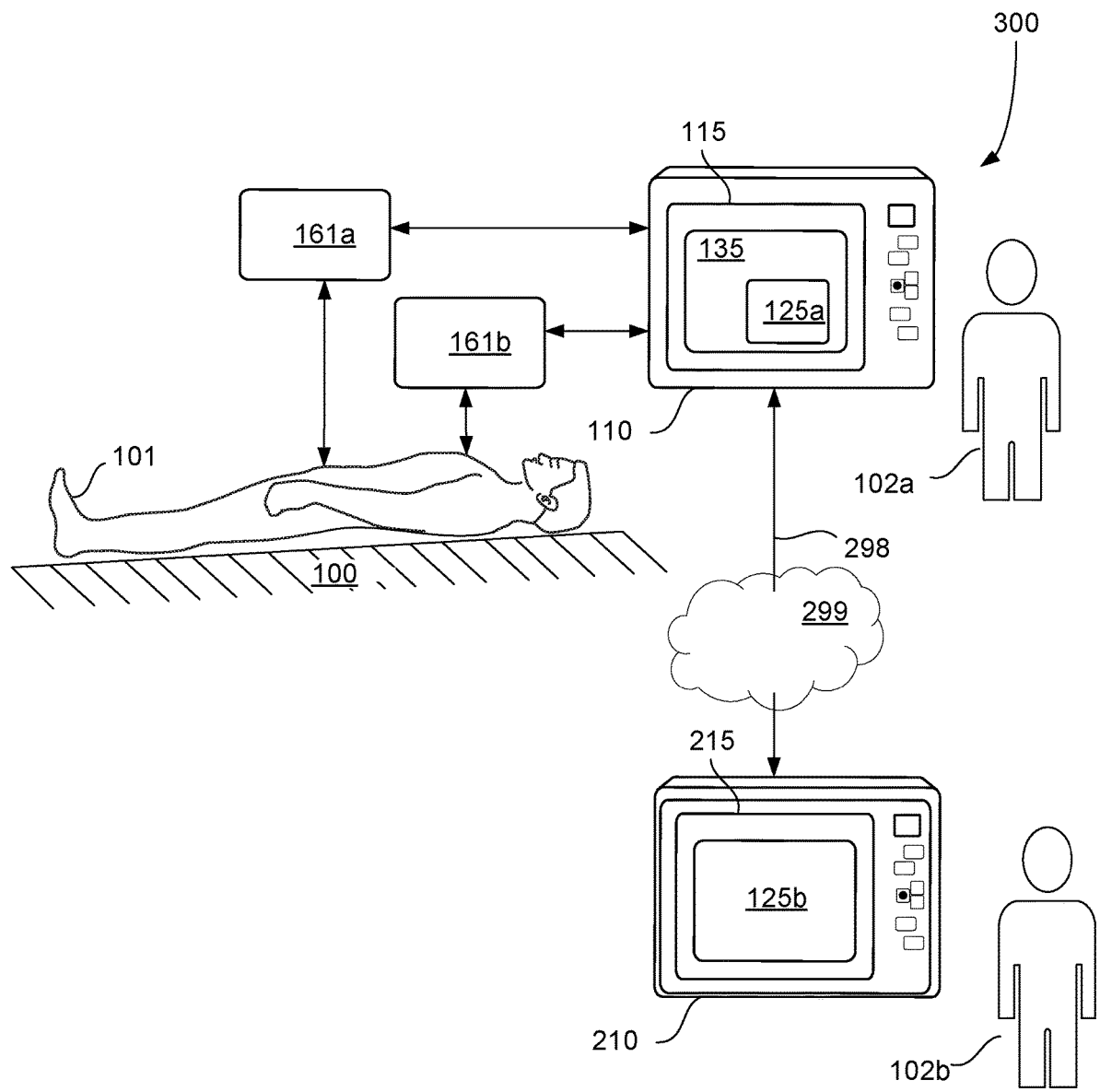
FIG. 3A shows an example of a multiple medical device system that provides the operational and playback interfaces.

Referring to FIG. 3A, an example of a multiple medical device system that provides the operational and playback interfaces is shown. In the system 300, the medical device 110 is a first medical device, the playback interface 125 is a first playback interface 125a, and the caregiver 102 is a first caregiver 102a. The system 300 further includes an auxiliary device. In this example, the auxiliary device is a second medical device 210 with a second display screen 215. The second display screen 215 may provide a second playback interface 125b for a second user 102b. Thus, one or more of the medical device and the auxiliary device may be the playback interface host device. The playback interfaces referred to herein as 125a and 125b may include all or a portion of the functions and features of the playback interface 125 as described herein. The designations of "125a" and "125b" merely serve to differentiate between host devices (e.g., the devices 110 and 210) of the playback interface 125 for clarity of description. The functionality and features of the first playback interface 125a may be the same as the second playback interface 125b. However, the visual representation of the patient data on the two devices 110 and 210 may be the same or may be different. Additionally, the portion of the patient data that is provided at the second playback interface 125b of the second medical device 210 may be the same or may be different than the portion of the patient data that is provided at the first playback interface 125a. Although shown in FIG. 3A with a single housing for simplicity, in an implementation, as described in further detail below with regard to FIG. 4B, the medical device 210 may be a modular therapy delivery/monitoring device (e.g., the device 410) that includes at least a first housing and a second housing.

As an example of a usage scenario, the first medical device 110 may be inconveniently located for access to the playback interface 125a. For example, the first medical device 110 may be under a gurney, behind another person at the scene of the patient 101, and/or otherwise inconveniently located due to chaos, space constraints, and/or other limitations imposed by the scene of the patient. In such a situation, it may be more convenient to review the patient data at the playback interface 125b than at the playback interface 125a. As another example, the caregiver 102a may not have sufficient medical knowledge or may be too busy with treating the patient to utilize the playback interface 125a. In such a situation, the first medical device 110 may be in the operational interface only display mode rather than the combined operational/playback mode shown in FIG. 3A. Thus, the second caregiver 102b may determine and provide care information based on the review of the patient data at the playback interface 125b.

The medical devices 110 and 210 are shown schematically in FIG. 3A as the same type of devices. However, in various implementations, the medical devices 110 and 210 may be the same or different types of medical devices. At least one of the first medical device 110 and the second medical device 210 may be a therapeutic medical device configured to provide therapy to the patient. One of the medical devices 110 and 210 may be a non-therapeutic device that may receive treatment information from the therapeutic medical device without collecting its own patient data. One of the medical devices 110 and 210 may monitor the patient and collect patient data without providing therapy. In the example of FIG. 3A, the first medical device 110 is the therapeutic medical device and the second medical device 210 receives treatment information from the therapeutic medical device without collecting its own patient data.

The first medical device 110 may be, for example, a therapeutic medical device capable of delivering a medical therapy. For example, the medical therapy may be electrical therapy (e.g. defibrillation, cardiac pacing, synchronized cardioversion, diaphragmatic or phrenic nerve stimulation) and the first medical device 110 may be a defibrillator, a defibrillator/monitor and/or another medical device configured to provide electrotherapy. As another example, the medical therapy may be chest compression therapy for treatment of cardiac arrest and the first medical device 110 may be a mechanical chest compression device such as a belt-based chest compression device or a piston-based chest compression device. As other examples, the medical therapy may be ventilation therapy, therapeutic cooling or other temperature management, invasive hemodynamic support therapy (e.g. Extracorporeal Membrane Oxygenation (ECMO)), etc. and the medical device 110 may be a device configured to provide a respective therapy. In an implementation, the medical device 110 may be a combination of one or more of these examples. The therapeutic medical device may include patient monitoring capabilities via one or more sensors. These types of medical therapy and devices are examples only and not limiting of the disclosure.

The second medical device 210 may be a therapeutic medical device as described above with regard to the first medical device 110. Alternatively, the second medical device 210 may be a patient monitoring device without the capability of providing medical therapy.

The second medical device 210 and the first medical device 110 may communicatively couple via a wired and/or wireless communicative coupling 298. The communicative coupling 298 may be a short-range and/or a long-range communicative coupling. In an implementation, the communicative coupling 298 may be a near-field communications link (e.g., via the NFC tag 80). The communicative coupling 298 may be a bi-directional communications link. The communicative coupling include a network 299 (e.g., a cellular network, a computer network, a local area network, a wide area network, etc. or combinations thereof). The first medical device 110 may provide captured and stored patient data and/or stream real-time patient data to the second medical device 210 via the communicative coupling 298. The communications link 298 and network 299 are discussed further in regards to FIG. 11.

The second playback interface 125b on the second medical device 210 may provide the patient data collected by and received from the first medical device 110. The users 102a and/or 102b may review the patient data at the playback interface 125a and/or 125b. In addition to being configured to provide the playback interface only mode as shown for example in FIG. 3A, the second medical device 210 may be configured to provide the operational interface only mode and the combined operational/playback mode.

In a usage scenario with two or more communicatively coupled devices, it may be beneficial for a user of one device to modify the information provided at another device. For example, based on data review at the playback interface 125b, the user 102b may provide user input at the second medical device 210 that causes the first medical device 110 to modify the information provided for the user 102a at the first medical device 110. The second medical device 210 may capture the user input (for example, at the playback interface 125b) and send the user input to the first medical device 110 via the communicative coupling 298 between the two devices. The first medical device 110 may receive the user input and modify the information provided on the display screen 115 according to the received user input. In various implementations, the user input may include an instruction to automatically display selected patient data and/or may include an instruction to provide the user input as user feedback. Playback interface features for capturing the user input are discussed further below with regard to FIGS. 10B and 10C.

As an example, the user 102b of the second medical device 210 may review the patient data collected by the first medical device 110 at the playback interface 125b. The patient data may include a capnography waveform, a pulse oximetry waveform, and an ECG. The user 102b may evaluate the patient data and determine that the caregiver 102a should view the capnography waveform in order to adjust ventilation provided to the patient. As described further with regard to FIG. 10B, the user 102b may provide user input to the playback interface 125b that generates an instruction for the first medical device 110 to display the capnography waveform. In response to receipt of this instruction, the first medical device 110 may automatically display the capnography waveform. Alternatively, in response to receipt of this instruction, the first medical device 110 may prompt the user 102a to select the capnography waveform for display. The processor 120 of the first medical device 110 may control the display 115 to display the capnography waveform at one or more of the operational interface 135 and the playback interface 125a in response to the received instruction.

In an implementation, the user feedback may include one or more visible and/or audible instructions provided at the operational and/or the playback interface. For example, the visible instructions may include text instructions, graphic instructions, animated instructions, video instructions, a live video stream, a pre-recorded video, a written and/or video chat, etc. As additional or alternative examples, the visible instructions may include data annotations and/or other display changes to the playback interface features. For example, display changes may include color and/or font changes, additional event markers, flashing event markers and/or data, highlighted time intervals for displayed data (e.g., color indications of times on the timeline and/or color changes to selected data portions corresponding to particular time ranges), hidden data and/or hidden portions of data, etc. As further examples, the audible instructions may include live audio stream, pre-recorded audio, audio-video instructions (e.g., live and/or pre-recorded), an audio chat, a live communication with the user of the second medical device (e.g., a cellular, Internet, and/or other network based audio call), an alarm, a tone or other noise emitted from the first medical device, etc. In an implementation, the first medical device 110 may provide a user selectable icon to enable the provision of instructions. For example, an icon may read "press to play instructions" and in response to user pressure on the icon, the first medical device 110 may provide the instructions.

As another example, at the playback interface 125b, the user 102b may review the ECG collected by the first medical device 110. The user 102b may notice a significant feature in the ECG over a time period during which medication was administered to the patient 101 by the caregiver 102a. The user 102b may provide a user input indicative of an instruction for the caregiver 102a to review the ECG at a time period selected by the user 102b. In response to receipt of this instruction, the first medical device 110 may automatically display the ECG on the playback interface 125a at the selected time period. Alternatively, in response to receipt of this instruction, the first medical device 110 may prompt the user 102a to review the ECG at the selected time period at the playback interface 125a. Additionally, the user input may include a note that the caregiver 102a should review the ECG prior to any further drug administration. The first medical device 110 may provide this note to the caregiver 102a via visible and/or audible feedback at the first medical device 110.

Figure 3B:
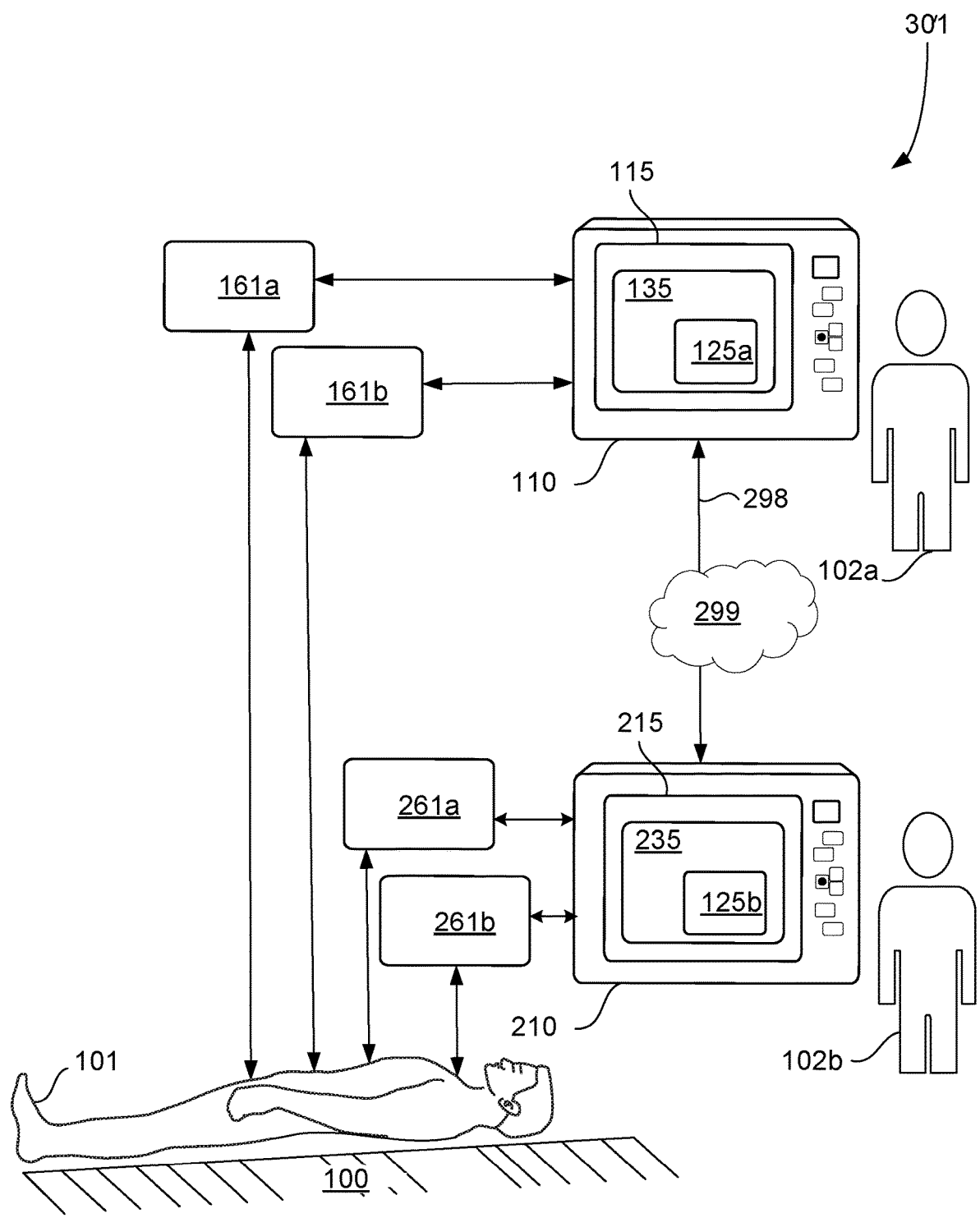
FIG. 3B shows an example of medical devices configured for coordinated and/or sequential care.

Referring to FIG. 3B, an example of medical devices configured for coordinated and/or sequential care is shown. In the system 301, one or both of the first medical device 110 and the second medical device 210 may be a therapeutic medical device. The first medical device 110 may provide the operational interface 135 and/or the playback interface 125a. The second medical device 210 may provide the operational interface 235 and/or the playback interface 125b. The operational interface 235 may include all or a portion of the functions and features of the operational interface 135 as described herein. In an implementation, the operational interface 235 may include additional and/or alternative features relative to the operational interface 135 based on the therapeutic and/or monitoring capabilities of the second medical device 210 relative to the first medical device 110. The designations of "135" and "235" serve to differentiate between host devices (e.g., the devices 110 and 210) of the operational interface 135 for clarity of description. The second medical device 210 may be configured to couple to one or more therapy delivery component(s) 261a. Additionally or alternatively, the second medical device 210 may be configured to couple to one or more sensor(s) 261b. In an implementation, the first medical device 110 may be the therapeutic medical device and the second medical device 210 may monitor the patient and collect patient data without providing therapy. The sensor(s) 161b and 261b and/or the therapy delivery component(s) 161a and 261a may enable the medical devices 110 and 210 to coordinate and/or synchronize delivery of care to and/or gathering of patient data from the patient 101. In the example of FIG. 3B, both of the medical devices 110 and 210 are shown in the combined operational/playback mode. However, this is an example only and each of the medical devices 110 and 210 may be configured to implement the operational interface only mode and/or the playback interface only mode. The devices 310 and/or 410 discussed below may also be configured to implement the operational interface only mode, the playback interface only mode, and/or the combined operational/playback mode.

In an implementation, the medical devices 110 and 210 may be provide the same level of care. For example, these two devices may both be defibrillators or defibrillator/monitors and provide synchronized electrotherapy. Alternatively, the medical devices 110 and 210 may provide different levels of care (e.g., tiered care). For example, the first medical device 110 may be an automated external defibrillator (AED) or other defibrillator configured to provide basic resuscitative care (e.g., a basic life support (BLS) device). In the event of a cardiac arrest, a bystander (e.g., the user 102a) may initially treat a victim 101 of the cardiac arrest with the AED and call emergency medical services (EMS). EMS may provide the device 210 which may be a patient monitor/defibrillator configured for advanced resuscitative care (e.g., an advanced life support (ALS) device). The second medical device 210 may arrive at the patient scene after the first medical device 110 may have already been on-scene for some time period and was used to diagnose and/or treat the patient 101.

The processors 120, 220, 320, and/or 420 (e.g., as shown in FIGS. 11 and 12) of the respective devices 110, 210, 310, and/or 410 may implement a particular display mode to selectively display the operational interface 135 and the playback interface 125 based on a functional relationship between at least two of the devices 110, 210, 310, and/or 410 with regard to criticality or priority of care. The processors of the devices 110, 210, 310, and/or 410 may determine and/or assign a priority level to therapy and/or monitoring provided by each device and implement the display mode based on this assigned priority level. The functional relationship may represent an evaluation of a priority of care of one device relative to another.

For example, in a usage scenario, one of the medical devices 110 and 210 may provide higher priority therapeutic care (e.g., a higher level of critical care) relative to the other one of the medical devices 110 and 210. Similarly, one of the medical devices 110 and 210 may provide lower priority therapeutic care (e.g., a lower level of critical care) relative to the other one of the medical devices 110 and 210. The higher priority therapeutic care may be therapy delivery that is more likely to cause harm to the patient if improperly administered than the lower priority care. For instance, the first medical device 110 may be configured to provide a defibrillation shock to the patient and the second medical device 210 may be configured to provide chest compressions and/or pacing to the patient. In this instance, the defibrillation shock is the higher priority therapeutic care and the chest compression is the lower priority therapeutic care. While both of these therapies provide critical and important care and could cause harm to the patient if improperly administered, the improper defibrillation shock (e.g., improper timing, energy, etc.) may be more likely to cause more harm to the patient than an improper chest compression. Thus, the first medical device 110 may assign a higher priority level of critical care to the defibrillation shock provided by this device than the chest compression provided by the second medical device 210.

As another example, the processors 120 and 220 may base a prioritization scheme on an ALS/BLS schema. Such a schema results in higher priority for therapies only available with ALS (e.g. pacing, therapeutic hypothermia, intubation, etc.) than for therapies available with BLS (e.g. chest compressions, defibrillation, etc.).

This automatic control of the selective display based on the functional relationship may override captured user input based on a detection of a state of the respective medical device and/or a level of critical care provided by the respective medical device. In an implementation, the communicatively coupled devices (e.g., two or more of the devices 110, 210, 310, and 410) may share patient interface information in order to define the functional relationship between the two devices.

The patient interface information may include a device status and/or care information. For example, the patient interface information may include an indication that the first medical device and/or the auxiliary device is coupled to the patient via the one or more patient interface devices and/or may include an indication of one or more of a type of therapy and a type of sensor provided by the one or more patient interface devices. During usage, one or more of the processors (e.g., 120, 220, 320, and 420) may dynamically evaluate the patient interface information and determine a relative criticality of care between the two devices. Based on this evaluation and the determined relative criticality of care, one or more of the processors of the medical device and the auxiliary device (e.g., 120, 220, 320, and 420) may adjust the selective display of a respective playback interface based on one or more of the patient interface information and the relative criticality of care and/or based on changes in these factors.

In an implementation, the first medical device and the auxiliary device may be configured to automatically exchange patient interface information in response to an establishment of a communicative coupling between the two devices. In an implementation, one or more of these devices may evaluate the patient interface information and the relative criticality of care and adjust the data display at the playback interface based on this evaluation. For example, the device may determine one or more particular data types to display and/or may determine one or more of events and time intervals to represent with the displayed data.

Tables 1-5 below provide examples of the functional relationship determined based on such an information exchange and the resultant display screen mode implementation. In these examples, "O" refers to operational mode only, "P" refers to playback mode only, and "O/P" refers to combined operational/playback mode. "P inset" indicates that that playback interface occupies a smaller area on the display screen than the operational interface. "O inset" indicates that the operational interface occupies a smaller area on the display screen than the playback interface. In the example of Table 5, both devices provide defibrillation therapy. This may occur, for example, when two defibrillators are used for synchronized electrotherapy. In the patient transition from one therapeutic medical device to another (e.g., described with below regard to FIG. 3C), the functional relationships between the first medical device and the auxiliary device may change, for example, from that shown in Table 1 to that shown in Table 3. Accordingly, the processors (e.g., 120, 220, 320, and/or 420) may then adjust the display modes provided on the device 110, 210, 310, and/or 410. In each table, the "available display mode" and the "combined mode configuration" refers to a status of the display screen for each listed device.

TABLE 1

|  | Medical Device 1 | Auxiliary Device |
| --- | --- | --- |
| Therapy delivery component coupled to patient? | yes | no |
| Type of therapy | defibrillation | none |
| Sensors coupled to patient? | Yes-ECG | no |
| Higher level of critical care? | yes | no |
| Available display mode(s) | O, O/P | P |
| Combined mode configuration | P inset | none |

TABLE 2

|  | Medical Device 1 | Auxiliary Device |
| --- | --- | --- |
| Therapy delivery component coupled to patient? | yes | no |
| Type of therapy | defibrillation | none |
| Sensors coupled to patient? | Yes-ECG | Yes-pulse oximeter |

TABLE 2-continued

|  | Medical Device 1 | Auxiliary Device |
| --- | --- | --- |
| Higher level of critical care? | yes | no |
| Available display mode(s) | O, O/P | O, O/P |
| Combined mode configuration | P inset | O inset or P inset |

TABLE 3

|  | Medical Device 1 | Auxiliary Device |
| --- | --- | --- |
| Therapy delivery component coupled to patient? | no | yes |
| Type of therapy | none | Drug administration |
| Sensors coupled to patient? | Yes-ECG | Yes-Blood pressure |
| Higher level of critical care? | no | yes |
| Available display mode(s) | O, O/P | O, O/P |
| Combined mode configuration | O inset or P inset | P inset |

TABLE 4

|  | Medical Device 1 | Auxiliary Device |
| --- | --- | --- |
| Therapy delivery component coupled to patient? | yes | yes |
| Type of therapy | defibrillation | ventilation |
| Sensors coupled to patient? | Yes-ECG | Yes-pulse oximeter |
| Higher level of critical care? | yes | no |
| Available display mode(s) | O, O/P | O, O/P |
| Combined mode configuration | P inset | P inset |

TABLE 5

|  | Medical Device 1 | Auxiliary Device |
| --- | --- | --- |
| Therapy delivery component coupled to patient? | yes | yes |
| Type of therapy | defibrillation | defibrillation |
| Sensors coupled to patient? | Yes-ECG, pulse oximeter | Yes-ECG, pulse oximeter |
| Higher level of critical care? | yes | yes |
| Available display mode(s) | O, O/P | O, O/P |
| Combined mode configuration | P inset | P inset |

Figure 3C:
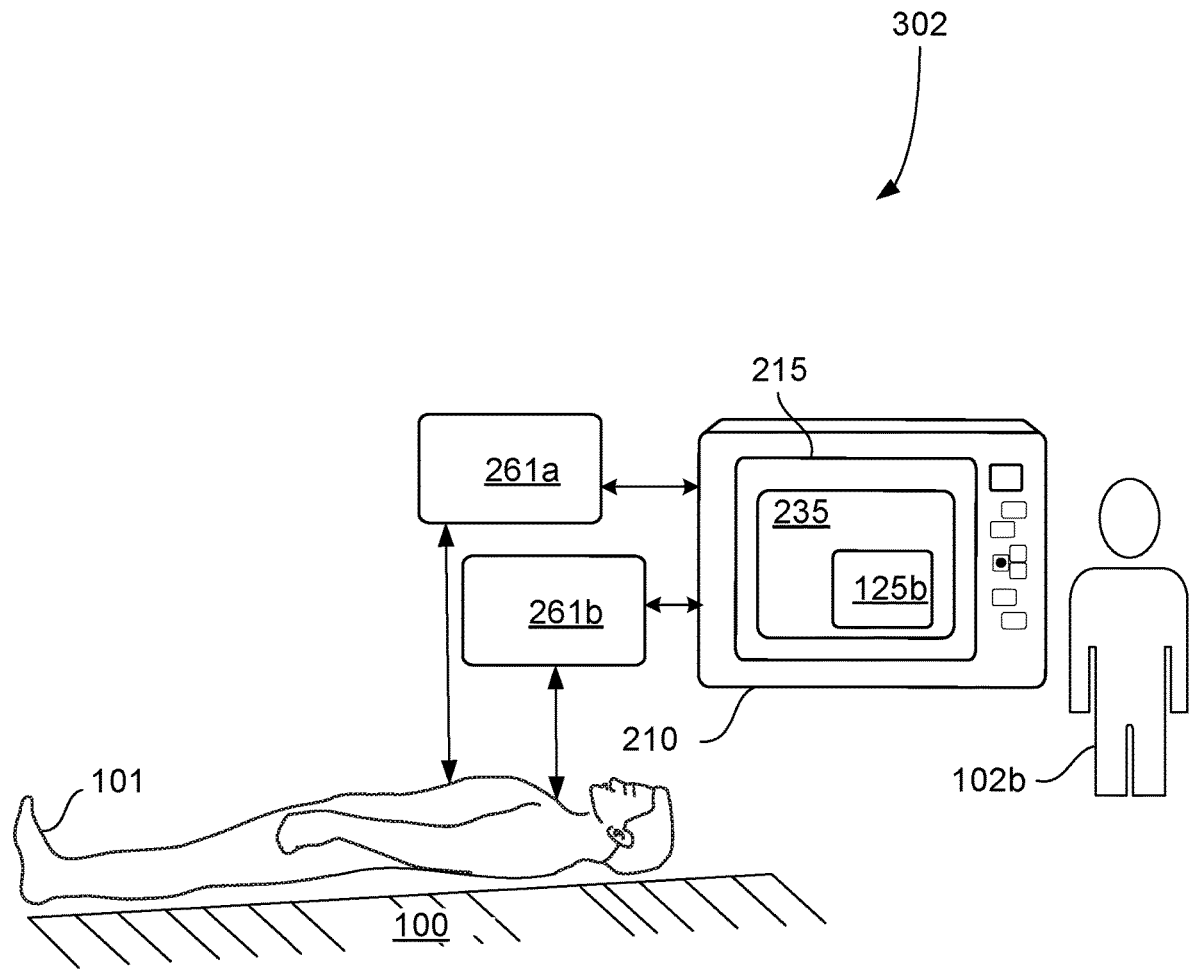
FIG. 3C shows an example of a transition of a patient to a second medical device.

Referring to FIG. 3C, an example of a transition of a patient to a second medical device is shown. For example in the system 302, a transition of the patient 101 from the first medical device 110 to the second medical device 210 is shown schematically. For such a transition, the user 102*b* of the second medical device 210 may couple the patient 101 to the second medical device 210 (e.g., couple the patient to the therapy delivery components 261*a* and/or sensor(s) 261*b*) and decouple the patient 101 from the first medical device 110 (e.g., decouple the patient from the therapy delivery component(s) 161*a* and/or the sensor(s) 161*b*).

In practice, several transitions may occur during a tiered care resuscitative treatment. For example, a first transition may occur from a bystander to a fire and/or EMS rescuer. A second transition may occur from the fire and/or EMS rescuer to a transport team (e.g., an ambulance crew). A third transition may occur from the transport team to a hospital. At each transition, it is desirable for the new caregiver(s) to understand where the data came from, and what happened to the patient. Further, at each transition, the new caregiver(s) may introduce one or more additional medical devices (e.g., devices 110, 210).

Following a transition to and/or addition of the second medical device 210 in the care of the patient 101, the processor 120 of the first medical device 110 and/or the processor 220 of the second medical device 210 may chronologically merge first patient data determined based on processing of sensor signals at the first medical device 110 with second patient data determined based on processing of sensor signals at the second medical device 210 and create an integrated record. The integrated record may include tags indicating the source of the data (e.g., whether it was determined based on processing of sensor signals at the first medical device 110 or determined based on processing of sensor signals at the second medical device 210). The tags may further indicate a type of device (e.g. an AED, a BLS defibrillator, an ALS defibrillator, a patient monitor, a compression device, a ventilator, a drug administration device, a temperature management device, an ECMO device, etc.). The integrated record may include data from all or a portion of multiple medical devices that are used to treat and/or monitor the patient. During coordinated and/or synchronized care by multiple medical devices, the playback interface 125 (e.g., playback interfaces 125a and 125b) may access and display data from the merged records. An advantage of the merged records is that the subsequently arriving caregivers may review data at their own devices (e.g., at the playback interface 125b on the second medical device 210 and/or the playback interface 125c on a mobile computing device 310 as described below with regard to FIG. 4A). In this manner, the subsequently arriving caregivers may view, review, and analyze what happened and is happening during treatment without having to view or otherwise physically access previously used medical equipment.

Figure 4A:
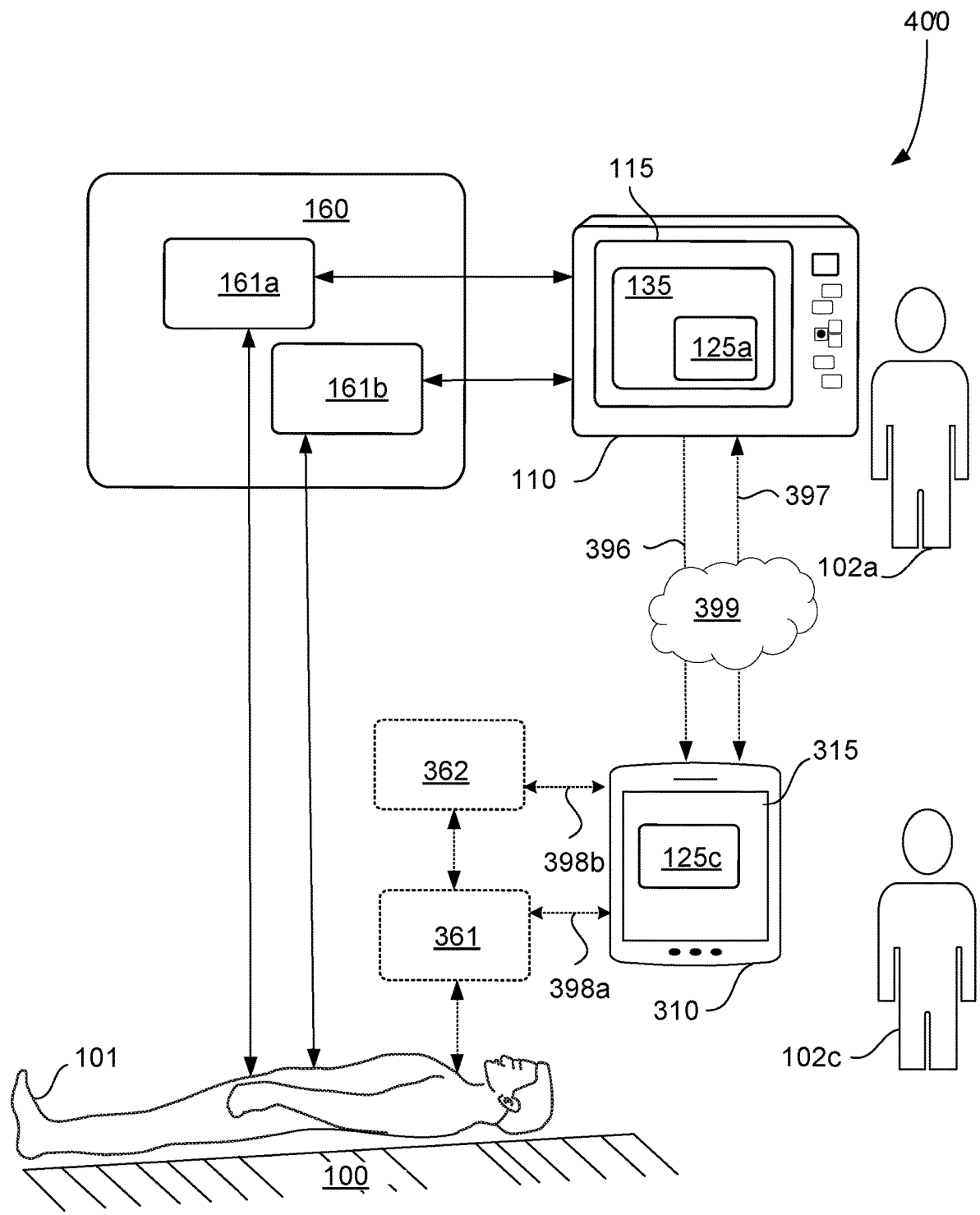
FIG. 4A shows an example of a system that includes a medical device and a computing device providing the operational and playback interfaces.

Referring to FIG. 4A, an example of a system that includes a medical device and a computing device and provides the operational and playback interfaces is shown. In the system 400 of FIG. 4A, the medical device 110 may provide therapy to and/or capture patient data for the patient 101 (e.g., via the sensor(s) 161b and/or the therapy delivery component(s) 161a). The display screen 115 of the medical device 110 may be configured to provide the operational interface 135 and/or the playback interface 125a. A display screen 315 of the auxiliary device, for example, the computing device 310, may provide the playback interface 125c for review of the patient data gathered from the sensor(s) 161b and/or the therapy delivery component(s) 161a. Thus, one or more of the medical device 110 and the computing device 310 may be the playback interface host device.

In an implementation, the first medical device 110 may provide captured patient data to the computing device 310 via a communicative coupling 396 or 397. The computing device 310 may receive the patient data from the medical device 110 via the communicative coupling 396 or 397. The patient data received at the computing device 310 via the medical device 110 may originate from the patient interface devices 160. As described above, the patient interface devices 160 may include the therapy delivery component(s) 161a and/or the sensor(s) 161b.

The communicative couplings 396 and/or 397 may be wired and/or wireless communicative couplings. Further, each of the communicative couplings 396 and 397 may be a short-range and/or a long-range communicative coupling. Thus, the computing device 310 may be a remote device or a local device. In an implementation, the communicative couplings 396 and/or 397 may be near-field communications links (e.g., via the NFC tag 80). The communicative coupling may include a network 399 (e.g., a cellular network, a computer network, a local area network, etc. or combinations thereof). The playback interface 125c may include all or a portion of the functions and features of the playback interface 125 as described herein. The designation of "125c" merely serves to differentiate between implementations of the playback interface 125 on a particular device for clarity of description.

In an implementation, the computing device 310 may not enable interaction between the user 102c of the computing device 310 and the medical device 110 via the computing device 310. For example, the computing device 310 may receive patient data from the medical device 110 via the communicative coupling 396, as illustrated schematically by the one-way arrow in FIG. 4A. The computing device 310 may provide display capabilities for the playback interface 125c and may enable the user interaction capabilities of the playback interface 125c as described herein.

In another implementation, the computing device 310 may receive patient data from the medical device 110 and enable user interaction between the user 102c of the computing device 310 and the medical device 110 via the computing device 310. The communicative coupling 397 may enable this interaction (e.g., as illustrated schematically by the two-way arrow in FIG. 4A and FIG. 11). This interaction may enable an exchange of, for example, medical consultations, treatment recommendations, and/or diagnoses based on data review at the computing device 310 via the playback interface 125c. The communicative coupling 397 may enable this exchange between the user 102c and the user 102a based on user input to the computing device 310 and/or the medical device 110 and exchanges of information between these two devices via the communicative coupling 397.

In an implementation, the computing device 310 may be adapted for medical applications and function as a physiological sensor interface. In various implementations, the one or more sensor(s) 361 may be in various configurations, For example, the one or more sensor(s) 361 may be incorporated in the computing device 310, may be configured to couple to the computing device 310, may be configured to couple to a patient monitor 362, may be incorporated in the patient monitor 362, and combinations thereof. As a further example, at least a portion of the one or more sensor(s) 361 may couple to and/or be incorporated in a patient monitor 362. The one or more sensor(s) 361 may be configured to couple to and/or interface with the patient 101. The computing device 310 may collect sensor data via the sensors 361 independently from the medical device 110. The computing device 310 may provide the physiological patient interface when it acquires sensor data from the patient 101 independently from and/or in addition to the medical device 110. In various implementations, the computing device 310 may receive patient data from the sensors 361 (e.g., communicative coupling 398a) and/or receive patient data from the sensors 361 via the patient monitor 362 (e.g., communicative coupling 398b). The coupling 398a (e.g., between the computing device 310 and the sensors 361) and the coupling 398b (e.g., between the computing device 310 and a patient monitor 362) are shown with dashed lines to schematically illustrate that the computing device 310 may function as the physiological sensor interface in some implementations and may not function as the physiological sensor interface in other implementations.

Similarly to the sensor(s) 161b and 261b, the sensor(s) 361 may provide signals indicative of patient data to the computing device 310. A processor of the computing device (e.g., the processor 320 shown in FIG. 11) may determine and/or generate the patient data based on the signals from the sensor(s) 361. The processor 120 of the first medical device 110 and/or the processor 320 of the computing device 310 may chronologically merge the data from the first medical device 110 with the patient data received at the computing device 310 to create the integrated record as described below with regard to the processors 120 and 220 of the medical devices 110 and 210.

Although shown as a tablet computer in the example of FIG. 4A, the computing device 310 may be, for example, but not limited to, a server or a personal user device such as a personal computer, a laptop computer, a mobile device, a hand-held device, a wireless device, a tablet computer, a wearable device (e.g., a wrist-worn device, a head-worn device, heads up display, etc.), or combinations thereof. The computing device 310 may be a group of communicatively coupled devices. Claimed subject matter is not limited to a particular type, category, size, etc. of computing device. In various implementations, the computing device 310 may be proximate to the medical device 110 or may be remotely located from the medical device 110. For example, the computing device 310 may be associated with a facility such as a hospital, a doctor's office, an EMS dispatch, a fire station, etc. Alternatively, the computing device 310 may be associated with a particular caregiver and/or located in a vehicle (e.g., an ambulance, a fire truck, a police car, a paramedic's vehicle, etc.).

In a usage scenario with two or more communicatively coupled devices, it may be beneficial for a user of one device to modify the information provided at another device. For example, based on data review at the playback interface 125c, the user 102c may provide user input at the computing device 310 that causes the first medical device 110 to modify the information provided for the user 102a at the first medical device 110. The computing device 310 may capture the user input (for example, at the playback interface 125c) and send the user input to the first medical device 110 via the communicative coupling 397 between the two devices. The first medical device 110 may receive the user input and modify the information provided on the display screen 115 according to the received user input. In various implementations, the user input may include an instruction to automatically display selected patient data and/or may include an instruction to provide the user input as user feedback. Playback interface features for capturing the user input are discussed further below with regard to FIGS. 10B and 10C.

As an example, the user 102c of the computing device 310 may review the patient data collected by the first medical device 110 at the playback interface 125c. The patient data may include a capnography waveform, a pulse oximetry waveform, and an ECG. The user 102c may evaluate the patient data and determine that the caregiver 102a should view the capnography waveform in order to adjust ventilation provided to the patient. As described further with regard to FIG. 10B, the user 102c may provide user input to the playback interface 125c that generates an instruction for the first medical device 110 to display the capnography waveform. In response to receipt of this instruction, the first medical device 110 may automatically display the capnography waveform. Alternatively, in response to receipt of this instruction, the first medical device 110 may prompt the user 102a to select the capnography waveform for display. For example, the first medical device 110 may provide the received instruction as user feedback at the first medical device 110 (e.g., the user feedback may include a visible and/or audible instruction). The processor 120 of the first medical device 110 may control the display 115 to display the capnography waveform at one or more of the operational interface 135 and the playback interface 125a in response to the received instruction.

As another example, at the playback interface 125c, the user 102c may review the ECG collected by the first medical device 110. The user 102c may notice a significant feature in the ECG over a time period during which medication was administered to the patient 101 by the caregiver 102a. The user 102c may provide a user input indicative of an instruction for the caregiver 102a to review the ECG at a time period selected by the user 102c. In response to receipt of this instruction, the first medical device 110 may automatically display the ECG on the playback interface 125a at the selected time period. Alternatively, in response to receipt of this instruction, the first medical device 110 may prompt the user 102a to review the ECG at the selected time period at the playback interface 125a. Additionally, the user input may include a note that the caregiver 102a should review the ECG prior to any further drug administration. The first medical device 110 may provide this note to the caregiver 102a via visible and/or audible feedback at the first medical device 110.

As an example of a usage scenario, the first medical device 110 may be inconveniently located for access to the playback interface 125a. For example, the first medical device 110 may be under a gurney, behind another person at the scene of the patient 101, and/or otherwise inconveniently located due to chaos, space constraints, and/or other limitations imposed by the scene of the patient. In such a situation, it may be more convenient to review the patient data at the playback interface 125c than at the playback interface 125a. As another example, the caregiver 102a may not have sufficient medical knowledge or may be too busy with treating the patient to utilize the playback interface 125a. In such a situation, the first medical device 110 may be in the operational interface only display mode rather than the combined operational/playback mode shown in FIG. 4A. Thus, the user 102c may determine and provide care information based on the review of the patient data at the playback interface 125c.

As another example of a usage scenario involving tiered care, the responders to an emergency may lack the training and/or the time to review patient data at the playback interface 125a. A medical supervisor and/or additional personnel may arrive at the scene to assist these responders. The medical supervisor and/or additional personnel may simply arrive at the scene, pull up the playback interface 125c on a mobile device, such as the computer tablet 310, and proceed to review and evaluate the patient data at the playback interface 125c without disruption of the use of the medical device 110.

Figure 4B:
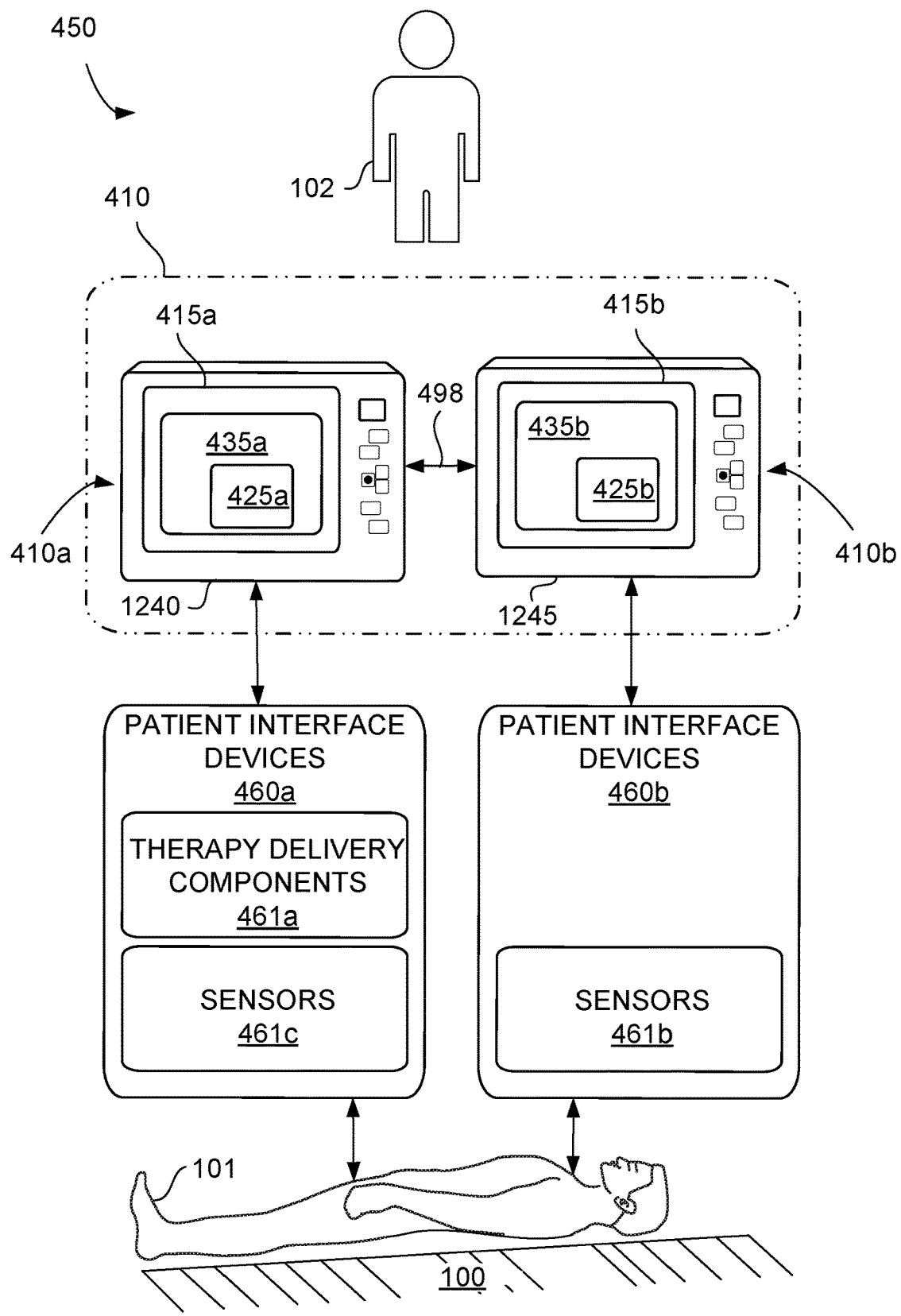
FIG. 4B shows an example of a system that includes a modular therapeutic medical device/patient monitor and provides the operational and playback interfaces.

Referring to FIG. 4B, a schematic diagram of an example of a system that includes a modular therapeutic medical device/patient monitor and provides the operational and playback interfaces is shown. The system 450 includes the modular therapeutic medical device/patient monitor 410 and patient interface devices 460a and 460b. As shown and discussed further below with regard to FIGS. 11 and 12, in an implementation, one or more of the medical devices 110 and 210 may be integrated therapy delivery/monitoring devices that include the single housing 1140 or 1145, respectively. Alternatively, the medical device 110 and/or 210 may be the modular therapy delivery/monitoring device 410 that includes at least a first housing 1240 and a second housing 1245. The first housing 1240 may surround, at least in part, components of the therapeutic medical device 410a configured to support therapy delivery and receive sensor signals via the therapy delivery components 461a and the one or more sensors 461c. The second housing 1245 may surround, at least in part, components of the patient monitor 410b configured to support patient monitoring via the one or more sensors 461b. In contrast to the components surrounded, at least in part, by the first housing 1240, the components surrounded by the second housing 1245 may exclude the components configured to support therapy delivery via the therapy delivery components 461a. The modular therapeutic medical device/patient monitor 410 may provide all or some of the functions and capabilities described herein with regard to the medical devices 110 and 210.

The modular therapeutic medical device 410 may provide the operational interfaces 435a and 435b and/or the playback interface 125. The operational interfaces 435a and 435b may include all or a portion of the functions and features of the operational interfaces 135 and/or 235 as described herein. In an implementation, the operational interfaces 435a and/or 435b may include additional and/or alternative features relative to the operational interfaces 135 and/or 235 based on the therapeutic and/or monitoring capabilities of the modular therapeutic medical device/patient monitor 410 relative to the first medical device 110 and/or the second medical device 210. The designations of "435a" and "435b" serve to indicate and differentiate between the host devices 415a and 415b.

In an implementation, the therapeutic medical device 410a may be a defibrillator and may be a professional defibrillator (e.g., an advanced defibrillator) and the patient monitor 410b may be an advanced critical care monitor. The dotted line associated with the index number 410 indicates that the therapeutic medical device 410a and the patient monitor 410b may be functionally joined but are not physically contained within a single housing. Rather, the therapeutic medical device 410a and the patient monitor 410b are disposed in the physically separate housings described above. As such, the therapeutic medical device 410a and the patient monitor 410b may be used together or individually as discussed further below.

The modular therapeutic medical device/patient monitor 410 may provide therapy and/or monitor the patient 101 via the patient interface devices 460a and 460b. The patient interface devices 460a and 460b may be substantially as described with regard to the patient interface devices 160. The patient interface devices 460a may include therapy delivery components 461a and/or sensor devices 461c.

In addition to therapy delivery the therapeutic medical device 410a may monitor the patient 101 (e.g., via the therapy delivery component(s) 461a and/or the sensor(s) 461c) and collect patient data that includes one or more of treatment data, sensor data, resuscitation/care data, and/or combinations thereof. The therapy delivery component(s) 461a may be substantially as described with regard to the therapy delivery component(s) 161a and the sensor device(s) 461c may be substantially as described with regard to the sensor device(s) 161b. The therapeutic medical device 410a may be configured to provide therapy to the patient 101 via one or more therapy delivery components 461a. In an implementation, the one or more therapy delivery components 461a may include defibrillation electrodes. The defibrillation electrodes may include and/or be configured to function as sensing electrodes. The sensors 461c may include sensing electrodes, for example, 12-lead electrodes configured to provide ECG data.

The patient monitor 410b may exclude therapy delivery capabilities and patient interface devices 460b may exclude therapy delivery components. The patient monitor 410b may be configured to monitor the patient 101 via the one or more sensors 461b. The patient monitor 410b may be configured to collect patient data that includes one or more of treatment data, sensor data, resuscitation/care data, and/or combinations thereof. The one or more sensors 461b may generate signals indicative of ECG and/or other cardiac parameters, ventilation and/or respiration parameters, drug and/or fluid delivery parameters, etc.

In an implementation, the patient monitor 410b may be configured to provide a different therapy to the patient 101 than the therapeutic medical device 410a. For example, the therapeutic medical device 410a may provide defibrillation therapy to the patient 101 and the patient monitor 410b may exclude the capability of providing defibrillation therapy but may be configured to provide ventilation therapy, drug and/or fluid delivery therapy, etc.

Although shown together in FIG. 4B, each of the therapeutic medical device 410a and the patient monitor 410b may perform all of their respective therapy and/or monitoring functions with or without the other of the therapeutic medical device 410a and the patient monitor 410b. Thus, the caregiver 102 may use the therapeutic medical device 410a alone (e.g., without the patient monitor 410b) or in combination with the patient monitor 410b. Similarly, the caregiver 102 may use the patient monitor 410b alone (e.g., without the therapeutic medical device 410a) or in combination with the therapeutic medical device 410a. For simplicity in FIG. 4B, the therapeutic medical device 410a and the patient monitor 410b are shown as corresponding to one patient 101. However, in an implementation, the therapeutic medical device 410a and the patient monitor 410b may correspond to two different patients since these devices may be used independently and do not have to be used in conjunction with one another. Thus, the therapeutic medical device 410a may provide therapy to and monitor a first patient and the patient monitor 410b may monitor a second patient.

The therapeutic medical device 410a and the patient monitor 410b may communicatively couple via a wired and/or wireless communication connection 498. The therapeutic medical device 410a and the patient monitor 410b may be configured to automatically pair with one another via the communication connection 498. Further, each of the therapeutic medical device 410a and the patient monitor 410b may be configured to share data with the other of the therapeutic medical device 410a and the patient monitor 410b via the communication connection 498. The therapeutic medical device 410a and the patient monitor 410b may be configured to provide therapy and monitor the same patient cooperatively via the communication connection 498.

The therapeutic medical device 410a and the patient monitor 410b may provide dual display screens 415a and 415b. One or more the display screens 415a and 415b may be a touchscreen and may be a pressure sensitive touchscreen. Each display screen 415a and 415b provides a respective operational interface 435a and 435b. Furthermore, at least one of the display screens 415a and 415b may provide the playback interface 425a and 425b, respectively. The playback interfaces referred to herein as 425a and 425b may include all or a portion of the functions and features of the playback interface 125 as described herein. The designations of "425a" and "425b" merely serve to differentiate between host devices (e.g., the devices 410a and 410b) of the playback interface 125 for clarity of description. The functionality and features of the first playback interface 425a may be the same as the second playback interface 425b. However, the visual representation of the patient data on the two devices 410a and 410b may be the same or may be different. Additionally, the portion of the patient data that is provided at the second playback interface 425b may be the same or may be different than the portion of the patient data that is provided at the first playback interface 425a.

In an implementation, the modular therapeutic medical device/patient monitor 410 may implement a particular display mode to selectively display the operational interfaces 435a and 435b and the playback interface 425a and 425b based on a functional relationship between the therapeutic medical device 410a and the patient monitor 410b with regard to criticality or priority of care. Processors of the devices 410a and 410b (e.g., the processors 420a and 420b described with regard to FIG. 12) may assign a priority level to therapy and/or monitoring provided by each device and implement the display mode based on this assigned priority level. The processor of one of the devices 410a and 410b may evaluate the priority of care relative to the other of the devices 410a and 410b.

Table 6 below shows an example of a priority of care evaluation with regard to the display mode for each of the dual displays 415a and 415b. In this example, both units 410a and 410b are associated with the same patient and communicatively coupled to one another. The therapeutic medical device 410a is coupled to the patient via defibrillation electrodes. The patient monitor 410b is not configured to deliver therapy to the patient therefore "therapy delivery component coupled to patient" is not applicable to the patient monitor 410b. As shown in this example, because the therapeutic medical device 410a is coupled to the patient for the delivery of defibrillation, this unit provides critical therapeutic care relative to the patient monitor which does not provide any therapeutic care. Further, because the therapeutic medical device 410a is coupled to the patient for the delivery of defibrillation, the processor 420a may prohibit implementation of the playback interface only mode for the display screen 415a.

TABLE 6

Modular Therapeutic Medical Device/Patient Monitor

|  | Therapeutic Medical Device | Patient Monitor |
| --- | --- | --- |
| Same patient? | yes | yes |
| Communicatively coupled? | yes | yes |
| Therapy delivery component coupled to patient? | yes | N/A |
| Type of therapy | defibrillation | none |
| Sensors coupled to patient | yes-ECG 12 lead | yes-pulse oximetry |
| Critical care? | yes | no |
| Available display mode(s) | O, O/P | O, O/P, P |
| Combined mode configuration | P inset | O inset or P inset |

Table 7 below shows another example of a priority of care evaluation with regard to the display mode for each of the dual displays 415a and 415b. In this example, the therapeutic medical device 410a is not coupled to the patient. Therefore, the patient monitor 410b may provide critical monitoring care to the patient relative to the therapeutic medical device 410a. As a result, the processor 420a of the therapeutic medical device 410a may enable a playback only mode for this device and the playback interface 425a may provide patient data collected by the patient monitor 410b.

TABLE 7

Modular Therapeutic Medical Device/Patient Monitor

|  | Therapeutic Medical Device | Patient Monitor |
| --- | --- | --- |
| Same patient? | yes | yes |
| Communicatively coupled? | yes | yes |
| Therapy delivery component coupled to patient? | no | N/A |
| Type of therapy | none | none |
| Sensors coupled to patient | no | yes-pulse oximetry & 12 lead ECG |
| Critical care? | no | yes |
| Available display mode(s) | P | O, O/P, P |
| Combined mode configuration | N/A | O inset or P inset |

The above tables are examples only and other priority of care evaluations and display mode controls are within the scope of the disclosure.

Figure 5:
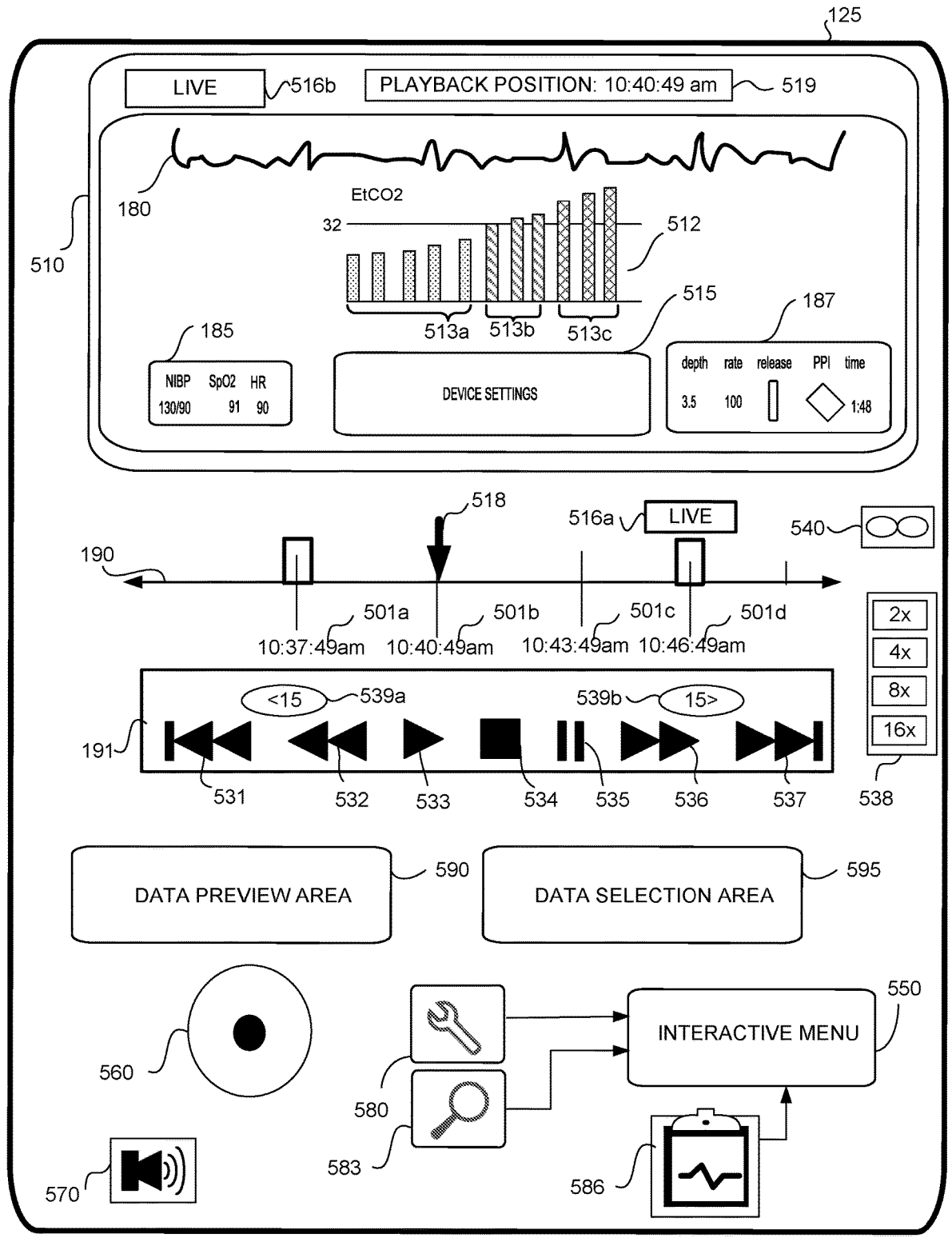
FIG. 5 shows a schematic diagram of an example of the playback interface.

Referring to FIG. 5, a schematic diagram of an example of the playback interface is shown. As discussed above, various devices may host the playback interface 125. For example, as discussed above, the medical device 110, the medical device 210, and/or the computing device 310 may serve as a host device and provide the playback interface 125 (e.g., the playback interface 125a, 125b, 125c) at an output device (e.g., the displays 115, 215, and 315) of the host device. The processor of the host device (e.g., the processor 120, 220, or 320) may control the respective display screen to display the playback interface 125 at the display screen. Additionally or alternatively, the host device may provide at least a portion of the treatment provided at the playback interface 125 via an output device other than a display, for example, as audible information from speaker (e.g., the speaker 170).

The playback interface 125 may include a data display window 510. The data display window 510 may be configured to display one or more visual representations of the patient data. For example, the data display window 510 may display visual representations of a physiological waveform/time trend 180 and/or of a discrete physiological measurement 185 and/or of CPR performance data 187.

The physiological waveform/time trend 180 may provide a visual representation of trending data from signals indicative of a physiological parameter such as for example, ECG, systolic blood pressure, end tidal carbon dioxide (EtCO2), blood oxygen saturation (SpO2), etc. Trending data may be displayed as a running record of previous readings. The oldest readings may appear on the left, and the newest readings may appear on the right. The newest reading may be inserted on the right side while displacing the oldest reading on the left side. Alternatively, the oldest readings may appear on the right and the newest readings may appear on the left. The newest reading may be inserted on the left side while displacing the oldest reading on the right side.

Other options for visually indicating the trend data for a given signal may be employed. For example, a time trend for EtCO2 is shown as a bar graph 512.

In an implementation, the playback interface 125 may scale the time trend data, adjust the frequency of the values displayed for the time trend data, and/or adjust a pattern and/or color with which the trending values are displayed according to the particular patient and/or the patient's condition. These features may convey information about how the trending values compare with acceptable values or ranges of values, or user-defined values or ranges of values. For example, in the bar graph 512, the playback interface 125 may display the five bars 513*a* on the left with a first pattern and/or color to indicate that the patient's EtCo2 at the times corresponding to those particular measurements was or is at a critical level far below acceptable ranges. The playback interface 125 may display the middle three bars 513*b* with a second pattern and/or color to indicate that EtCo2 at the times corresponding to those particular measurements was or is below acceptable limits, but not at a critical level. The right three bars 513*c* may exhibit a third pattern and/or color to indicate that the patient's EtCo2 at the times corresponding to those particular measurements was within acceptable limits for the patient's age. The color of other information on the playback interface 125 may change based on a target and/or desired range for a particular parameter. Further the playback interface 125 may display a target value and/or a range (e.g., with a numerical indicator and/or a graphical indicator).

In an implementation, the data display window 510 may include a device settings window 515. The device settings window 515 may provide device settings associated with the displayed patient data based on time. The device settings may correspond to the settings, status, activities, etc. of the device that collected the displayed patient data at the time corresponding to the displayed patient data. For example, the device setting window 515 may provide battery status information, heart rhythm analysis information, shock delivery information, and/or other therapy delivery information. The shock delivery information and/or the therapy delivery information may correspond to the device settings at the time of shock or other therapy delivery (e.g., energy, flow rate, start time, stop time, compression rate, compression depth, etc.). For example, the device settings window 515 may provide at least a portion of the information in Table 8 below. Such information may enable the user of the playback interface 125 to evaluate the displayed patient data in light of the device settings, status, and/or activities at the time of data collection.

The playback interface 125 may include an interactive timeline 190. The information provided in the data display window 510 may correspond to a time as indicated by the interactive timeline 190. The interactive timeline 190 is shown as a substantially linear timeline however this is an example only and other non-linear timelines are within the scope of the disclosure. The times (e.g., 501*a*, 501*b*, 501*c*, 501*d*) represented on the interactive timeline 190 are representative of the time stamps associated with the sensor data. Each time stamp may be an absolute clock time or an elapsed time. For example, the elapsed time may be an elapsed time from a particular event within the medical encounter such as turn-on of the device, a first ECG of the patient, a defibrillation shock administration, a drug delivery, a pacing therapy administration, etc.

Figure 6A:
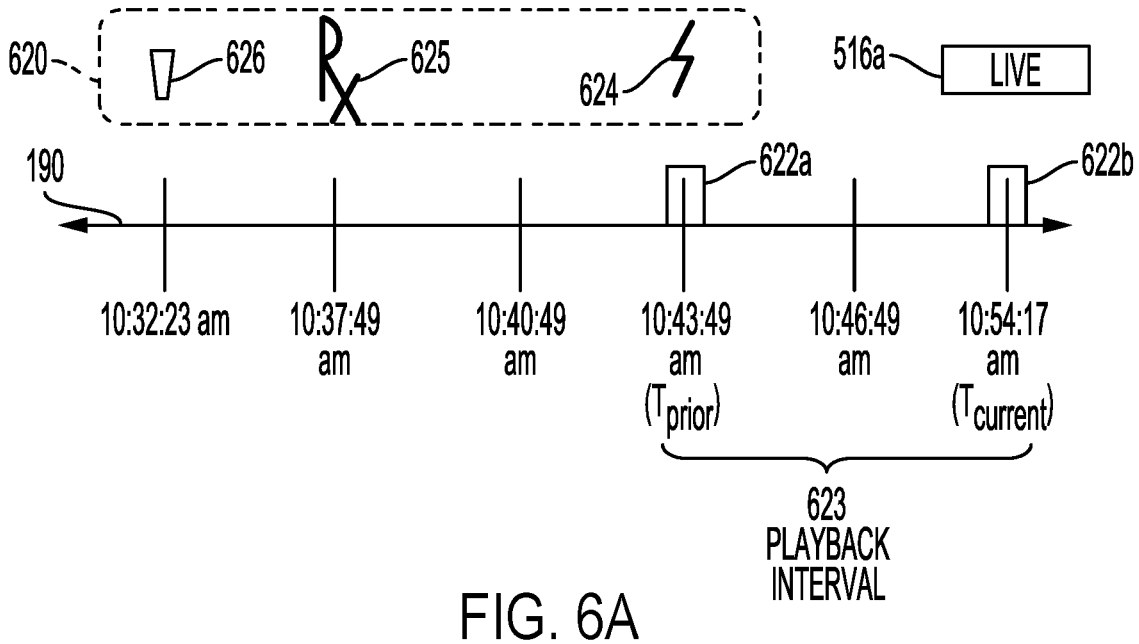
FIG. 6A shows an example of interactive timeline features.

Referring to FIG. 6A, an example of interactive timeline features is shown. The interactive timeline 190 may include visual event indicators 620. In various implementations, the visual event indicators 620 may correspond to medical events and/or device events. The visual event indicators 620 may include graphic icons, textual annotations, or a combination thereof. The visual event indicators 620 may also be referred to as code markers.

For example, the visual event indicators 620 shown in FIG. 6A include a defibrillation indicator 624, a drug administration indicator 625, and a bronchodilator indicator 626. The shape of the icons used for the visual event indicators 620 may be indicative of a type of code marker. For example, the lightning bolt (e.g., indicator 624) may represent shock events and the Rx symbol (e.g., indicator 625) may represent drug administration events. Although an example of one of each type of visual event indicator is shown in FIG. 6A for simplicity, the interactive timeline 190 may include one or more of the various types of the visual event indicators 620. These types of event indicators are examples only and not limiting of the disclosure as the visual event indicators 620 may include other or additional types of event indicators for various medical events.

In an implementation, the medical events represented by the visual event indicators 620 may be delivered therapy events and/or physiological patient events. For example, delivered therapy events may include therapy administered by a person (e.g., manual chest compressions, medications, intubation, ventilation, etc.) and/or therapy administered by a machine (e.g., automated chest compressions, automated drug infusions, electrotherapy, ventilation, etc.). The physiological patient events may be measured events and/or events observed by a caregiver. For example, measured events may include physiological measurements made with a physiological sensor, such as, for example, a pulse oximetry measurement, a wired and/or wireless ECG, a blood pressure, a glucose measurement (e.g., from a wired and/or wireless glucose monitor), a temperature measurement, etc. The observed events may include physiological events that are observed as a result of a caregiver evaluation rather than a sensor measurement. For example, return of spontaneous circulation (ROSC), a coma score, a pain score, difficulty breathing, etc. The caregiver may assign a qualitative value to the observed event but the observed events may not be measurable via the sensor.

In an implementation, the medical events that may be represented by the visual event indicators 620 may be events triggered, recognized, and/or identified by medical device detection and/or identification algorithms. Such events may include, for example, but not limited to, return of spontaneous circulation (ROSC) detection, ventricular fibrillation (VF) detection, a re-arrest detection, and a sepsis detection. The ROSC, VF, and re-arrest detection may occur based on an EKG analysis algorithm and the sepsis detection may occur based on a vital signs or protocol analysis algorithm. The medical events may also include user alerts and/or notifications and may include advisory messages to change and/or modify a therapy or provide a new or different therapy to the patient. Further, the medical events may include protocol timeline markers that may indicate a position within a protocol. The medical events may further include diagnostic tests such as point-of-care laboratory measures, patient vital signs, temperature, and/or diagnostic imaging and/or videos.

In an implementation, the device events represented by the visual event indicators 620 may be a status event and/or operation event of the medical device. For example, the status event may include a low battery, an expired electrode or other consumable, etc. The operation event may include an analyzed heart rhythm, a communication coupling, an electrode attachment, a shock delivery time, a shock duration, a shock energy, etc. Device events may further include, for example, one or more of the occurrence of an alarm (e.g., a monitor-generated alarm such as a heart rate or other arrhythmia alarm), the acquisition of a medical measurement or signal (which may be helpful for documenting at the end of a medical event), and a time at which a "rearrest" soft-key was pressed. For example, a user of the medical device may press a "rearrest" soft-key at a time at which a renewed or subsequent cardiac arrest condition is observed.

In an implementation, the patient data may include the code markers but may only provide the visual event marker 620 in response to a user request. For example, the user may select a time and/or a time interval on the interactive timeline 190 and playback interface 125 may display the code markers associated with the patient data for the selected time and/or time interval. The playback interface 125 may display the code markers graphically (e.g., on the interactive timeline) and/or as a list that may include the code marker and the time associated with the code marker. As described above, the code markers may include device events. This may provide the advantage of enabling the user of the playback interface 125 to evaluate the patient data in view of particular device conditions existing at the time of patient data collection. In an implementation, the interactive timeline 190 may include times associated with emergency services events such as, for example, but not limited to, a time of cardiac arrest and/or other emergency event, a time of a 911 call, a time of dispatch, and/or other emergency dispatch and/or electronic patient care record data.

Further examples of data, parameters, and/or events that may correspond or be represented by visual event indicators 620 and/or code markers include one or more clinical events as summarized in Table 8 below. The parameters may include one or more of heart rate, oxygen saturation, pulse rate, end tidal carbon dioxide, non-invasive blood pressure, invasive blood pressure, temperature, change in temperature, blood carbon monoxide level, blood methomoglobin level, total hemoglobin in blood, blood oxygen content, a perfusion index indicative of an arterial pulse signal strength, and a measurement indicative changes in the perfusion index during respiration. The information in Table 8 is an example only and not limiting of the disclosure as other data, parameters, and/or events are within the scope of the disclosure.

TABLE 8

| Category | Sub-Category |
| --- | --- |
| Foreground analysis | Start shock advisory analysis |
| | Shock advisory result |
| | Individual segment result |
| | Halt shock analysis due to error |
| Defibrillation | Synchronization state |
| | Selected energy |
| | Delivered energy |
| | Device impedance |
| | Patient impedance |
| | Number of shocks |
| CPR | Compression rate |
| | Compression depth |
| Alarms | High parameter alarm |
| | Low parameter Alarm |
| | No breath |
| | Alarm activation |
| | Alarm deactivation |
| | Alarm limit change |

TABLE 8-continued

| Category | Sub-Category |
| --- | --- |
| Life threatening alarms | Asystole |
| | Ventricular fibrillation or Ventricular tachycardia |
| | Extreme bradycardia |
| | Extreme tachycardia |
| Twelve lead data | ECG data |
| | Analysis result |
| | Patient demographic |
| | Parameter values |
| Treatment markers | System defined |
| | User defined |
| | Drug Delivery |
| | IV |
| | Sedation |
| | CPR |
| | Oxygen delivery |
| | Intubation |
| | Glucose delivery |
| | Fluid delivery |
| Pacer mode | Enter pacer mode |
| | Exit pacer mode |
| | Change pacer rate |
| | Change pacer current |
| Other | Background analysis for advised shock |
| | Change in parameter value |
| | Enter manual mode from AED mode |

As shown above, the treatment markers may include drug delivery. The treatment marker may record the action of delivering the drug along with the name of the drug delivered (e.g., epinephrine, atropine, phenobarbitol, aspirin, morphine, naloxone hydrochloride, diazepam, nitro-glycerin, beta-blockers, Atrovent®, and/or other drugs that provide a rapid response to a code condition). The delivered drugs may include pharmacological treatments for cardiac conditions, respiratory conditions, psychological conditions, allergy, drug overdose, diabetes, fluid control (e.g., a diuretic), pain, etc.

In an implementation, the playback interface 125 may automatically generate the visual event indicators 620. For example, the processor of the device providing the playback interface may generate the visual event indicators 620 in response to machine administered therapy, measured physiological event, and/or device events. In an implementation, the user may request a new visual event indicator 620 via a user input to the playback interface 125. Additionally or alternatively, the user may provide an annotation for the interactive timeline 190 as an event indicator.

Referring further to FIG. 6A, in an implementation, the interactive timeline 190 may include one or more data window time selectors 622a and 622b (e.g., a first time selector and a second time selector). The time selectors 622a and 622b may define a playback interval 623. The playback interval 623 may be, for example, an interval of time over which the data display window 510 provides patient data associated with the time stamps during this interval of time. In an implementation, the user may position the first time selector 622a to set a start time for the playback interval 623 and may position the second time selector 622b to set an end time for the playback interval 623. Although this playback interval is shown in FIG. 6A as including the current time, the playback interval 623 may exclude the current time and may only include times prior to the current time. In this case, the patient data associated with the playback interval 623 may only include historical data and may not include real-time data. In an implementation, the timeline 190 may include the first time selector 622a and not include the second time selector 622b. In such an implementation, the playback interval 623 may start at the first time selector 622a and automatically end at the current time.

In an implementation, the playback interface 125 may include a snap-to-event feature. For example, the user may position the first time selector 622a and/or the second time selector 622b and provide input to the media navigation bar 191. For instance, the user may press the play control 533 to begin data playback. In response to the input to the media navigation bar 191, the playback interface 125 may move one or more of the first time selector 622a and the second time selector 622b to a nearest event marker 620. In this way, the playback interface 125 may snap the particular time selector to the event marker.

The playback interface 125 may then implement the input to the media navigation bar 191 from the snapped to event marker. For example, if the input is "play" then the playback interface 125 may play the data starting at the snapped to event marker. As another example, if the input is rewind (e.g., control 532 or 531), the playback interface 125 may rewind from the snapped to event marker. In an implementation, if the first time selector 622a or the second time selector 622b is within a threshold time interval of the current time, the playback interface 125 may automatically snap the particular time selector to the current time and provide real-time playback. Alternatively, if the first time selector 622a or the second time selector 622b is within a threshold time interval of the event marker 620 time, the playback interface 125 may automatically snap the particular time selector to the event marker 620 time. The threshold time interval for this snap-to-current feature may be a predetermined time interval such as 1 second, 2 seconds, 3 seconds, 5 seconds, 10 seconds, 15 seconds, 30 seconds, etc. In an implementation, the predetermined time interval may be a user configurable time interval.

Figure 6B:
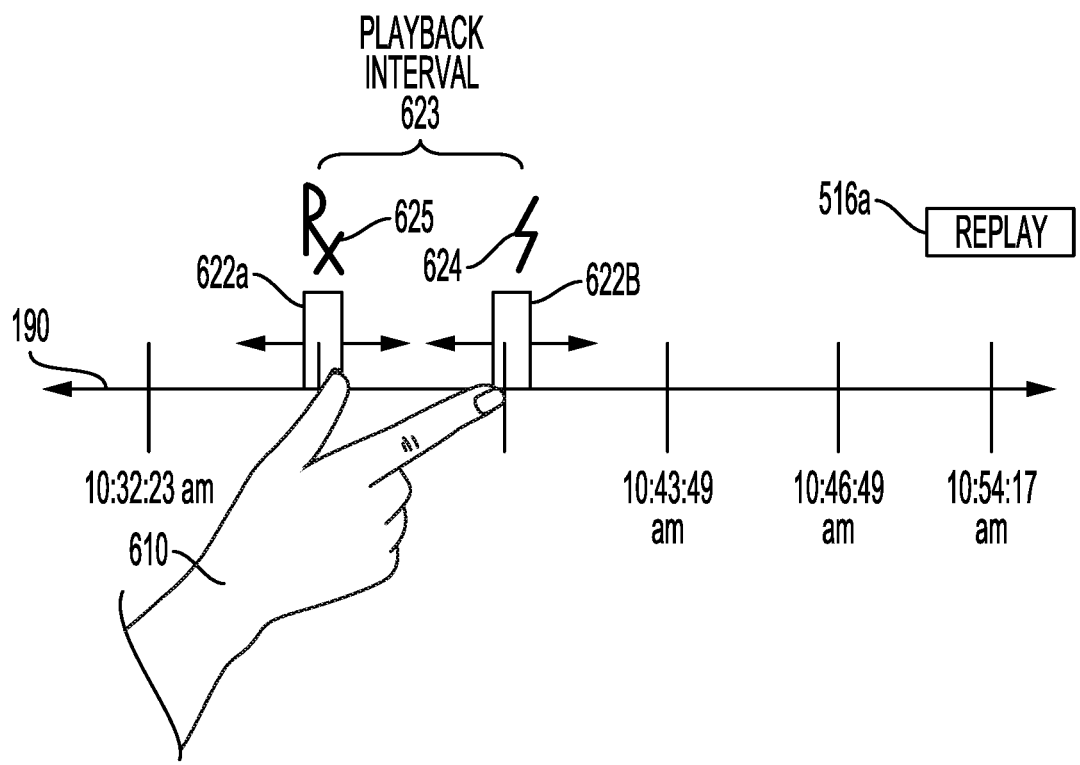
FIG. 6B shows an example of touchscreen control of the playback interface.

Referring to FIG. 6B, an example of touchscreen control of the playback interface is shown. In an implementation, the playback interface 125 may capture a touchscreen gesture 610 to determine the playback interval 623. As an example, the interactive timeline 190 may recognize as input the two times indicated by each finger of the caliper gesture and set these times as the boundaries of the playback interval 623. As another example, the user may use the touchscreen gesture 610 to drag or slide the time selectors 622a and 622b along the interactive timeline 190. In an implementation, the time selectors 622a and 622b and/or other features on the playback interface 125 may capture input via a push gesture that exerts sufficient pressure on the display screen 115 to interpret the input as a push gesture.

In an implementation, the playback interface 125 may provide looped playback of the patient data over the playback interval 623. For example, the looped playback may improve recognition by the user of the playback interface 125 of changes in ECG morphology due to delivery of nitroglycerin or changes in end tidal carbon dioxide as a result of delivery of a bronchodilator. Thus, the playback interface 125 may provide the patient data from the start time of the playback interval 623 to the stop time of the playback interval 623 and then repeat this playback at the start time of the playback interval 623 to provide the data loop. The playback loop may repetitively playback the data over the playback interval 623. In an implementation, the playback interface 125 may include a loop control 540 (e.g., as shown in FIG. 5) that may control the loop playback (e.g., start the playback, stop the playback, capture input indicating a number of repetitions, etc.). The playback loop may be played back at an adjustable speed and loop interval duration.

Referring further to FIG. 6B, in an implementation, the user may set the playback interval 623 based on a selection of one or more visual event indicators 620. For example, the playback interval 623 may be associated with a first visual event indicator (e.g., the indicator 625) and a second visual event indicator (e.g., the indicator 624). Thus, the playback interface 125 may be configured to play back patient data corresponding to the intervening time between the two selected indicators. In the example of FIG. 6B, the playback interface 125 may playback data collected by the medical device 110 between delivery of a drug and a subsequent defibrillation. For example, if the patient is experiencing chest pain, the first visual event indicator selected may be a code marker for delivery of nitroglycerine.

In an implementation, the playback interval 623 may include a time interval prior to and/or subsequent to the time associated with the visual event indicator 620 and/or a code marker. For example, the playback time interval may specify that the playback of data associated with the selected visual event indicator 620 begin with data associated with a time such as 1 second, 2 seconds, 5 seconds, 10 seconds, 15 seconds, 30 seconds, 60 seconds or another suitable time interval prior to the time stamp of the selected visual event indicator 620. In this way, the user of the playback interface 125 may review and/or analyze medical data leading up to the event associated with the selected visual event indicator 620. Similarly, the playback time interval may specify that the playback of data associated with the selected visual event indicator 620 end with data associated with a time, for example, of 1 second, 2 seconds, 5 seconds, 10 seconds, 15 seconds, 30 seconds, 60 seconds, 2 minutes, or another time interval after the time stamp of the selected visual event indicator 620. In this way, the user of the playback interface 125 may review and/or analyze medical data subsequent to the selected visual event indicator 620.

Selection (e.g., by tapping, clicking, pressing, and/or another method of providing input to the playback interface 125) of a visual event indicator 620 may also result in specific information relevant to that visual event indicator 620 appearing in the data display window 510. For instance, if the drug administration icon 625 is associated with an intervention using a bronchodilator then the data provided in the data display window 510 might be the end tidal carbon dioxide waveform, heart rate, spirometric data, and/or other ventilator, ventilation, and/or respiratory flow parameters and waveforms. This data may provide an indication of whether or not the intervention has improved the patient condition. As another example, selection of the drug administration event indicator 625 may initiate playback of relevant parameters such as capnography or airway flow data (e.g., spirometry data). The playback may enable an evaluation of a patient response to an administration of nitroglycerine, a bronchodilator, and/or adrenaline, for instance. As further example, a selection of the shock visual event indicator 624 may initiate playback of ECG waveform data corresponding to the selected shock.

The interactive timeline 190 may further include a temporal label 516a. The temporal label 516a indicates whether or not the data associated with a position of the time selector 622b is real-time data or historical data. The user of the playback interface 125 may interact with the playback interface 125 to select time periods of interest and review the treatment data corresponding to the selected time frames. These time periods may include the historical data, the real-time data, or combinations thereof. As the processor 120 processes sensor signals to determine and collect sensor data, the processor 120 may associate time stamps with the sensor data. The patient data may include the sensor data and the associated time stamps. Time stamps corresponding to a current and/or near-current time may correspond to real-time data (e.g., a real-time portion of the patient data). The near-current time may correspond to a time within a near-current time interval from the current time. For example, the near-current time interval may be 0-1 second, 0-2 seconds, 0-3 seconds, 0-4 seconds, 0-5 seconds, 0-6 seconds, 0-7 seconds, 0-8 seconds, 0-9 seconds, 0-10 seconds, 0-11 seconds, 0-12 seconds, 0-13 seconds, 0-14 seconds, or 0-15 seconds from the current time. In an implementation, the near-current time interval may be user-configurable. The near-current time interval may correspond to a delay time due to data transmission (e.g., communication channel latency) and/or data processing delays (e.g., time associated with processing speed). In some instances, time stamps greater than the near-current time interval prior to the current time may correspond to historical data (e.g., a historical portion of the patient data). The time stamps may include a range of times beginning at a start time of data collection for a case by the medical device 110 that is prior to the current time and ending at the current time. The case may be a patient case and data collection for the case may correspond to data collection for a particular patient. The historical data may be the sensor data associated with time stamps greater than the near-current time interval from the current time and less than or equal to a start time of data collection for the case by the first medical device 110. In an implementation, if the near-current time interval exceeds a predetermined threshold (e.g., a live playback threshold) of, for example 1, 2, 3, 4, 5, 6, 7, 8, 9, 10, 11, 12, 13, 14, or 15 sec then the patient data may correspond to historical data provided in a replay mode as opposed to current data provided in a live mode. In some implementations, the predetermined threshold may be 50 milliseconds, 100 milliseconds, 0.5 seconds, 1 second, 2 seconds, 3 seconds, or 5 seconds. Conversely, time stamps less than or equal to the predetermined threshold may correspond to real-time data (e.g., data provided in the live mode). In an implementation, the medical device 110 may store the sensor data with the associated time stamps in a memory (e.g., the memory 121 as shown for example in FIG. 11).

As the processor 120 processes sensor signals to determine and collect sensor data, the processor 120 may associate time stamps with the sensor data. The treatment data may include the sensor data and the associated time stamps. Time stamps within 0-3 seconds of a current time correspond to real-time data (e.g., a real-time portion of the treatment data). Time stamps greater than a predetermined threshold (e.g. greater than 3 seconds) prior to the current time correspond to historical data (e.g., a historical portion of the treatment data). Time stamps less than or equal to a predetermined threshold correspond to real-time data. The time stamps may include a range of times from a start time of data collection for the case by the medical device 110 to the current time. The historical data is the sensor data associated with time stamps greater than a predetermined threshold prior to current time and less than or equal to a start time of data collection for the case by the first medical device 110. In an implementation, the medical device 110 may store the sensor data with the associated time stamps in a memory (e.g., the memory 121 as shown for example in FIG. 11).

For example, if the time selector 622b is positioned at the time $T_{current}$, then temporal label 516a may indicate that the data is real-time data (e.g., a "LIVE" label as shown in FIGS. 5 and 6A). $T_{current}$ may correspond to a current time of sensor data acquisition at the medical device 110. Thus, the patient data displayed by the data display window 510 at a time corresponding to $T_{current}$ may be substantially real-time data. The data display window 510 may include a temporal status field 516b that corresponds to the temporal label 516a. Thus, as shown in FIG. 5, when the temporal label 516a indicates "LIVE," the temporal status field 516b also indicates "LIVE." "LIVE" is an example only and not limiting of the disclosure. The temporal label 516a and/or the temporal status field 516b may include another textual and/or graphic indicator that the visual representation of data in the data display window 510 is real-time data.

As an alternative to real-time data, the data displayed in the data display window 510 may be historical data collected by the medical device 110 prior to the current time. The times $T_{prior}$ along the interactive timeline 190 that are prior to $T_{current}$ may be times at which patient data was previously captured by the medical device 110. For example, the temporal label 516a may display "REPLAY" (e.g., as shown in FIG. 6B) for historical data (e.g., non real-time data). When the temporal label 516a indicates "REPLAY," the temporal status field 516b may also display "REPLAY." "REPLAY" is an example only and not limiting of the disclosure. The temporal label 516a and/or the temporal status field 516b may include another textual and/or graphic indicator that the visual representation of data in the data display window 510 is historical data and is not real-time data.

In an implementation, the operational interface 135 and the playback interface 125 may both display the same real-time patient data associated with the "LIVE" temporal label. The visual representations of the same real-time patient data may be the same on both interfaces 135 and 125 or may be different. Thus, for the same real-time patient data, the images of this data generated for display at the playback interface 125 may differ from those generated for display at the operational interface 135. Thus the visual representation of the patient data at the playback interface 125 may not be a replication of the visual representation of the same patient data at the operational interface 135.

In a further implementation, the operational interface 135 may display real-time data and the playback interface 125 may display historical data. The visual representation of the historical data on the playback interface 125 may appear to be the same as the visual representation of this data when it was previously displayed in real-time at the operational interface 135. Alternatively, the visual representation of the historical data on the playback interface 125 may appear to be different from the visual representation of the data when it was previously displayed in real-time at the operational interface 135. For example, the rendering of the historical data as compared to real-time data may differ (e.g., color, textual font, size, style, etc.) so that it is clearly distinct to a viewer whether the representation is historical or real-time. Thus, for the same historical patient data, the images generated for display at the playback interface 125 may differ from those generated for display at the operational interface 135.

Figure 7A:
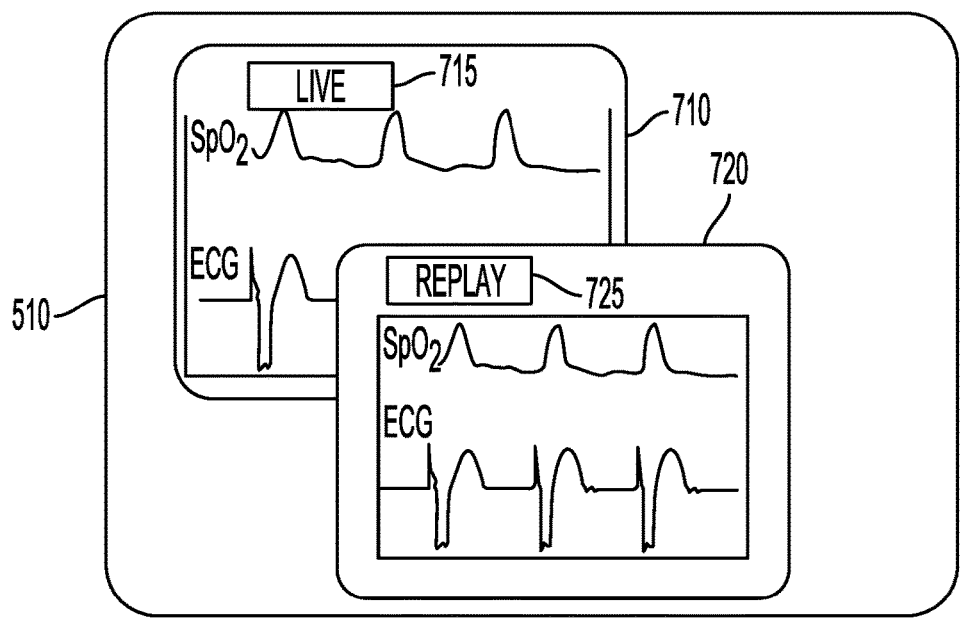
FIG. 7A shows an example of multiple temporal windows on the playback interface.
Figure 7B:
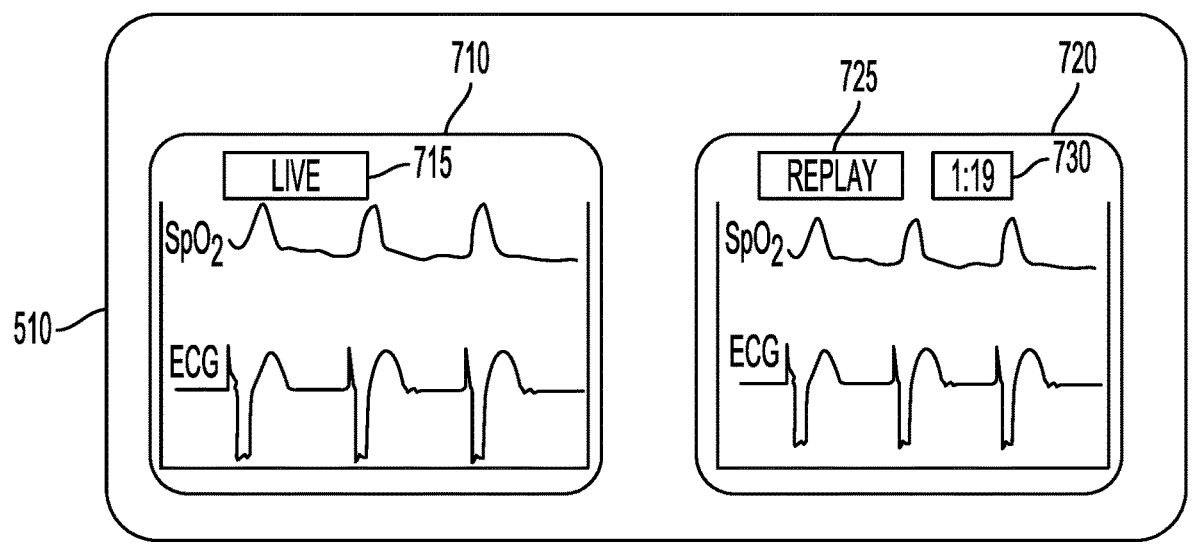
FIG. 7B shows another example of multiple temporal windows on the playback interface.

Referring to FIGS. 7A and 7B, with further reference to FIGS. 5-6B, an example of multiple temporal windows on the playback interface is shown. In an implementation, the data display window 510 may provide the multiple temporal windows. The multiple temporal windows may include one or more real-time windows 710 (e.g., the "LIVE" window as indicated by the temporal status field 715) and one or more historical windows 720 (e.g., the "REPLAY" window as indicated by the temporal status field 725). The multiple temporal windows may be displayed with overlap as shown, for example, in FIG. 7A or without overlap as shown, for example, in FIG. 7B. In various implementations, the multiple temporal windows may include a combination of real-time and historical windows, all historical windows, or all real-time windows. Multiple real-time windows may include different real-time data and/or different visual representations of the real-time patient data. In an implementation, the "REPLAY" window may include a time delay indicator 730 that displays a time span (e.g., an amount of time) between the displayed data and the current time. The time delay indicator 730 may indicate how old the displayed data is relative to the current time.

Figure 8:
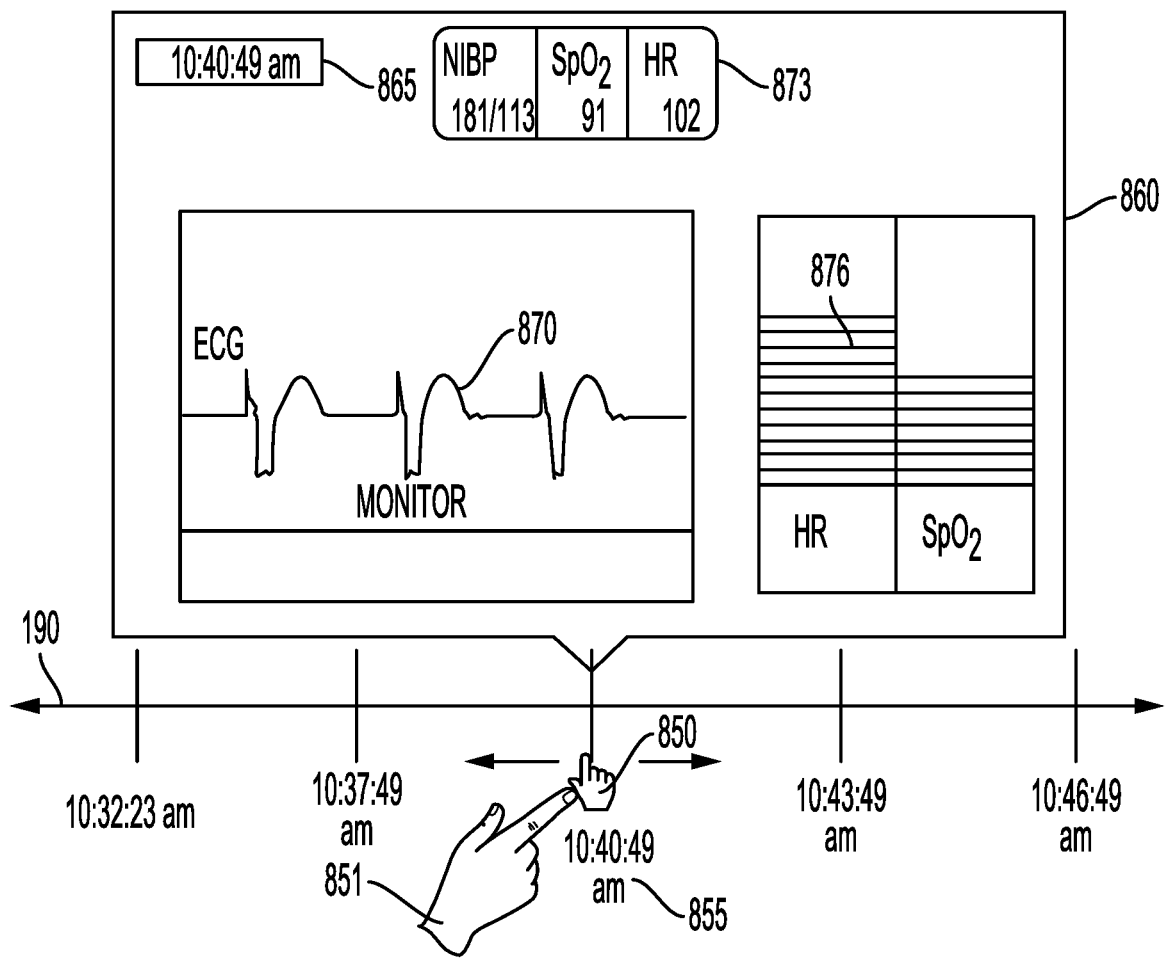
FIG. 8 shows an example of an on-screen cursor for the interactive timeline.

Referring to FIG. 8, with further reference to FIG. 5, an example of an on-screen cursor for the interactive timeline is shown. In an implementation, the interactive timeline 190 may include an on-screen cursor 850. For example, the on-screen cursor 850 may take the form of a hand with a pointed finger. However, this form is an example only and other cursor icons and/or representations are within the scope of the disclosure. The user of the playback interface 125 may provide input (e.g., via the one or more input device(s) 144, 244, or 344 shown in FIG. 11) and this input may determine a position of the on-screen cursor 850 along the interactive timeline 190.

In an implementation, the display that provides the playback interface 125 may be a touchscreen. The user may place his or her finger 851 on the on-screen cursor 850 and move the on-screen cursor 850 along the touchscreen in response to a movement of the user's finger 851 along the touchscreen. With this or another touchscreen gesture, the user may position the on-screen cursor 850 at a particular timeline position (e.g., a user-selected position) in order to select the time associated with this position as the time for patient data playback. In various implementations, the user of the playback interface 125 may click, double click, tap, double tap, and/or provide another input to the interactive timeline 190 to activate the on-screen cursor 850. Though, it can be appreciated that for certain embodiments such as where the playback interface 125 is a touchscreen, an on-screen cursor is not a required element.

In an implementation, the user may provide an input (e.g., a touchscreen gesture such as a press or tap on the on-screen cursor 850) to activate a preview pop-up window 860. The preview pop-up window 860 may provide a visual representation of the patient data that includes sufficient detail for the user to determine whether to select a time period for playback that includes the particular timeline location corresponding to the pop-up window. For example, the ECG displayed in the pop-up window may exhibit features representative of bradycardia or another relatively easily observable ECG feature. In response to viewing this ECG feature, the user may decide to view discrete physiological values over this time period, for example the end tidal carbon dioxide values to try to determine the cause of and/or effective medical interventions for the condition represented in the ECG.

In some implementations, the playback interface 125 displays the preview pop-up window 860 above or to the side of a location or area on the touchscreen corresponding to a location of one or more of the user's digits (e.g., thumb, fingers). The touchscreen is configured to recognize the location of the one or more of the user's digits. In this manner, the information provided in the preview pop-up window 860 may be unobstructed by the user's digits. Additionally or alternatively, in an implementation, the preview pop-up window 860 may be located proximate to the on-screen cursor 850 and/or the interactive timeline 190. The playback interface 125 may approximately vertically align the preview pop-up window 860 with the playback pointer 518. In some implementations, the on-screen cursor 850 may replace the playback pointer 518, or vice-versa. The information displayed in the preview pop-up window 860 may include patient data and/or device state information that corresponds to the time indicia of the playback pointer 518 and/or the on-screen cursor 850.

In an implementation, the user of the playback interface 125 may slide the on-screen cursor 850 along the interactive timeline 190 to determine and change the contents of the preview pop-up window 860. In some implementations, if the display 115 is the pressure sensitive touchscreen, then in response to a pressure on the screen in excess of a pressure threshold (e.g., a pressure in excess of approximately 0.2-0.3 lbs.), the playback interface 125 may increase a size of the preview pop-up window 860 (e.g., increase an area of the display screen 115 occupied by the preview pop-up window 860). In some implementations, the size of the preview pop-up window 860 may be proportional to the amount of force in an approximately linear fashion. In various implementations, the pressure threshold may be 0.5, 1, 2, 3, 4 or 5 pounds of force. In some implementations, there may be multiple thresholds that cause enlargement of the preview pop-up window 860 to increase in size in a step-wise fashion in response to an increase in pressure on the touchscreen. For example, as the pressure on the touchscreen increases and exceeds additional thresholds of the multiple thresholds, the size of the preview pop-up window 860 may increase relative to a previous size.

In some implementations, the preview pop-up window 860 may be too small to adequately display all of the patient data corresponding to the time indicia of the playback pointer 518 or on-screen cursor 850. In such cases, the playback interface 125 may prioritize the patient data according to predetermined criteria. The playback interface 125 may display the patient data at the pop-up window 860 according to the determined priority and a current size of the preview pop-up window 860. For example, the playback interface 125 may display a single data element with the highest priority if there is only space to display the single data element in the preview pop-up window 860. With progressively larger preview pop-up windows 860, the playback interface 125 may display additional data elements in order of their predetermined priority. For instance, heart rate information may have the highest priority, oxygen saturation next higher, followed by, in order, end tidal carbon dioxide, EGC waveform, pulse oximetry waveform. In some implementations, the priority order may be a default priority for the playback interface 125. In some implementations, the playback interface 125 may automatically modify the priority order from the default order and/or capture user input to modify the priority order from the default order. The priority order may depend on the state of the medical device 110. For example, if the medical device 110 is in a defibrillation mode (e.g., the defibrillation electrodes are attached to the patient, an ECG analysis is underway, a device log indicates a recent electrotherapy delivery, etc.), then the playback interface 125 may change the second priority data element from oxygen saturation to end tidal carbon dioxide. As described below, the playback interface 125 may enable the user to play back data based on a specific medical condition of the patient. The user may select the medical condition via one or more of the event indicators 620 and/or a medical condition selection control 586. For instance, if the user selects myocardial infarction (heart attack), the priority may be adjusted to have ST segment elevation be the highest priority, followed by ECG waveform, followed by heart rate.

In an implementation, the playback interface 125 may automatically select and/or recommend to the user a medical condition based on and/or consistent with the patient data. For example, cardiac arrest is a medical condition consistent with patient data that includes CPR compression data. The playback interface 125 may display a recommended medical condition and the user may accept or reject the displayed recommendation via the medical condition selection control 586 and/or another input device.

In some implementations, the playback interface 125 may adjust the information displayed in the preview pop-up window 860 if the playback pointer 518 and/or the on-screen cursor 850 are co-located with a visual event indicator 620. This situation may indicate that the patient data in the preview pop-up window 860 corresponds to the time of the visual event indicator. For instance, the visual event indicator 620 may be a lightning bolt (e.g., indicator 624) that represents defibrillation shock event, in which case the priority and information display formatting may be adjusted to present the information most relevant and in an optimal fashion relative to the specific defibrillation event; for instance, the information displayed may be 6 seconds of ECG prior to the defibrillation shock, 9 seconds of ECG after the shock, the results of the defibrillation analysis pre-shock (e.g. either "Shock" or "No-Shock Advised"), 6 seconds of additional ECG along with ECG heart rate and pulse oximetry heart rate after some period of delay post-shock (e.g. 5 seconds, 10 seconds, 30 seconds) in order to assess whether return of spontaneous circulation was achieved. If the visual event indicator 620 is the Rx symbol (e.g., indicator 625) representing a drug administration event, for instance delivery of an asthma inhaler, the highest priority data element may be breath tidal volume, followed by other respiratory diagnostic information like capnographic information or spirometric data.

In some implementations, narrow regions around the visual event indicators have a so-called "magnetic" feature. The magnetic feature causes the on-screen cursor 850 to be attracted to the timeline location of the particular visual event indicator 620 to which the on-screen cursor 850 is adjacent within less than a predetermined distance. The predetermined distance may be measured in terms of time (e.g. less than 30 seconds, less than 1 minute, etc.) or screen distance (e.g. less than 0.05 inch, less than 0.1 inch, less than 0.25 inch). When the on-screen cursor 850 is less than the predetermined distance from the visual event indicator 620, what is displayed on the preview pop-up window 860 is the information from the time at the visual event indicator 620. In some implementations, the magnetic feature may also include causing the on-screen cursor 850 to jump spatially so that it is vertically aligned with the visual event indicator 620. In some implementations, when the magnetic feature occurs and the information from the time of the visual event indicator 620 is displayed in the preview pop-up indicator, it may further cause the preview pop-up window to increase in size so that more data may be displayed easily and cogently.

For example, the patient data may include a physiologic waveform 870. In various implementations, the preview pop-up window 860 may provide the patient data in a text and/or numeric format 873 and/or in a non-numeric graphical format 876 (e.g., a bar graph, a Tillable shape, an icon, an arrow, etc.). The patient data display in the preview pop-up window 860 may correspond to the time 855 (e.g., 10:40:49 am) associated with the position of the on-screen cursor 850. In an implementation, the preview pop-up window 860 may include a window time indicator 865 that indicates the position of the cursor 850 along the interactive timeline 190.

Referring again to FIG. 5, the interactive timeline 190 may include a playback pointer 518. During playback of patient data in the data display window 510, the playback pointer 518 may automatically move along the interactive timeline 190 synchronously with the playback of the patient data in terms of time. Thus, the playback pointer 518 may dynamically indicate the time associated with the patient data shown in the data display window 510 during playback. When the playback pointer 518 reaches the current time (e.g., as indicated by the temporal label 516a that displays "LIVE"), the patient data shown in the data display window 510 corresponds to real-time data. In an implementation, the data display window 510 may include a playback position indicator 519 that indicates a numeric representation of the time on the interactive timeline 190 associated with the playback pointer 518.

The playback interface 125 may include a media navigation bar 191. The media navigation bar 191 may include user interactive data display controls for the data displayed in the data display window 510. As used at least with regard to the media navigation bar 191, "control" refers to either or both of a physical button or a virtual/screen selection interface option. For example, the media navigation bar 191 may include a rewind control 532, a play control 533, a stop control 534, a pause control 535, and a fast forward control 536. The bar 191 may further include a skip back control 531, and skip forward control 537. These user interactive data display controls may enable the user to control the playback of the patient data at the playback interface 125. These controls may determine a time during the medical event at which to begin and/or end data playback, a speed at which to provide the playback, and/or initiate a start and/or stop of the patient data playback. The skip back control 531 and the skip forward control 537 may enable the playback interface 125 to select a time corresponding the beginning or the end of a data record or a section of a data record. These controls may enable the user to review data according to a user-selected sequence and skip between medical events, chapters, and/or visual event indicators 620.

In an implementation, the playback interface 125 may include one or more of a jump-back control 539a and a jump-forward control 539b. For example, the media navigation bar 191 may include these controls. The jump-back control 539a and the jump-forward control 539b may change the time of the displayed patient data by a preconfigured interval. The preconfigured interval may be, for example, 5 seconds, 10 seconds, 15 seconds, 30 seconds, 60 seconds, 120 seconds, 180 seconds, or another suitable time period. In an implementation, the playback interface 125 may enable the jump-back control 539a and the jump-forward control 539b once the playback of the patient data is underway.

The time selection controls (e.g., the skip back control 531, the skip forward control 537, the jump-back controls 539a and 539b, and/or the one or more data window time selectors 622a and 622b) may permit the user of the playback interface 125 to selectively review data at times at which significant events of interest occurred. In contrast, without these selection features, the reviewer may have to review a sequence of captured data in chronological order and some or most of the sequence may not include data of interest to the reviewer.

In an implementation, the playback interface 125 may include a playback speed selection bar 538. The playback interface 125 may present the patient data at a default playback speed. By clicking on or otherwise selecting one of the 2×, 4×, 8×, or 16× portions of the playback speed selection bar 538, the user may adjust the presentation speed for the patient data to a speed other than the default speed. In an implementation, the playback speed may be a multiplier applied to the default playback speed. The playback speed may be, for example, but not limited to, 2×, 4×, 8×, or 16× this default playback speed. The user may adjust the playback speed to change the duration of the patient data playback. For example, at the default speed, the playback duration for the patient data of interest may be 12 minutes. The user may select a 4× playback speed to reduce the playback duration to three minutes. In an implementation, the playback speed may be continuously configurable between a range of speeds (e.g., 0.25×-4×) rather than a discrete speed setting (e.g., 2×, 4×). For example, the low end of the speed range might be as low as 0.250×, 0.5×, or 2×. The high end of the speed range might be at least 2×, 4×, 8×, 16×, 32×. In an implementation, the playback speed selection bar 538 may be configured to visually indicate a currently active playback speed selection.

In an implementation, the selected playback speed or the default playback speed may be the same speed at which at which the operational interface 135 displays the patient data in real-time. For example, the operational interface 135 may display waveform and/or time trend data at a sweep speed. The sweep speed may be a user configurable speed and the operational interface 135 may display the waveform and/or time trend data at a default speed or at a user selected speed. In an implementation, the playback interface 125 may receive a current sweep speed setting from the operational interface 135 in order to match or apply a multiplier to the current sweep speed. As examples, the sweep speed may be a speed in a range of approximately 1 mm/sec-50 mm/sec. For example, the sweep speed may be approximately 3 mm/sec, 6 mm/sec, 12.5 mm/sec, 25 mm/sec, or 50 mm/sec. The default sweep speed and/or speed options provided for a user configuration may depend on the particular data in the time trend and/or waveform. For example, ECG data may correspond to different default and/or options for the sweep speed than $CO_2$ or other ventilation and/or respiration parameter data.

The playback of data may proceed at the selected playback speed over the selected time period. Any physiological measurements collected and saved during this time may appear on the playback interface 125 at the times during the selected time period corresponding to the time at which the medical device collected and saved these measurements. In an implementation, the playback interface 125 may display a value for the measurement and then change the value at a time when a new measurement was collected and saved by the medical device. For example, the selected time interval for playback may be one minute. During this minute, the device 110, 210, 310, or 410 may have collected physiological measurements once per second (e.g., heart rate, invasive blood pressure, oxygen saturation, etc.). The playback may proceed according to the default or user selected playback speed and for each playback time interval corresponding to one second, the playback interface 125 may display the physiological measurement for that interval and then change the displayed measurement at the next playback time interval corresponding to one second. As another example, the medical device may collect some physiological measurements on demand. For example, a user may request a non-invasive blood pressure measurement at regular or irregular intervals. Each measurement may include a time stamp and the playback interface 125 may display the measurement based on the time stamp. In an implementation, the device 110, 210, 310, or 410 may collect numeric values for other available parameters every time the device collects blood pressure and/or another parameter measurement on demand. As a further example, performance data timing may correspond to performance time intervals. For instance, the device 110, 210, 310, or 410 may collect chest compression rate and depth data for each chest compression. Thus, the time intervals of the collection may depend on the compression rate. Each item of performance data may include a time stamp and the playback interface 125 may display the measurement based on the time stamp. In an implementation, the device 110, 210, 310, or 410 may capture numeric values of all available parameters at a regular time interval (e.g., every 5 seconds, every 10 seconds, every 15 seconds, every 30 seconds, every 60 seconds, etc.). The playback interface 125 may provide these numeric values for every capture time within the playback interval to provide a time trend for these values.

In an implementation, the playback interface 125 may automatically adjust the playback speed based on whether the playback data is historical or real-time data. For example, during playback of historical data, the user selected playback speed (e.g., as selected via the playback speed selection bar 538) may determine an actual playback speed implemented by the playback interface 125. In an implementation, the playback pointer 518 may move along the interactive timeline 190 as the data playback proceeds to indicate the time stamp associated with the displayed data. When the playback pointer 518 reaches the current time indicating that the displayed patient data corresponds to real-time data rather than historical data, the playback interface 125 may automatically override the user-selected speed and change the playback speed to match the speed at which the operational interface 135 displays the data in real-time (e.g., the default or user selected sweep speed).

In an implementation, the playback interface 125 may include a rotary navigation control 560. For example, the rotary navigation control 560 may provide media navigation capabilities similar to those provided by the media navigation bar 191. Further, the rotary navigation control 560 may provide playback loop selection capabilities. The rotary navigation control 560 may be, for example, a jog dial, a jog wheel, a shuttle dial, a shuttle wheel, etc. The rotary navigation control 560 may enable the user to scan through the playback images at the playback interface 125 at various speeds (e.g., a fast shuttle speed or a slow jog speed). In an implementation, the rotary navigation control 560 may be configured to rotate while it is pressed in to a detented stop. Each rotary detent may indicate a request to the playback interface 125 to skip to the next event in the playback data, such as a defibrillation or drug delivery. The rotary navigation control 560 may be in the form of a physical knob that rotates and contains a rotary encoder, or may take the form of a touchscreen emulation of a rotary knob that the user moves with circular finger motion.

In an implementation, the playback interface 125 may provide a volume selection bar 570. The volume selection bar 570 may capture input from the user and, in response to the captured input, the playback interface 125 may adjust an audio playback volume. For example, the user of the playback interface 125 may click on, tap, press, or otherwise provide input to the volume selection bar 570. In an implementation, the playback interface 125 may provide audio data from the medical event simultaneously with or instead of the visual data.

Figure 9:
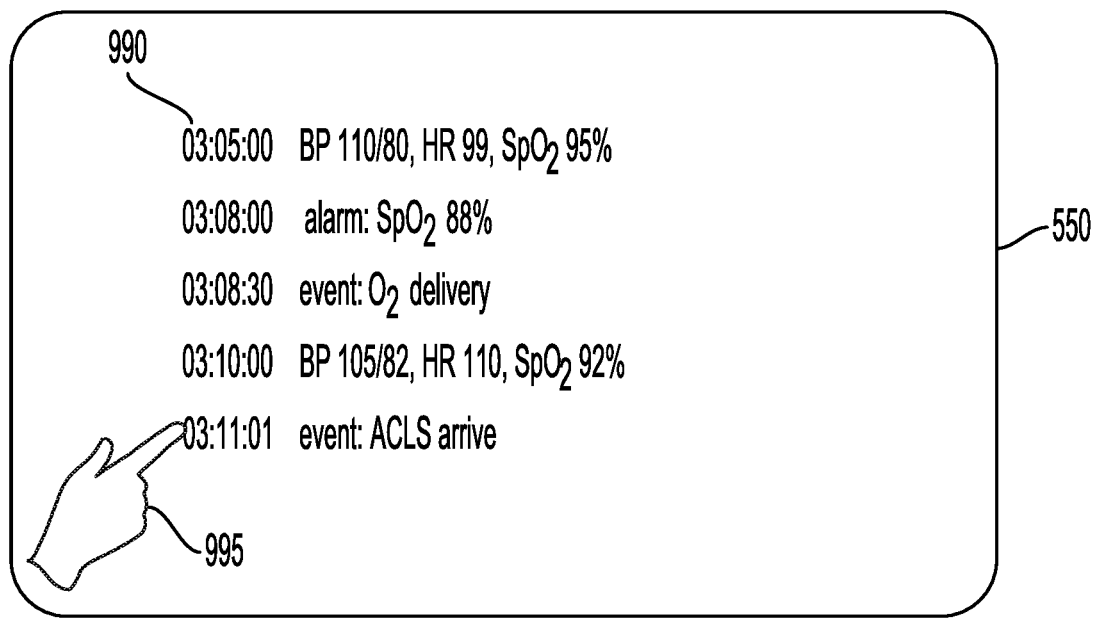
FIG. 9 shows an example of an event search function for the playback interface.

Referring to FIGS. 5 and 9, an example of an event search function for the playback interface is shown. In an implementation, playback interface 125 may provide an event search function 583. The user may activate the event search function 583, for example, via the one or more input device(s) 144, 244, 344 (e.g., a soft-key, a tap on a touchscreen icon, a selection of an icon via a cursor, etc.).

In an implementation, activation of the event search function 583 may open the interactive menu 550. The interactive menu 550 may include a text list 990 of events and/or interventions and may include one or more code markers. The list 990 may be a user-selectable list. In this example, the list 990 includes time stamped data for blood pressure (BP), heart rate (HR), oxygen saturation ($SpO_2$), delivery of oxygen ($O_2$), and arrival of advanced cardiac life support (ACLS) equipment and/or personnel. The user may select an event from the list 990 to initiate playback of event data. For example, the user of the playback interface 125 may select an event via a touch gesture or a mouse or other input device (e.g., input device(s) 144, 244, or 344). Via the user input, the user may adjust a position of a selection cursor 995 to select the event. In response, the playback interface 125 may provide playback of data collected by the medical device 110 at the time of the selected event indicator (e.g., the event "ACLS arrive" at 03:11:01 is shown as selected in FIG. 9 based on the position of the selection cursor 995). In an implementation, the text list 990 may be a sorted list according to chronological order.

The event search function 583 may be a search/sort function and may sort the visual event indicators 620 or code markers by types of events and interventions, for instance, defibrillation shock, drug administration, intubation, fluid delivery, chest compression protocol, or ventilation protocol. The events may also be sorted into diagnostic events and therapy events. For example, therapy events may include defibrillation, pacing, drug delivery, etc. Diagnostic events may include detection of ventricular fibrillation, COPD, asthma, etc.

In an implementation, activation of the event search function 583 may enable a user selection of one or more particular types of the visual event indicator 620 and/or code markers (e.g., shock events, drug events, etc.). For example, in response to the selection of an event, the event search function 583 may highlight events on the interactive menu that correspond to the selected type of code marker. In an implementation, the event search function 583 may highlight the visual event indicators 620 on the interactive timeline 190 that correspond to the selected type of code marker. The user may select one or more of the visual event indicators 620 on the interactive timeline 190 to receive more information about the event indicated by the visual event indicator.

Referring again to FIG. 5, in an implementation, the playback interface 125 may provide a tool function key 580. The user may activate the tool function key 580, for example, via a touchscreen icon, a soft-key, and/or other user input device. The tool function key 580 may enable a selection of one or more particular types of tools that may include playback time intervals and/or playback speeds. In an implementation, the tool function key 580 may provide selectable options at the interactive menu 550.

In an implementation, the playback interface 125 may enable the user to play back data based on a specific medical condition of the patient. The user may select the medical condition via one or more of the event indicators 620 and/or a medical condition selection control 586. For example, the user may select the event indicator 620 that corresponds to a medical condition of interest to the user with regard to data review. Alternatively or additionally, the user may activate the medical condition selection control 586 via the one or more input device(s) 144, 244, 344 (e.g., a soft-key, a tap on a touchscreen icon, a selection of an icon via a cursor, etc.). The medical condition selection control 586 may enable the user to select one or more medical conditions, for example, via the interactive menu 550. The interactive menu 550 may display a list of one or more medical conditions. The one or more medical conditions may be conditions of the patient whose data is under review via the playback interface 125.

Based on the selected medical condition, the playback interface 125 may predetermine various configuration and/or usage settings for data playback and/or display at the playback interface 125. For example, in an implementation, the playback interface 125 may automatically select one or more playback intervals 623 based on the medical condition selected by the user. Additionally or alternatively, the playback interface 125 may select the playback speed, and/or the number of loop repetitions based on the selected medical condition.

For example, the user may select a medical condition of "chest pain" at the interactive menu 550. Additionally or alternatively, the user may select the drug delivery event indicator 625 corresponding to administration of nitroglycerine. The user may select this event based on the knowledge that nitroglycerine may be administered in response to chest pain. In response to either or both of these selections, the playback interface 125 may provide ECG data for a time period spanning the drug administration. Further, the playback interface 125 may automatically select a playback start time at 10 seconds prior to the nitroglycerine delivery event and then set playback for data over a time period of 1, 5, 10, 15 minutes, etc. The time period may be preconfigured as a clinically relevant time period based on the selected one or more medical conditions. As another example, if the selected medical condition is difficulty breathing, the playback interface may select a start point that coincides with an event indicator for delivery of bronchodilator (e.g., event indicator 626).

Figure 10A:
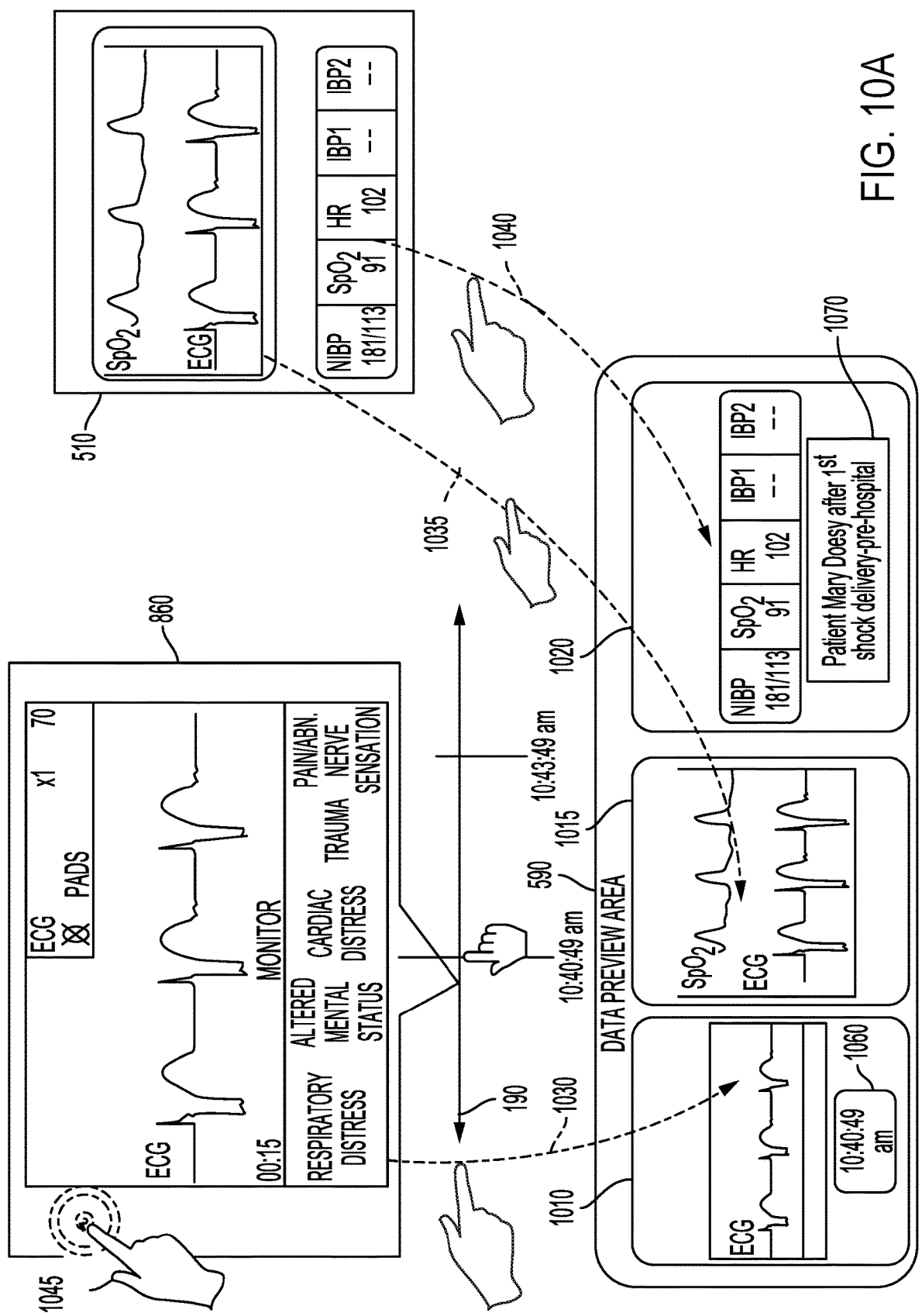
FIG. 10A shows an example of a data preview area for the playback interface.

Referring to FIG. 10A, with further reference to FIG. 5, an example of a data preview area for the playback interface is shown. In an implementation, the playback interface 125 may provide the data preview area 590. The data preview area 590 may include one or more data preview windows, e.g., data preview windows 1010, 1015, and 1020. In an implementation, the user of the playback interface 125 may drag and drop displayed information from the data display window 510 and/or from the preview pop-up window 860 to the data preview area 590. For example, the user may implement one of the drag and drop touchscreen gestures represented schematically in FIG. 10A as the arrows 1030, 1035, and 1040. In an implementation, the user may implement a tap and/or a push (e.g., the push gesture 1045) to exert pressure on a particular data image, thereby causing the playback interface 125 to add the particular data image to the data preview area 590. In a further implementation, the user may add data to the data preview area 590 via a pointing device such as a mouse and/or a cursor. For example, the user may click/double click on a selected data image and either drag the selected data image to the data preview area 590 or employ a second click to move the selected data image to the data preview area 590.

In an implementation, the data preview windows 1010, 1015, and 1020 may provide data in various formats. For example, one or more of the data preview windows may provide the data in a time trend format, waveform format, text format, numeric format, and/or non-numeric graphical format.

In an implementation, one or more of the data preview windows 1010, 1015, and 1020 may include a time display 1060. The time display 1060 may be the time on the interactive timeline 190 that is associated with the data image in the respective data preview window 1010, 1015, or 1020. In an implementation, the playback interface 125 may automatically display the data images within the data preview area 590 in chronological order. For example, as a data image is added to a data preview window 1010, 1015, and/or 1020, the playback interface 125 may rearrange the data preview windows 1010, 1015, and 1020 such that the windows display the data images in chronological order from right to left or from left to right within the data preview area 590.

In an implementation, the data preview area 590 may enable a data overlay mode. For example, a user may drag a first data preview window onto a second data preview window and over lay corresponding data from different time periods. This may help the user to identify changes in the data over time. For example, the overlay may include an ECG prior to an intervention and an ECG scan subsequent to an intervention. In an implementation, the playback interface may highlight or otherwise designate differences between the data sets in overlay.

In an implementation, the playback interface 125 may prompt the user to enter an annotation 1070 specific to the data image when it has been dragged to the data preview area 590. For example, the annotation may include caregiver notes, observations, instructions, etc. The playback interface 125 may capture the annotation 1070 as a text input, for instance via a keyboard and/or via an audio input, for instance, via a microphone. The playback interface 125 may associate the audio recording with the particular data represented by the data image. In addition, the playback interface 125 may implement voice recognition software to convert the audio recording into text.

In an implementation, the user may select one of the data preview windows 1010, 1015, or 1020 for data playback. The data display window 510 may playback the data from the selected data preview window 1010, 1015, or 1020. For example, the user may initiate playback by pressing on the selected data preview window, clicking a mouse controlling a cursor on the selected data preview window, or otherwise providing user input, via the touchscreen or other user input device, indicative of the selected data preview window. The processor 120 may control the playback interface 125 to begin playback of the data in the selected data preview window at the time indicated by the time display 1060 or alternatively at a time that is a preconfigured interval (e.g., 1 second, 5 seconds, 10 seconds, 15 seconds, 30 seconds, 60 seconds, 120 seconds, 180 seconds, etc.) before the time indicated by the time display 1060.

Figure 10B:
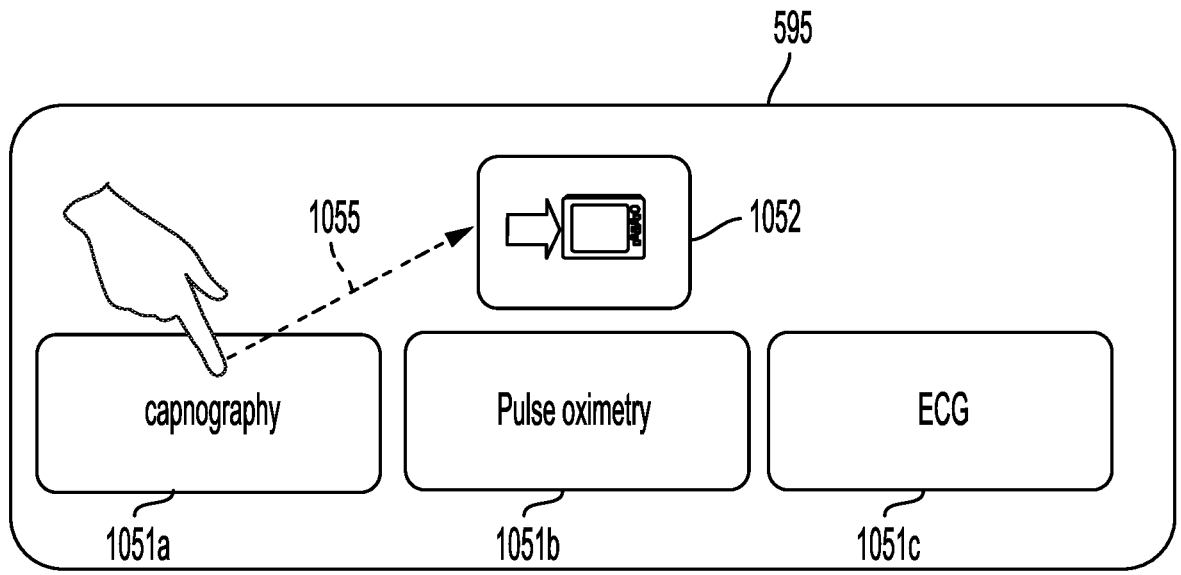
FIG. 10B shows an example of a data selection area for user selection of data to display on a communicatively coupled device.
Figure 10C:
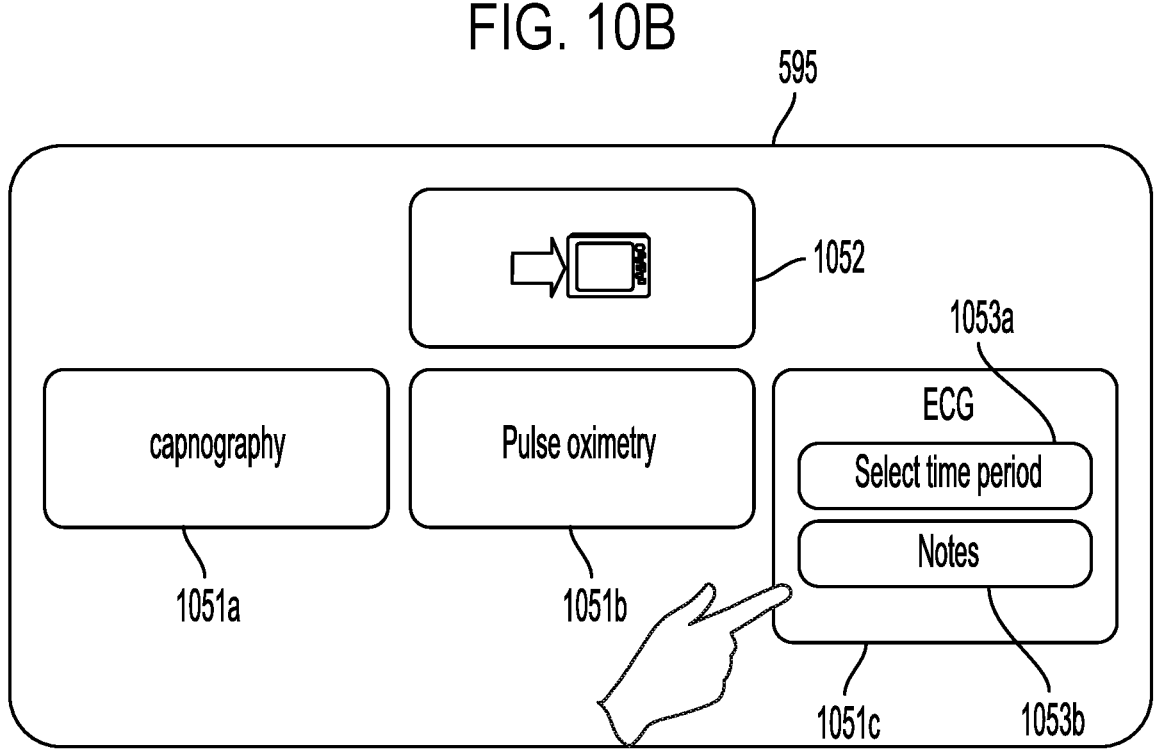
FIG. 10C shows an example of a data selection area for user selection of data to display on a communicatively coupled device.

Referring to FIGS. 10B and 10C, with further reference to FIG. 5, examples of a data selection area for user selection of data to display on a communicatively coupled device are shown. In an implementation, the playback interface 125 may include the data selection area 595. The data selection area 595 may include one or more data type icons (e.g., the icons 1051a, 1051b, and 1051c) where data type icon corresponds to a particular data type (e.g., capnography, pulse oximetry, ECG, etc.). The icons may be textual, graphic, or a combination thereof. The data selection area 595 may further include one or more target device icons 1052. Each of the target device icon(s) 1052 may represent a communicatively coupled device. For example, if the data selection area 595 is at the playback interface 125b of the second medical device 210, the communicatively coupled device may be the first medical device 110 and/or the computing device 310. In this scenario, for example, the second medical device 210 may capture the user selection of data to display at the first medical device 110. The second medical device 210 may provide this selection as an instruction to the first medical device 110 via the communicative coupling 298. The first medical device 110 may receive this instruction and control its display screen 115 to display the data selected by the user at the second medical device 210.

Referring to FIG. 10B, in an implementation, the user of the playback interface 125 may select a data type via a touchscreen gesture. For example, the user may perform a drag and drop gesture 1055 to drag the selected data type (e.g., capnography) to the target device icon 1052. In response to this gesture, the processor controlling the playback interface 125 may send an instruction indicative of the selected data type to the communicatively coupled device.

Referring to FIG. 10C, in an implementation, the user of the playback interface 125 may tap on a data type icon (e.g., the ECG icon 1051c) to open one or more data attribute windows (e.g., the windows 1053a and 1053b). For example, the data attribute windows may enable the user to select a time period for the data display instruction (e.g., using the time period selection window 1053a) and/or include notes for the user of the communicatively coupled device (e.g., using the notes window 1053b). Alternatively or additionally, the user may provide data display instructions for the communicatively coupled device via the interactive menu 550 shown in FIG. 5.

Referring to FIG. 11, examples of components of various devices discussed with regard to FIGS. 1A-10C are shown schematically. These devices may include the medical device 110, one or more additional medical device(s) 210, one or more computing device(s) 310, and one or more server(s) 1110. In an implementation, at least one of the medical devices 110 and 210 may be a therapeutic medical device configured to deliver medical therapy to the patient and may not be limited to patient monitoring and/or diagnostic care. The computing device 310 may be adapted to function as a medical device. In an implementation, the computing device 310 may not be a therapeutic medical device configured to deliver medical therapy to the patient. In such an implementation, the computing device 310 may be limited to patient monitoring and/or diagnostic care.

One or more of the devices 110, 210, 310, and 1110 may be communicatively coupled via communicative couplings 298, 396, 397, 1170, 1180, and/or 1190. These communicative couplings may be each be a wired and/or a wireless communications link. The wired communications links may include a wired electrical coupling, an optical coupling via an optical cable, etc. The wireless communications link may include coupling via a radio frequency or other transmission media and/or via a network such as a local area network, an ad hoc network, a mesh network, a cellular and/or other communications network, a computer network, etc. The communications links as described herein may utilize protocols such as, for example, 802.11, ZigBee®, Bluetooth®, etc. The communications links may include near field communications which may be implemented via a communications RFID tag. The communications links may include one or more networks (e.g., the networks 299 and 399) such as a local area network, a cellular network, a satellite network, and/or a computer network (e.g., an Internet Protocol (IP) network). In various implementations, the communicative couplings described herein may provide secure and/or authenticated communications channels. In an implementation, the devices described herein may encrypt and/or decrypt the data transmitted and/or received via the communicative couplings.

In FIG. 11, the components 120, 121, 130, 144, 145, and 155 are communicatively coupled (directly and/or indirectly) to each other for bi-directional communication. Similarly, the components 220, 221, 230, 244, 245, and 255 are communicatively coupled (directly and/or indirectly) to each other for bi-directional communication and the components 320, 321, 330, 344, and 345 are communicatively coupled (directly and/or indirectly) to each other for bi-directional communication.

Although shown as separate entities in FIG. 11, the components 120, 121, 145, and/or 155 may be combined into one or more discrete components and components 145 and/or 155 may be part of the processor 120. The processor 120 and the memory 121 may include and/or be coupled to associated circuitry in order to perform the functions described herein. Although shown as separate entities in FIG. 11, the components 220, 221, 245, and/or 255 may be combined into one or more discrete components and components 245 and/or 255 may be part of the processor 220. The processor 220 and the memory 221 may include and/or be coupled to associated circuitry in order to perform the functions described herein. Although shown as separate entities in FIG. 11, the components 320, 321, and 345 may be combined into one or more discrete components and component 345 may be part of the processor 320. The processor 320 and the memory 321 may include and/or be coupled to associated circuitry in order to perform the functions described herein.

The medical devices 110 and/or 210 may include the therapy delivery control module 155 or 255. For example, the therapy delivery control module 155 and/or 255 may be an electrotherapy delivery circuit that includes one or more capacitors configured to store electrical energy for a pacing pulse or a defibrillating pulse. The electrotherapy delivery circuit may further include resistors, additional capacitors, relays and/or switches, electrical bridges such as an H-bridge (e.g., including a plurality of insulated gate bipolar transistors or IGBTs), voltage measuring components, and/or current measuring components. As another example, the therapy delivery control module 155 and/or 255 may be a compression device electro-mechanical controller configured to control a mechanical compression device. As a further example, the therapy delivery control module 155 and/or 255 may be an electro-mechanical controller configured to control drug delivery, temperature management, ventilation, and/or other type of therapy delivery.

The medical device 110 (e.g., a first medical device) may incorporate and/or be configured to couple to one or more patient interface device(s) 160. The patient interface device(s) 160 may include one or more therapy delivery component(s) 161a and one or more sensor(s) 161b. Similarly, the medical device 210 (e.g., a second medical device) may incorporated and/or be configured to couple to one or more patient interface device(s) 260. The patient interface device(s) 260 may include one or more therapy delivery components 261a and one or more sensors 261b. The computing device 310 may be adapted for medical use and may incorporate and/or be configured to couple to one or more patient interface device(s) 360. The patient interface device(s) 360 may include one or more sensors 361. The therapy delivery component(s) 261a may be substantially as described herein with regard to the therapy delivery component(s) 161a. Similarly, the sensor(s) 261b and 361 may be substantially as described herein with regard to the sensor(s) 161b.

The medical device 210 may receive patient data in a manner substantially similar to that described above for the medical device 110. The device 210 may receive the patient data based on signals received from the therapy delivery component(s) 261a and the sensor(s) 261b. The sensor(s) 261b may be substantially as described herein with regard to the sensor(s) 161b.

The sensor(s) 161b, 261b, and 361 may include sensing electrodes (e.g., the sensing electrodes 162), ventilation and/or respiration sensors (e.g., the ventilation and/or respiration sensors 164), temperature sensors (e.g., the temperature sensor 167), chest compression sensors (e.g., the chest compression sensor 168), etc. For example, the sensing electrodes may include cardiac sensing electrodes. The cardiac sensing electrodes may be conductive and/or capacitive electrodes configured to measure changes in a patient's electrophysiology to measure the patient's ECG information. The sensing electrodes may further measure the transsthoracic impedance and/or a heart rate of the patient. The ventilation and/or respiration sensors may include spirometry sensors, flow sensors, pressure sensors, oxygen and/or carbon dioxide sensors such as, for example, one or more of pulse oximetry sensors, oxygenation sensors (e.g., muscle oxygenation/pH), O2 gas sensors and capnography sensors, impedance sensors, and combinations thereof. The temperature sensors may include an infrared thermometer, a contact thermometer, a remote thermometer, a liquid crystal thermometer, a thermocouple, a thermistor, etc. and may measure patient temperature internally and/or externally. The chest compression sensor may include one or more motion sensors including, for example, one or more accelerometers, one or more force sensors, one or more magnetic sensors, one or more velocity sensors, one or more displacement sensors, etc. The chest compression sensor may provide one or more signals indicative of the chest motion to the medical device 110 and/or 210 via a wired and/or wireless connection. The chest compression sensor may be, for example, but not limited to, a compression puck, a smart-phone, a hand-held device, a wearable device, etc. The chest compression sensor may be configured to detect chest motion imparted by a rescuer and/or an automated chest compression device (e.g., a belt system, a piston system, etc.). The chest compression sensor may provide signals indicative of chest compression data including displacement data, velocity data, release velocity data, acceleration data, force data, compression rate data, dwell time data, hold time data, blood flow data, blood pressure data, etc. In an implementation, the defibrillation and/or pacing electrodes may include or be configured to couple to the chest compression sensor.

In various implementations, the sensor(s) 161b, 261b and/or 361 may include one or more sensor devices configured to provide sensor data that includes, for example, but not limited to electrocardiogram (ECG), blood pressure, heart rate, respiration rate, heart sounds, lung sounds, respiration sounds, end tidal $CO_2$, saturation of muscle oxygen ($SMO_2$), oxygen saturation (e.g., $SpO_2$ and/or $PaO_2$), cerebral blood flow, point of care laboratory measurements (e.g., lactate, glucose, etc.), temperature, electroencephalogram (EEG) signals, brain oxygen level, tissue pH, tissue fluid levels, images and/or videos via ultrasound, laryngoscopy, and/or other medical imaging techniques, near-infrared reflectance spectroscopy, pneumography, cardiography, and/or patient movement. Images and/or videos may be two-dimensional or three-dimensional.

The one or more therapy delivery components 161a and 261a may include electrotherapy electrodes (e.g., the electrotherapy electrodes 166a), ventilation device(s) (e.g., the ventilation devices 166b), intravenous device(s) (e.g., the intravenous devices 166c), compression device(s) (e.g., the compression devices 166d), etc. For example, the electrotherapy electrodes may include defibrillation electrodes, pacing electrodes, and combinations thereof. The ventilation devices may include a tube, a mask, an abdominal and/or chest compressor (e.g., a belt, a cuirass, etc.), etc. and combinations thereof. The intravenous devices may include drug delivery devices, fluid delivery devices, and combinations thereof. The compression devices may include mechanical compression devices such as abdominal compressors, chest compressors, belts, pistons, and combinations thereof. In various implementation, the therapy delivery component(s) 161a and/or 261a may be configured to provide sensor data and/or be coupled to and/or incorporate sensors. For example, the electrotherapy electrodes may provide sensor data such as transthoracic impedance, ECG, heart rate, etc. Further the electrotherapy electrodes may include and or be coupled to a chest compression sensor. As another example, the ventilation devices may be coupled to and/or incorporate flow sensors, gas species sensors (e.g., oxygen sensor, carbon dioxide sensor, etc.), etc. As a further example, the intravenous devices may be coupled to and/or incorporate temperature sensors, flow sensors, blood pressure sensors, etc. As yet another example, the compression devices may be coupled to and/or incorporate chest compression sensors, patient position sensors, etc. The therapy delivery control modules 155 and 255 may be configured to couple to and control the therapy delivery component(s) 161a and 261a, respectively.

The one or more sensor(s) 161b, 261b, and 361 and/or the therapy delivery component(s) 161a and 261a may provide sensor data. The patient data provided at the operational interface and/or playback interface may include the sensor data. For example, the medical device 110 (e.g., the first medical device) may process signals received from the sensor(s) 161b and/or the therapy delivery component(s) 161a to determine the sensor data. Similarly, the medical device 210 may process signals received from the sensor(s) 261b and/or the therapy delivery component(s) 261a to determine the sensor data and the computing device 310 may process signals received from the sensor(s) 361 to determine the sensor data.

Referring to FIG. 12, examples of components of the modular therapeutic medical device/patient monitor are shown. The modular therapeutic medical device/patient monitor may include a therapeutic medical device and patient monitor configured to communicatively couple to one another. For example the therapeutic medical device may be a defibrillator and the modular therapeutic medical device/patient monitor may include a defibrillator and patient monitor configured to communicatively couple to one another Although shown as separate entities in FIG. 12, the components 420a, 421a, 445a, and/or 455 may be combined into one or more discrete components and components 445a and/or 455 may be part of the processor 420a. Similarly, although shown as separate entities in FIG. 12, the components 420b, 421b, and/or 445b may be combined into one or more discrete components and component 445b may be part of the processor 420b. The processor 420a and the memory 421a may include and/or be coupled to associated circuitry in order to perform the functions described herein. Similarly, the processor 420b and the memory 421b may include and/or be coupled to associated circuitry in order to perform the functions described herein. The components 420a, 421a, 430a, 444a, 445a, and 455 are communicatively coupled (directly and/or indirectly) to each other for bi-directional communication. Similarly, the components 420b, 421b, 430b, 444b, and 445b are communicatively coupled (directly and/or indirectly) to each other for bi-directional communication The therapy delivery control module 455 may be an electrotherapy delivery circuit substantially as described with regard to the therapy delivery control modules 155 and 255. As another example, the therapy delivery control module 455 may be a compression device electro-mechanical controller configured to control a mechanical compression device. As a further example, the therapy delivery control module 455 may be an electro-mechanical controller configured to control drug delivery, temperature management, ventilation, and/or other type of therapy delivery.

Referring to FIGS. 11 and 12, the medical device 110 may include a processor 120, a memory 121, one or more output devices 130, one or more user input devices 144, and a communications interface 145. The medical device 210 may include a processor 220, a memory 221, one or more output devices 230, one or more user input devices 244, and a communications interface 245. The computing device 310 may include a processor 320, a memory 321, one or more output devices 330, one or more user input devices 344, and a communications interface 345. The therapeutic medical device 410a may include a processor 420a, a memory 421a, one or more output devices 430a, one or more input devices 444a, and a communications interface 445a. The patient monitor 410b may include a processor 420b, a memory 421b, one or more output devices 430b, one or more input devices 444b, and a communications interface 445b.

The processors 120, 220, 320, 420a, and 420b are physical processors (i.e., an integrated circuit configured to execute operations on the devices 110, 210, 310, 410a, and 410b, respectively, as specified by software and/or firmware stored in a computer storage medium). The processors 120, 220, 320, 420a, and 420b are operably coupled, respectively, to the memory 121, the memory 221, the memory 321, the memory 421a, and the memory 421b. The processors 120, 220, 320, 420a, and 420b may be intelligent hardware devices (for example, but not limited to, a central processing unit (CPU), a graphics processing unit (GPU), one or more microprocessors, a controller or microcontroller, an application specific integrated circuit (ASIC), a digital signal processor (DSP), etc.) designed to perform the functions described herein and operable to carry out instructions on the devices 110, 210, 310, 410a, and 410b, respectively. Each of the processors 120, 220, 320, 420a, and 420b may be one or more processors and may be implemented as a combination of hardware devices (e.g., a combination of DSP and a microprocessor, a plurality of microprocessors, one or more microprocessors in conjunction with a DSP core, or another such configuration). Each of the processors 120, 220, 320, 420a, and 420b may include multiple separate physical entities that may be distributed in the devices 110, 210, 310, 410a, and 410b respectively. Each of the processors 120, 220, 320, 420a, and 420b is configured to execute processor-readable, processor-executable software code containing one or more instructions or code for controlling the processors 120, 220, 320, 420a, and 420b to perform the functions as described herein. The processors 120, 220, 320, 420a, and/or 420b may utilize various architectures including but not limited to a complex instruction set computer (CISC) processor, a reduced instruction set computer (RISC) processor, or a minimal instruction set computer (MISC). In various implementations, the processors 120, 220, 320, 420a and/or 420b may be a single-threaded or a multi-threaded processor. The processors 120, 220, 320, 420a, and/or 420b may be, for example, an Intel® Itanium® or Itanium 2® processor(s), AMD® Opteron®, Athlon MP® processor(s), a Motorola® line of processor, or an ARM, Intel Pentium Mobile, Intel Core i5 Mobile, AMD A6 Series, AMD Phenom II Quad Core Mobile, or like devices.

The memories 121, 221, 321, 421a, and 421b refer generally to a computer storage medium, including but not limited to RAM, ROM, FLASH, disc drives, fuse devices, and portable storage media, such as Universal Serial Bus (USB) flash drives, etc. Each of the memories 121, 221, 321, 421a, and 421b may include, for example, random access memory (RAM), or another dynamic storage device(s) and may include read only memory (ROM) or another static storage device(s) such as programmable read only memory (PROM) chips for storing static information such as instructions for a coupled processor (e.g., one of the processors 120, 220, 320, 420a, and 420b). The memories 121, 221, 321, 421a, and 421b may include USB flash drives that may store operating systems and other applications. The USB flash drives may include input/output components, such as a wireless transmitter and/or USB connector that can be inserted into a USB port of another computing device. The memories 121, 221, 321, 421a, and/or 421b may be long term, short term, or other memory associated with the respective device 110, 210, 310, 410a, and 410b and are not to be limited to a particular type of memory or number of memories, or type of media upon which memory is stored. The memories 121, 221, 321, 421a, and/or 421b include a non-transitory processor-readable storage medium (or media) that stores the processor-readable, processor-executable software code. The memories 121, 221, 321, 421a, and/or 421b may store information and instructions. For example, the memories 121, 221, 321, 421a, and/or 421b may include flash memory and/or another storage media may be used, including removable or dedicated memory in a mobile or portable device. As another example, hard disks such as the Adaptec® family of SCSI drives, an optical disc, an array of disks such as RAID (e.g. the Adaptec family of RAID drives), or another mass storage devices may be used. The memories 121, 221, 321, 421a, and/or 421b may include removable storage media such as, for example, external hard-drives, floppy drives, flash drives, zip drives, compact disc-read only memory (CD-ROM), compact disc-re-writable (CD-RW), or digital video disk-read only memory (DVD-ROM).

The communications interfaces 145, 245, 345, 445a, and 445b may transmit and/or receive information to and/or from one or more devices external to and communicatively coupled to the devices 110, 210, 310, 410a, and 410b, respectively. The communications interfaces 145, 245, 345, 445a, and 445b may transmit and/or receive the information via a wired and/or wireless communicative coupling (e.g., the couplings 298, 396, 397, 398a, 398b, 498, 1170, 1180, 1190, 1292, or 1293). The information may include information stored in at least one of the memories 121, 221, 321, 421a, and 421b. The information may include, for example, but not limited to, resuscitative treatment information, physiological information, patient information, rescuer and/or caregiver information, location information, rescue and/or medical treatment center information, etc. The communications interfaces 145, 245, 345, 445a, and/or 445b may enable short range and/or long range wireless communications capabilities which may include communications via near field communications, ZigBee®, Wi-Fi, Bluetooth®, satellite(s), radio waves, a computer network (e.g., the Internet), a cellular network, etc. The communications interfaces 145, 245, 345, 445a, and/or 445b may enable communications via a network such a Local Area Network (LAN), Wide Area Network (WAN), a mesh network, an ad hoc network, or another network. The communications interfaces 145, 245, 345, 445a, and/or 445b may include, for example, an RS-232 port for use with a modem based dialup connection, a copper or fiber 10/100/1000 Ethernet port, or a Bluetooth® or WiFi interface.

In an implementation, the communications interfaces 145, 245, 345, 445a, and/or 445b may enable communication between one or more of the devices 110, 210, 310, 410a, and 410b with one or more servers 1110. For example, the one or more servers 1110 may be remote servers and may include a cloud server and/or a central facility server. In an implementation, the one or more servers 1110 may be associated with a medical provider (e.g., a hospital, a physician's office, a medical records office, an emergency services office, an emergency services vehicle, a dispatch center, etc.). In an implementation, the communications interface 445b may enable the patient monitor 410b to communicatively couple with multiple therapeutic medical device(s) 410a and/or with another patient monitor. In an implementation, the therapeutic medical device 410a may communicatively couple with the one or more servers 1110 via the patient monitor 410b. For example, the communications interface 445a may provide patient data and/or other information from the therapeutic medical device 410a to the patient monitor 410b via the communicative coupling 498. The patient monitor 410b may merge the received patient data and/or other information with patient data and/or other information collected by and/or generated at the patient monitor 410b to create an integrated record. The patient monitor 410b may provide the integrated record to the one or more servers 1110 via the communications interface 445b and the communicative coupling 1292. Alternatively or additionally, the therapeutic medical device 410a may provide patient data and/or other information to the one or more servers 1110 via the communications interface 445a and the communicative coupling 1293. One or more of the communications interfaces 145, 245, 345, 445a, and 445b in combination with one or more of the communicative couplings 298, 396, 397, 398a, 398b, 498, 1170, 1180, 1190, 1292, and 1293 may enable telemedicine communications and data sharing of real-time and/or historical patient data in support of the telemedicine communications.

The output device(s) 130 and user input device(s) 144 may be included in the medical device 110 and/or coupled to the medical device 110. Similarly, the output device(s) 230 and the user input device(s) 244 may be included in the medical device 210 and/or coupled to the medical device 210, the output device(s) 330 and the user input device(s) 344 may be included in the computing device 310 and/or coupled to the computing device 310, the output device(s) 430a and the user input device(s) 444a may be included in the therapeutic medical device 410a and/or coupled to the therapeutic medical device 410a, and the output device(s) 430b and the user input device(s) 444b may be included in the patient monitor 410b and/or coupled to the patient monitor 410b. For example, the output device(s) 130, 230, 330, 430a, and/or 430b may include one or more of a display (e.g., the displays 115, 215, 315, 415a, and 415b), a speaker, and a haptic device. The display may provide a graphical user interface (GUI). The display may be, for example, but not limited to, a liquid crystal display (LCD) and/or a light emitting diode (LED) display. In an implementation, the output device(s) 130, 230, 330, 430a, and/or 430b may be input/output device(s) capable of capturing user input. For example, the display may be a touchscreen. The touchscreen may be, for example, a pressure sensitive touchscreen or a capacitive touchscreen. The touchscreen may capture user input provided via touchscreen gestures and/or provided via exertions of pressure on a particular area of the screen. Examples of touchscreen gestures provided herein with regard to user input may include pushing on the touchscreen to exert pressure that exceeds a particular threshold to indicate an input to a pressure sensitive touchscreen by the user. The touchscreen and the controlling processor (e.g., 120, 220, 320, 420a, and/or 420b) may be configured recognize touchscreen gestures including, for example, but not limited to, tap, double tap, caliper gesture, drag and drop, slide, press and drag, hold and press, etc. In an implementation, the processors 120, 220, 320, 420a, and/or 420b may control a respective display to provide visual representations of data captured by and/or received at the device 110, 210, 310, 410a, and/or 410b. The visual representations may include still images and/or video images (e.g., animated images).

In an implementation, the output device(s) 130, 230, 330, 430a, and 430b and/or the input device(s) 144, 244, 344, 444a, and 444b may include wearable devices such as, for example, a heads-up display mounted onto eyeglasses, a face shield, a watch, and/or devices that may be integrated with other wearable communications devices, such as, for example, an ear bud or a Bluetooth® hands free phone adaptor. The processors 120, 220, 320, 420a, and 420b may control the output devices 130, 230, 330, 430a, and 430b respectively, to provide information for the user. The information may include feedback (e.g., visible feedback, audible feedback, haptic feedback, numerical feedback, and graphical feedback) such as CPR feedback.

The one or more user input devices 144, 244, 344, 444a, and 444b may include, for example, a keyboard, a mouse, joystick, trackball, or other pointing device, a microphone, a camera, etc. Further, the user input devices 144, 244, 344, 444a, and 444b may be a touchscreen and/or another input/output device capable of providing information for the user and capturing information from the user. The touchscreen may be a pressure sensitive touchscreen In an implementation, the user input devices 144, 244, 344, 444a, and/or 444b are configured to capture information, such as, for example, patient medical history (e.g., medical record information including age, gender, weight, body mass index, family history of heart disease, cardiac diagnosis, co-morbidity, left ventricular ejection fraction, medications, previous medical treatments, and/or other physiological information), physical examination results, patient identification, caregiver identification, healthcare facility information, etc.

The processor, memory, communications, and input and/or output components described above are meant to exemplify some types of possibilities. In no way should the aforementioned examples limit the scope of the disclosure, as they are only exemplary embodiments of these components.

Various modifications and additions can be made to the exemplary embodiments discussed without departing from the scope of the present invention. For example, while the embodiments described above refer to particular features, the scope of the disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

What is claimed is:

1. A system for review of clinical data in a playback mode, the system comprising:
an external defibrillator comprising:
at least one first display screen,
a communications module,
at least one first memory, and
at least one first processor coupled to the at least one first memory, the at least one first display screen and the communications module, the at least one first processor configured to:
receive signals indicative of real-time patient data from one or more patient interface devices communicatively coupled to the external defibrillator during ongoing data capture from a patient during a medical encounter with the patient, the one or more patient interface devices comprising electrotherapy electrodes and one or more physiological sensors, and the real-time patient data comprising physiological data comprising electrocardiogram data and one or more of pulse oximetry data and capnography data,
record a time at which a medical event occurred based on the real-time patient data,
control the at least one first display screen to provide a first visual representation of the real-time patient data at an operational interface that displays the real-time patient data at the external defibrillator in real-time as the signals are received, and
transmit the real-time patient data via the communications module; and
at least one auxiliary computing device comprising:
at least one second display screen,
at least one second memory, and
at least one second processor coupled to the at least one second memory and the at least one second display screen, the at least one second processor configured to:
receive the real-time patient data from the external defibrillator, and
control the at least one second display screen to provide a second visual representation of the real-time patient data at a playback interface that is configured to:
display, on an interactive timeline, the real-time patient data comprising the physiological data comprising the electrocardiogram data and the one or more of pulse oximetry data and capnography data as the signals are received and as the real-time patient data comprising the physiological data comprising the electrocardiogram data and the one or more of pulse oximetry data and capnography data is concurrently displayed at the operational interface provided at the external defibrillator,
display an event marker at a position on the interactive timeline that corresponds to occurrence of the medical event, provide at least two data display controls on the playback interface that enable a user to select a start time and an end time that define a user-selected playback interval, provide a snap-to-event capability configured to adjust the user-selected playback interval to an automatically-selected playback interval based at least in part on the event marker, wherein the snap-to-event capability enables the playback interface to move at least one of the user-selected start time or the user-selected end time to the position on the interactive timeline that corresponds to occurrence of the medical event, and replay historic patient data according to the automatically-selected playback interval, during the ongoing data capture from the patient.

2. The system of claim 1
wherein a combination of the real-time patient data and the historic patient data comprises a plurality of time stamps associated with a patient case and
wherein the real-time patient data corresponds to time stamps of the plurality of time stamps that are within a threshold time interval from a current time and the historic patient data corresponds to time stamps of the plurality of time stamps that are greater than the threshold time interval from the current time and less than or equal to a time difference between the current time and a start time of data collection for the patient case by the external defibrillator.

3. The system of claim 1 wherein the operational interface and the playback interface include one or more of different colors and different labels to visually distinguish between the operational interface and the playback interface.

4. The system of claim 1 wherein the first visual representation of the real-time patient data is the same as the second visual representation of the real-time patient data.

5. The system of claim 1 wherein the first visual representation of the real-time patient data is different than the second visual representation of the real-time patient data.

6. The system of claim 1 wherein the one or more patient interface devices comprise one or more of ventilation sensors, respiration sensors, cardiac sensing electrodes, and at least one chest compression sensor.

7. The system of claim 1 wherein the real-time patient data comprises chest compression data comprising one or more of displacement data, velocity data, release velocity data, acceleration data, force data, compression rate data, dwell time data, hold time data, blood flow data, and blood pressure data.

8. The system of claim 7 wherein the physiological data comprises blood pressure, heart rate, respiration rate, heart sounds, lung sounds, respiration sounds, saturation of muscle oxygen ($SMO_2$), cerebral blood flow, electroencephalogram (EEG) signals, brain oxygen level, tissue pH, tissue fluid levels, ultrasound images and/or video, laryngoscope images and/or video, near-infrared reflectance spectroscopy data, pneumography data, cardiography data, lactate, glucose, point of care laboratory measures, and temperature.

9. The system of claim 1 wherein the playback interface comprises:
a data display window configured to provide patient case data comprising one or more of (a) at least a portion of the real-time patient data, or (b) at least a portion of the historic patient data;
and
a media navigation bar configured to capture user input indicative of data display parameters and to control the data display window based on the user input.

10. The system of claim 9 wherein the patient case data comprises:
(a) one or more of cardiac parameters, ventilation parameters, and respiration parameters represented as one or more of waveforms, time trends, and discrete physiological measurements, or
(b) cardiopulmonary resuscitation (CPR) performance data represented as one or more of textual, numerical, and graphical data, or
(c) a combination thereof.

11. The system of claim 1, wherein the medical event is a cardiac arrhythmia detected in the electrocardiogram data.

12. The system of claim 9
wherein the interactive timeline is configured to provide a data preview pop-up window in response to a touchscreen gesture associated with an on-screen cursor
wherein the data preview pop-up window is configured to provide a visual representation of at least a portion of the patient case data that corresponds to a time associated with a position of the on-screen cursor along the interactive timeline, and
wherein the data preview pop-up window provides one or more of an ECG waveform, CPR performance data, physiological waveforms, discrete physiological measurements, device settings, and device actions.

13. The system of claim 9
wherein the playback interface comprises a playback speed selection control configured to adjust a playback speed for the patient case data provided in the data display window, and
wherein the playback interface is configured to automatically adjust the playback speed to provide the historic patient data at a speed determined by the playback speed selection control and provide the real-time patient data at a speed that matches a data display speed for the operational interface.

14. The system of claim 9
wherein the playback interface comprises an event search function, and
wherein the playback interface is configured to provide a user-selectable list of events on an interactive menu in response to a user activation of the event search function and is configured to highlight visual indicators on the interactive timeline in response to a user selection of an event from the user-selectable list of events.

15. The system of claim 9 wherein the playback interface comprises a medical condition selection control configured to:
enable a user selection of a medical condition from an interactive menu of the playback interface, and
determine one or more settings for data display at the playback interface based on the user selection of the medical condition.

16. The system of claim 1,
wherein the at least one first display screen is configured to provide the operational interface and a first playback interface
wherein the playback interface provided by the at least one second display screen is a second playback interface, and
wherein the second playback interface enables a user interactive review of one or more of (a) at least a portion of the real-time patient data, or (b) at least a portion of the historic patient data at the at least one second display screen.

17. The system of claim 16
wherein the first playback interface is configured to capture a user input of a selected data type to display at the at least one auxiliary computing device and
wherein the at least one first processor is configured to provide an instruction comprising the selected data type to display to the at least one auxiliary computing device via the communications module.

18. The system of claim 1, wherein the communications module is configured to communicatively couple to the at least one auxiliary computing device via a cellular network.

19. The system of claim 1, wherein the communications module is configured to communicatively couple to the at least one auxiliary computing device via a computer network.

20. The system of claim 1, wherein the at least one auxiliary computing device comprises a local computing device located proximately to the external defibrillator.

21. The system of claim 1, wherein the at least one auxiliary computing device comprises a remote computing device.

22. The system of claim 21, wherein the communications module enables telemedicine communications with the remote computing device.

23. The system of claim 22, wherein the telemedicine communications comprise one or more of treatment recommendations and diagnoses.

24. The system of claim 22, wherein one or more of (a) at least a portion of the real-time patient data, or (b) at least a portion of the historic patient data available at the playback interface on the remote computing device comprises one or more of non-invasive blood pressure, invasive blood pressure, heart rate, temperature, EtCO2 values, pulse oximeter data, 12-lead data, and waveforms comprising at least one of ECG, EtCO2, and SpO2.

25. The system of claim 22, wherein one or more of (a) at least a portion of the real-time patient data, or (b) at least a portion of the historic patient data available at the playback interface on the remote computing device comprises alarms generated during the ongoing data capture from the patient.

26. The system of claim 1, wherein the operational interface is configured to provide caregiver guidance with one or more of compression feedback or ventilation feedback.

27. The system of claim 1, wherein the at least one auxiliary computing device comprises a group of communicatively coupled computing devices.

28. The system of claim 1, wherein the at least one auxiliary computing device comprises a mobile computing device.

29. The system of claim 1, wherein the playback interface is configured to adjust the user-selected playback interval to the automatically-selected playback interval when the event marker is within a predetermined time of the user selected start time or the user selected end time.

30. The system of claim 29, wherein the pre-determined time is user-configurable.

31. The system of claim 1, wherein the playback interface is configured to provide a play control that enables a user to replay the historic patient data moving forward in time and a rewind control that enables the user to replay the historic patient data moving backward in time.

32. The system of claim 1, wherein
the at least two data display controls on the playback interface enable a user to define the user-selected playback interval to include a historic time and a current time, and
the playback interface is configured to display the real-time data at the playback interface after replay of the historic patient data.

33. The system of claim 1, wherein the playback interface is configured to:
adjust one of the at least two data display controls to a current time if one of the at least two data display controls is within a pre-determined time interval from the current time, and
display the real-time data at the playback interface after replay of the historic patient data.

34. The system of claim 29, wherein a start time or end time for the automatically-selected playback interval coincides with the event marker.

35. The system of claim 1, wherein the medical event is a drug infusion to the patient.

* * * * *